United States Patent [19]
Nasrallah et al.

[11] Patent Number: 5,484,905
[45] Date of Patent: Jan. 16, 1996

[54] RECEPTOR PROTEIN KINASE GENE ENCODED AT THE SELF-INCOMPATIBILITY LOCUS

[75] Inventors: June B. Nasrallah; Mikhasil E. Nasrallah, both of Ithaca; Joshua Stein, Cortland, all of N.Y.

[73] Assignee: Cornell Research Foundation, Inc., Ithaca, N.Y.

[21] Appl. No.: 717,331

[22] Filed: Jun. 19, 1991

[51] Int. Cl.[6] .................... C07H 21/04; C12N 15/29; C12N 9/12
[52] U.S. Cl. ................ 536/23.6; 536/23.1; 536/23.2; 530/379; 435/194
[58] Field of Search .................... 536/27; 435/172.3, 435/320.1, 194; 935/6, 9; 530/379

[56] References Cited

FOREIGN PATENT DOCUMENTS

WO9013654  11/1990  European Pat. Off. ........ C12N 15/83

OTHER PUBLICATIONS

Nature, 345:743, Jun. 21st, 1990.
Molecular and General Genetics, 222:241, (1990).
Proceedings of the National Academy of Sciences of USA, 88:8816 (Oct. 1991).
Biotechnol. Plant Sci.: Relevance Agric. Eighties (Symp), pp. 259–264 (1985).
The Plant Cell, 2(1):29 Jan. 1990.
Theor. Appl. Genet, *1(6):769, Jun. 1991.
C. H. Chen et al., (1990), Mol. Gen. Genet., 222:241–248.
B. A. Lalonde et al., (1989), Plant Cell, 1:249–258.
M. Trick et al., (1989), Mol. Gen. Genet., 218:112–117.
M. K. Kandasamy et al., (1989), Devel. Biol., 134:462–472.

*Primary Examiner*—David T. Fox
*Assistant Examiner*—Bruce R. Campbell
*Attorney, Agent, or Firm*—Sughrue, Mion, Zinn, Macpeak & Seas

[57] ABSTRACT

Described herein is a S receptor kinase gene (SRK), derived from the S locus in *Brassica oleracea*, having a extracellular domain highly similar to the secreted product of the S-locus glycoprotein gene.

14 Claims, 9 Drawing Sheets

```
SRK₆  5'...Exon 1...GAT ATC ▼GGT TAG...Intron 1...3'
              Asp Ile Gly end SRK₂  5'...Exon 1...GAT CTA ▼GGT TAG...Intron 1...3'
              Asp Leu Gly end SLG₆  5'................GAC CTT GTT TAG...3'
                       Asp Leu Val end
```

FIG. 6A

```
       -32                                           +1
SRK6   MKGARNIYHHSY*MSFLLVFVVMLILIHPALSIYINTLSSTESLTISSNKTLVSPGSIFEV  27
SRK2   ===VQ=======TF=====L=L==F======V====S======R====GV==L          27
ZmPK1  =***PRPLAALLSTACI=S=FIALFPRA=S=RD=LP=G=SLVVESYESS==Q=SDGT=SS   27
SLG6   ===V=KP=DN==TL=====F=L====FC==F**=========R=====NN==L          27

SRK6   GFFRTNSRWYLGMWYKKVS***DRTYVWVANRDNPLSNAIGTLKI*SGNNLVLLDH  79
SRK2   ===KPLGR======I====AP*****WK==A========SS======*=======SQ=    81
ZmPK1  ==YEVYTHA*FTFSV==S=TEAAAANNK=I==S==P=R=VHARRSA=TLQKDGNM==T=Y  86
SLG6   ====NSS======I====LL*****====*==========*========G=           81

SRK6   SNKPVWWTNLTRGNERSPVV*AELLANGNFVMRDSSNNDASEYLWQSFDYPTDTLLPEMK 138
SRK2   =TNT==S======A====I*====P=====I=H=N=K=S=GF====F=========    140
ZmPK1  DGAA==RAD***==NFTG=QR=R==DT==L=IE==GG=T****V====S====F==T**  137
SLG6   T==S=========L===*======S===============Y==========         140
```

FIG. 6B

```
SRK6    LGYNLKTGLNRFLTSWRSSDDPSSGNFSYKLETQ*SLPEFYLSRE********NFPM 186
SRK2    ===D=====R======KG======V===DIRRG====I==INQFLN******QRVET 193
ZmPK1   *Q==I=AAT=LVP*TTQSR=P==YIFRFSDLSV=SLI=HVPQVSDIYWPDPDQ=LYQ 191
SLG6    ===D==================================R*=======WHG**********I=== 188

SRK6    HRSGPWNGIRFSGIPEDQKLSYMVYNFIENNEEVAYTFRMTNNSFYSRLTLISEGYFQRL 246
SRK2    Q=========ME======V=G=N====YT===S=H===Q==I=====*V==LTLD== 252
ZmPK1   DGRNQY=ST=LGMLTDSGV=A**SSD=ADGQAL==***SDVGPGVKR====DPD=NLRLY 246
SLG6    =========V================T========I=======S========== 248

SRK6    TWYPSIRIWNRFWSSPVDPQCDTYIMCGPYAYCDVNTSPVCNCIQGFNPRNIQQWDQRVW 306
SRK2    ==I=PS=D=SL==TL=T=V*==PLYL==S=S===LI===N===R==V=K=P===L=DG 311
ZmPK1   SMND=DGS=SV*SMVAMTQP=NIHGL===NGI=HYSPT=T=S=PP=YAT==PGN=***** 300
SLG6    ==N===G==================G=================== 308
```

FIG. 6C

```
SRK6   AGGCIRRTQLSCSGDGFTRMKKMKLPETTMATVDR****SIGVKECKKRCISDCNCTAFA 362
SRK2   TR==V=T==M======L=LNN=N==D=KT=====****TMD==K=EE===L======S== 367
ZmPK1  TE===MAIVNTT=DRYDKRS=RFVR==N=DFWGS=QQHLL=VSLRT=RDI=====T=KG=Q 360
SLG6   ==========R========N=====I=****=========E===L========= 364

SRK6   NADIRNGGSGCVIWTERLEDIRNYATDAIDGQDLYVRLAAADI****AKKRNASGKIISL 418
SRK2   I===V====L===F==GE==VA==KF****==VG======N===LDISSGE==DRT=== GW 424
ZmPK1  YQE****=T=SCYPKAY=FSG=T=P=SDV**RTI=LK=PTGVSVSNALIP=SDVFDSVPR 414
SLG6   ========T======G=D=M===***VAH======V==LV 405

SRK6   TVGVSVLLLLIMFCLWKRKQKRAKASAISIANTQRNQNLPMNEM******VLSSK 467
SRK2   SI=S==M=I=SV=L==F=R=R==Q===D=TP=VGN=****VL===V*****====PR= 471
ZmPK1  RLDCDRMNKSIREPF***PDVH=TGGGESKWFYFYGFIAAFFVV=VSFISFAWFFVLKRE 471
```

FIG. 6D

```
SRK6  *RE****FSGEYKFEEL**ELPLIEMETVVKATENFSSCNKLGQGGFGIVYKGRLLDGKEI 521
SRK2  K=N****====DDV=N**=====M=F=A==T===H==DF==V=K====V====Q==  526
ZmPK1 L=PSELWAS=KGYKAMTSNFRRYSYRFL====RK=KV**E==R=ES=T===V=E=DRHV 529
      /........./........ KINASE SUBDOMAIN I ........./.........

SRK6  AVKRLSKTSVQGTDEFMNEVTLIARLQHINLVQVLGCCIEGDEKMLIYEYLENLSLDSYL 581
SRK2  =====EM=A=======R=MQSFS=N===RL===VYEG==I======H=  586
ZmPK1 ===K=ENVR*==KEVFQA=LSV=G=IN=M===RIW=F=S==SHRL=VS==V==G==ANI= 588
      .II........./........III........./.........IV........./.........V........

SRK6  FGKTRRSKLNWNERFDITNGVARGLLYLHQDSRFRIIHRDLKVSNILLDKNMIPKISDFG 641
SRK2  =DE===SCM===QM====I==I==============A==V===D=T======  646
ZmPK1 =SEGGNIL=D=EG==N=AL===K===A===HECLEWV==C=V=PE====QAFE===T==  648
      ........./.........VI........./.........
```

FIG. 6E

```
SRK6   MARIFERDETEANTMKVVGTYGYMSPEYAMYGIFSEKSDVFSFGVIVLEIVSGKKNRGFY 701
SRK2   =====G======D=R===================N=T==M=============L===I===R=K=LC 706
ZmPK1  LVKLLN=GGSTQ=VSH=R==L===IA==WVSSLPITA=V==Y=Y==VL==LLT=TRVSELV 708
       ..VII........../.........VIII......../..............IX............/

SRK6   ****NLDYENDLLSYVWSRWKEGRALEIVDPVIVDSLSSQPSIFQPEVLKCIQIGLLCV 757
SRK2   ****DS=SSLN==GC===RN===QG====K==I==**SSPT=R=RN=R=I=R=L====== 759
ZmPK1  GGTDEVHSMLRK=VRML==AKL==EEQSWI=GYLDSK=NRPVNYV=ARTLI=***LAVS=L 765
       ......X......./............/.............XI............

SRK6   QELAEHRPAMSSVVWMFGSEATEIPQPKPPGYCVRRSPYELDPSSSWQCDENESWTVNQY 817
SRK2   ==RV=D==M=====L=L====AL====Q=====SG=S**=ETY=RR***DD=NC====I 814
ZmPK1  E=DRSK==T=EHA=QTLL=ADD 787
       ................./

SRK6   TCSVIDAR 825
SRK2   =M=I==== 822
```

RECEPTOR PROTEIN KINASE GENE ENCODED AT THE SELF-INCOMPATIBILITY LOCUS

The making of the present invention was supported, in part, by funds from the United States Government. Accordingly, the federal government has certain statutory rights to the invention as set forth in 35 USC 200 et seq.

BACKGROUND OF THE INVENTION

Pollination and the subsequent invasive growth of pollen tubes into the female stigmatic and pistil tissues prior to fertilization provides an opportunity to study cell-cell interactions in flowering plants. In crucifers such as *Brassica oleracea*, self recognition between pollen and stigma is controlled by the multi-allelic self-incompatibility, or S locus. Pollen germination and/or tube growth are arrested at the stigma surface if pollen and stigma are borne by plants having identical S locus alleles. This arrest prevents self-fertilization and is termed the selfincompatibility (SI) response. Two related genes have been identified at the S locus using molecular methods. Of these, only one gene, the S locus glycoprotein (SLG) gene has been characterized extensively. SLG encodes a secreted glycoprotein that is highly polymorphic in different S-locus alleles, and its expression in stigmatic papillae and anthers, is consistent with models for Sl in which both pollen and stigma bear recognition determinants derived from the S locus.

Plant science has recognized for many years that hybridization of closely related plants often results in the production of an offspring (F1) generation having a combination of desirable traits previously possessed separately by the parent plants. Also, hybrid plants of various crop species commonly possess vigor or heterosis which significantly contributes to the species' crop yield. Accordingly, many hybrid crosses are of considerable economic importance.

Since plants selected for hybridization studies are commonly capable of undergoing both self-pollination (i.e., the plants are "self compatible") and crosspollination, the desired hybrid crosses have been difficult to achieve on a reliable basis while operating on a commercial scale. In order to achieve hybrid crosses on a commercial scale, it is necessary to control cross-pollination in the substantial absence of self-pollination (i.e., plants that are "self-incompatible").

In more than 3,000 species representing diverse angiosperm families, selffertilization is blocked by a genetic controlled mechanism termed "selfincompatibility". This phenomenon facilitates out-crossing by inhibiting growth of self pollen in pistil tissue. Following self-pollination, interaction between the stigma or style and pollen elicits a defined morphological response preventing normal pollen tube growth. Fertilization is thus prevented as the pollen tubes are unable to penetrate the full length of the stigma ands-style, and gamete nuclei in the pollen are unable to reach female gametophyte tissue. The specificity of this interaction is determined by one or more genetic loci, and requires the identity of alleles carried by the male and female parents.

The control of incompatibility is attributed to a single genetic locus with multiple alleles. As with other allelomorphs, any two alleles may be carried by a diploid plant; incompatibility occurs if the alleles expressed in pollen and pistil are identical.

Incompatibility systems are generally divided into two groupings: (i) the gametophytic system in which the phenotype of a pollen grain is determined by the haploid pollen genotype; and (ii) the sporophytic system in which the pollen phenotype is determined by the genotype of the parental plant. In the sporophytic system of incompatibility, exemplified by the genus Brassica, and other crucifers belonging to the family Brassicaceae (which includes broccoli, cabbage, kale, mustards, oil seed crops and radish), the self-incompatible inhibition is localized at the stigma outer surface and occurs within minutes by failure of self-pollen to germinate and/or invade the papillar cells on the stigma surface. Thus, selffertilization is prevented. In Brassicaceae, self-incompatibility is under control of a single multi-allelic locus (numerous alleles have been identified in natural populations), the S-locus, and phenotype of pollen is determined by diploid of the sporophyte [see Heredity 9:53 (1955)]. While the mechanism of pollen recognition is not understood, observations that self-incompatibility responses occur when the same S-allele is active in pollen and stigma suggest pollen inhibition is based on expression of a single S-locus gene in the male and female structures of the flower. Sporophytic control of pollen phenotype has furthermore been postulated to result from expression of this S-locus gene in the taperum, the layer of sporophytic cells that lines the anther and functions to nourish developing pollen grains [see Nature 218:90 (1968) and Ann Rev Plant Physio 26:403 (1975)]. Based largely on ultrastructural observations, this cellular layer is thought to act as nurse cells for developing microspores, and to synthesize and release materials that are incorporated into the outer coat (exine) of pollen grains just prior to and during tapetal dissolution late in pollen development.

A gene involved in the specific recognition of self pollen is also expected to be sporophytically expressed in the host's anthers during pollen development. While blot analysis of anther RNA has identified a low-abundance transcript with homology to the S-locus glycoprotein gene [see Ann Rev Genetics 23:121 (1989)] these studies could not distinguish between expression of the S-locus glycoprotein related genes bund in the Brassica genome..

Perhaps the most experimentally tractable route towards molecular analysis of genetic control for incompatibility is suggested by detection of antigens specific to various S-locus alleles in stigma homogenates from different Brassica strains which have been shown to correspond to glycoproteins and may be resolved in various electrophoretic systems. Several lines of evidence suggest these glycoproteins play an important role in incompatibility: (1) mobilities of these molecules vary in stigma extracts from Brassica strains with different S-locus alleles; (2) these molecules are found exclusively on the stigma surface (specifically in papillar cells), the site of the initial contact between the pollen and stigma; (3) an increased rate of synthesis of these S-locus specific glycoproteins in the developing stigma correlates well with onset of the incompatibility reaction in the stigma; and (4) glycoproteins in the stigma of self incompatible lines of *B. oleracea* (kale), *B. campestris*, and related *Raphanus sativus* (radish) have been identified which cosegregate with their corresponding S-alleles in the F1 and F2 generations, indicating that the gene responsible for this polymorphism is at the S-locus.

These glycoproteins have been designated S-locus specific glycoprotein ("SLSG"). Each S-genotype has its own unique glycoprotein, and to date more than twenty different SLSG have been correlated with S-alleles. Furthermore, SLSG encoded by different S alleles exhibit extensive polymorphism and are distinguishable on the basis of their characteristic charge, molecular weight and antigenic properties. Also, SLSG accumulate during stigma development and are synthesized at a maximal rate coincident with acquisition of the developing stigma for the ability to reject self pollen.

Cell-specific expression of these genes in the stigma are well characterized. S-locus gene transcripts were localized by in Situ hybridization to the papillar cells of the stigma surface [see PNAS USA 85:5551 (1988)], and S-locus gene glycoprotein products were shown by ultra structural immunocytochemistry to accumulate in the papillar cell walls [see Dev Biol 134:462 (1989)]. These results, and the genetic linkage of S-locus glycoprotein genes to the S-locus, have led to one aspect of the present invention, that is, that these genes encode the stigmatic determinants of self-incompatibility.

The S-locus glycoprotein genes, and specifically those genes from B. oleracea which have been designated as $S_6$, $S_{13}$, $S_{14}$ and $S_{22}$, and the $S_8$ genome from B. campestris, are described in copending U.S. patent application Ser. No. 07/568,657, now abandoned, filed Aug. 14, 1990 which is a continuation of application 06/762,245 filed Aug. 5, 1985 and now abandoned, application 07/459,069 filed Dec. 29, 1989 and application 07/532,907 filed Jun. 4, 1990, now abandoned, the disclosures of these applications of which are incorporated in toto herein.

SUMMARY OF THE INVENTION

We have now discovered a second S-locus-linked gene which encodes a putative receptor protein kinase, and have designated it SRK, for S Receptor Kinase. Although only a limited number of SRK alleles are described herein, the term is meant to be broadly defined in that mutants or variants of the DNA sequences described herein for the SRK gene are to be considered part of the present invention provided that such mutants and variants express essentially similar peptides having essentially the same function as the peptides expressed by the SRK alleles described herein. The structure of this putative receptor is similar to that predicted in a recently described maize root cDNA clone, ZMPK1, whose function has not been determined [see Nature 345:743 (1990)]. Similar forces appear to have shaped the evolution of SRK and SLG, such that alleles of SRK also encode distinctive polymorphic variant. And like SLG, SRK is transcribed specifically in pistils and anthers. These facts implicate SRK not only as a determinant of pollen recognition, but as a primary transmitter of the recognition signal that leads to the SI response.

The method according to the present invention which is directed to the isolation and use of both a SLG gene and an SRK gene, and which will be described in below, may use SRK and SLG genes which have been isolated from a homozygous selfincompatible donor plant having a genotype selected from the group consisting of Brassica oleracea S2, Brassica oleracea S6, Brassica oleracea S13, Brassica oleracea $S_{14}$, Brassica oleracea S22, and Brassica campestris S8. The SLG and SRK genes derived from an S-allele homozygote genotype share about 90% DNA and amino acid sequence identity in their S regions. This observation suggests that these genes act in concert to determine S-allele specificity. The determination of selfincompatibility phenotype thus appears to require a minimum expression of the two linked S-locus linked genes.

The present invention has, therefore, a great number of different aspects including the description of previously undescribed $SRK_2$ DNA and peptide sequences; the description of previously undescribed $SRK_6$ DNA and peptide sequences; methods of cloning additional SRK genes; vectors containing the SRK genome; transgenic plants transformed with the SRK genome; the uses of SLG probes to isolate the SRK genome from plant-derived materials; and S-domain, transmembrane and kinase domain sequences of the SRK genomes; methods for imparting self-incompatibility to recipient plants by transforming self-incompatibility genes into appropriate plant strains; the establishment of transgenic plants containing the SRK and SRK-linkedSLG genomes; and the use of such transgenic plants to produce self-incompatible offspring.

BRIEF DESCRIPTION OF THE DRAWINGS

A more complete and thorough understanding of the present invention may be had by reference to the following figures and examples which are presented to exemplify, not limit, the present invention. In the figures.

FIG. 6 depicts a comparison of the $SRK_2$, $SRK_6$, $SLG_6$ and ZmPK1 genomes.

DETAILED DESCRIPTION OF THE INVENTION

Figure 1:
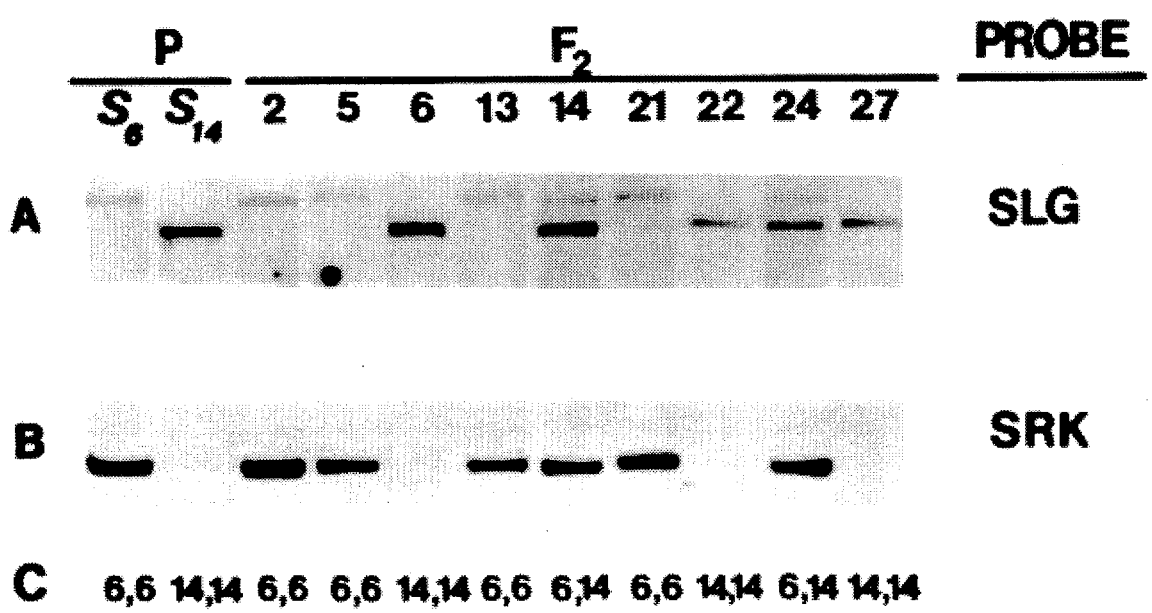
FIG. 1 is a photomicrograph representing an restriction fragment length polymorphism (RFLP) analysis of an $F_2$ population segregating for the S6 and S14 self-incompatibility alleles.

In specific reference to the figures, which contain graphic representations of the data collected in the subsequent examples, FIG. 1 depicts DNA which has been isolated from parental (P) plants homozygous for either the $S_6$ or $S_{14}$ allele and from nine $F_2$ progeny, digested with Eco R1, and analyzed by blot hybridization. The segregation patterns observed following hybridization with probe specific for SLG (FIG. 1A), and $SRK_6$ (FIG. 1B) are shown. FIG. 1C indicates the incompatibility phenotype of each plant as determined by pollination tests. The incompatibility phenotype of the $F_2$ progeny derived from a cross between the $S_6$ and $S_{14}$ homozygotes was determined by crosses to tester homozygous strains and by diallel analysis. Pollen-free mature stigmas were pollinated, and after a period of 12–24 hours, the stigmas were excised and stained with decolorized aniline blue. The extent of pollen-tube development was examined by fluorescence microscopy using well known protocols described in Example VI.

Figure 2:
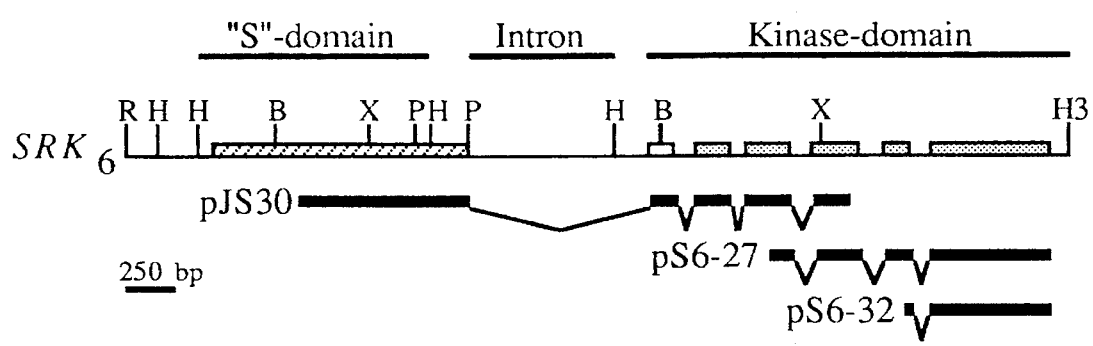
FIG. 2 is a physical map of the sequenced genomic fragment containing $SRK_6$ and flanking regions.

FIG. 2 is, as described above, a physical map of the sequenced genomic fragment containing $SRK_6$ and flanking regions. The exons in this map appear as boxes; the hatched box represents exon I and containing the "S" domain; the open box represents exon 2 and contains the putative transmembrane domain; and the stippled boxes representing the remaining 5 exons that contain the putative kinase domain. The extents of 3 cDNA clones are shown below the map, and the lines above the map indicate the 3 $SRK_6$-derived probes used in the making of the present invention. The various restriction endonuclease sites are indicated as follows: R, Eco RI; H, Hinc II; Xb, Xba I; B, Bcl I; Xh, Xho I: P, Pst I; and H3, Hind III.

Figures 3, 4:
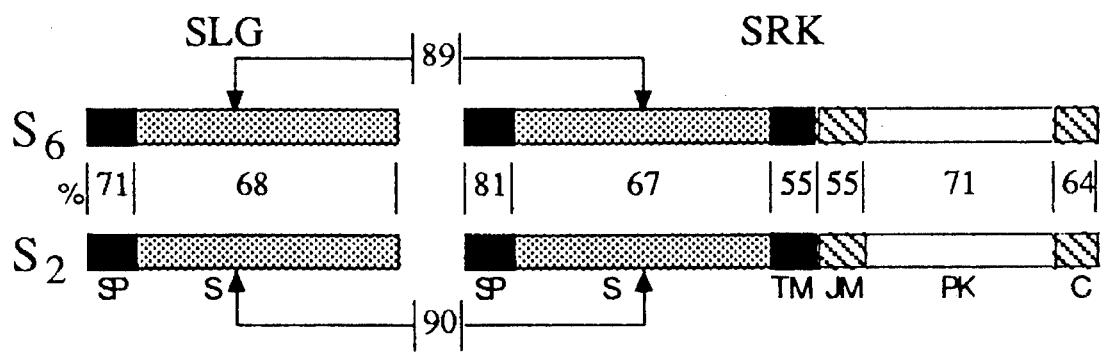
FIG. 3 is the DNA sequence at the first exon/intron junction in $SRK_6$ and $SRK_2$ and the corresponding sequence in $SLG_6$.
FIG. 4 depicts a concerted evolution of the SLG/SRK gene pair within S genotypes and their divergence between genotypes.

In FIG. 4, a concerted evolution of the SLG/SRK gene pair within S genotypes and their divergence between genotypes is depicted. The predicted SLG and SRK proteins encoded by the $S_6$ and $S_2$ genotypes are represented schematically. The numbers indicate the % identity between putative domains; SP, signal peptide; S, "S" domain; TM, transmembrane domain; JM, juxtamembrane domain; PK, protein kinase domain; and C, carboxy-terminus domain.

Figure 5A:
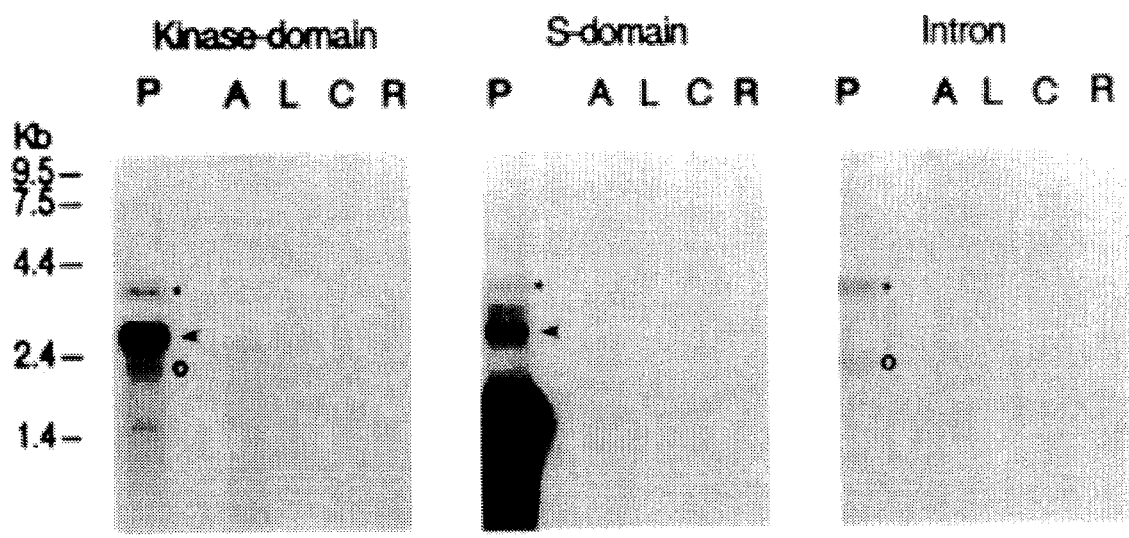
FIGS. 5A–5C are a photomicrograph depicting the expression of the $SRK_6$ gene.
Figure 5B:
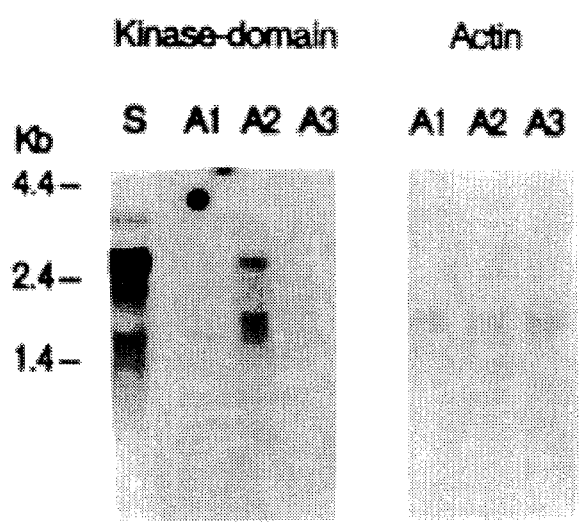
Figure 5C:
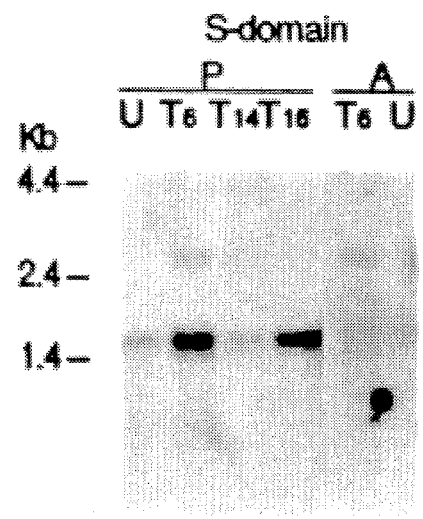

The photomicrograph of FIG. 5 describes the $SRK_6$-homologous transcripts in pistils (P), anthers (A), leaves (L), cotyledons (C) and roots (R) of Brassica oleracea $S_6S_6$. Each lane contained about 2 μg of poly(A) RNA, and the blot was hybridized sequentially with a $^{32}$P-labeled probe derived from the kinase domain, the first intron, and the "S" domain of $SRK_6$. Subsequent hybridization with the actin probe showed comparable amounts of RNA in each lane. The arrowhead, asterisk and circle in the FIG. 5 panels denote the SRK-encoded transcripts described in the text. The migration of RNA molecular weight markers is shown to the left. FIG. 5B was prepared from $SRK_6$-homologous transcripts in developing Brassica anthers. Each lane contained about 5 μg of poly(A) RNA isolated from anthers that contained uninucleate (A1), binucleate (A2), and trinucleate (A3) microspores. Stages were determined by DAPI staining of nuclei according to the protocols of Toriyama et al [see Dev. Biol.143:427 (1991)]. The blot was first hybridized with a $^{32}$P-labeled probe derived from the kinase domain of $SRK_6$, and subsequently with an actin probe to show equivalent amounts of RNA in all three lanes. FIG. 5C demonstrates the expression of $SRK_6$ in transgenic Brassica. Poly(A) RNA from transgenic plants (T6 and T14), and a control untransformed plant (U) was hybridized with the $SRK_6$ "S"-domain probe. Approximately 10 times more anther (A) than pistil (P) RNA was analyzed. The differences in the intensities of the endogenous pistil 1.6 kb transcripts between plants reflect the differences in the amounts of RNA loaded in each lane.

FIG. 6 represents a comparison of the $SRK_2$, $SRK_6$, $SLG_6$ and ZmPK1 genomes in single letter code (the $SRK_2$ sequence is given in the following description), and the corresponding sequence in $SLG_6$. The arrowheads indicate the splice sites in the sequence. The dots represent nucleotides omitted for diagrammatic clarity. The SRK genes have an in-frame stop codon located 2 nucleotides downstream of the 5' splice site of intron 1 which is removed in fully spliced transcripts. Transcripts of SLG are not spliced and therefore retain the stop codon at this position.

More particularly, the present invention relates, in part, to the nucleotide sequence of the $SRK_6$ coding region as follows: (SEQ. NO. 1)

| 1 | ATG | AAA | GGT | GCA | CGA | AAC | ATC | TAT | CAC | CAT | TCT | TAC | ATG |
|---|---|---|---|---|---|---|---|---|---|---|---|---|---|
| 40 | TCC | TTT | TTG | CTC | GTC | TTC | GTT | GTC | ATG | ATT | CTA | ATT | CAT |
| 79 | CCT | GCC | CTT | TCG | ATC | TAT | ATC | AAC | ACT | TTG | TCG | TCT | ACA |
| 118 | GAA | TCT | CTT | ACA | ATC | TCA | AGC | AAC | AAA | ACA | CTT | GTA | TCT |
| 157 | CCC | GGT | AGT | ATC | TTC | GAG | GTC | GGC | TTC | TTC | AGA | ACC | AAT |
| 196 | TCT | CGT | TGG | TAT | CTC | GGG | ATG | TGG | TAC | AAG | AAA | GTG | TCC |
| 235 | GAC | AGA | ACC | TAT | GTA | TGG | GTT | GCC | AAC | AGA | GAT | AAC | CCA |
| 274 | CTC | TCC | AAT | GCC | ATT | GGA | ACC | CTC | AAA | ATC | TCA | GGC | AAT |
| 313 | AAT | CTT | GTC | CTC | CTT | GAT | CAC | TCC | AAT | AAA | CCT | GTT | TGG |
| 352 | TGG | ACG | AAT | CTT | ACT | AGA | GGA | AAT | GAG | AGA | TCT | CCG | GTG |
| 391 | GTG | GCT | GAG | CTT | CTC | GCT | AAC | GGA | AAC | TTC | GTG | ATG | CGA |
| 430 | GAC | TCC | AGT | AAC | AAC | GAC | GCA | AGT | GAA | TAC | TTG | TGG | CAA |
| 469 | AGT | TTC | GAT | TAC | CCT | ACG | GAT | ACT | TTG | CTT | CCA | GAG | ATG |
| 508 | AAA | CTG | GGT | TAC | AAC | CTC | AAA | ACA | GGG | TTG | AAC | AGG | TTC |
| 547 | CTT | ACA | TCA | TGG | AGA | AGT | TCA | GAT | GAT | CCA | TCA | AGC | GGG |
| 586 | AAT | TTC | TCG | TAC | AAG | CTC | GAA | ACC | CAA | AGT | CTT | CCT | GAG |
| 625 | TTT | TAT | CTA | TCG | CGG | GAG | AAC | TTT | CCA | ATG | CAT | CGG | AGT |
| 664 | GGT | CCA | TGG | AAT | GGA | ATC | CGA | TTT | AGT | GGC | ATA | CCA | GAG |
| 703 | GAC | CAA | AAG | CTG | AGT | TAC | ATG | GTG | TAC | AAT | TTC | ATA | GAG |
| 742 | AAT | AAT | GAA | GAG | GTC | GCT | TAT | ACA | TTC | CGA | ATG | ACC | AAC |
| 781 | AAC | AGC | TTC | TAC | TCG | AGA | TTG | ACA | CTA | ATT | TCC | GAA | GGG |

-continued

| 820 | TAT | TTT | CAG | CGA | CTG | ACG | TGG | TAT | CCG | TCA | ATA | AGG | ATA |
|---|---|---|---|---|---|---|---|---|---|---|---|---|---|
| 859 | TGG | AAC | AGG | TTC | TGG | TCT | TCT | CCA | GTG | GAC | CCC | CAG | TGT |
| 898 | GAT | ACT | TAC | ATA | ATG | TGT | GGA | CCT | TAC | GCT | TAC | TGT | GAC |
| 937 | GTG | AAC | ACA | TCA | CCG | GTT | TGT | AAC | TGT | ATC | CAA | GGG | TTC |
| 976 | AAT | CCC | CGG | AAT | ATA | CAG | CAG | TGG | GAT | CAG | AGA | GTC | TGG |
| 1015 | GCA | GGT | GGG | TGT | ATA | AGG | AGG | ACG | CAG | CTT | AGC | TGC | AGT |
| 1054 | GGA | GAT | GGT | TTT | ACC | AGG | ATG | AAG | AAG | ATG | AAG | TTG | CCA |
| 1093 | GAA | ACT | ACG | ATG | GCG | ACT | GTC | GAC | CGT | AGT | ATT | GGT | GTG |
| 1132 | AAA | GAA | TGT | AAG | AAG | AGG | TGC | ATT | AGC | GAT | TGT | AAT | TGT |
| 1171 | ACC | GCT | TTT | GCA | AAT | GCA | GAT | ATC | CGG | AAT | GGT | GGG | TCG |
| 1210 | GGT | TGT | GTG | ATT | TGG | ACC | GAA | CGC | CTT | GAG | GAT | ATC | CGG |
| 1249 | AAT | TAC | GCT | ACT | GAC | GCT | ATT | GAC | GGT | CAA | GAT | CTT | TAT |
| 1288 | GTC | AGA | TTG | GCT | GCA | GCT | GAT | ATC | GCT | AAG | AAG | AGA | AAC |
| 1327 | GCG | AGT | GGG | AAA | ATT | ATA | AGT | TTG | ACT | GTT | GGT | GTT | AGT |
| 1366 | GTT | CTG | CTT | CTG | CTG | ATC | ATG | TTC | TGC | CTC | TGG | AAA | AGA |
| 1405 | AAA | CAA | AAG | CGA | GCA | AAA | GCA | AGT | GCA | ATA | TCC | ATT | GCA |
| 1444 | AAT | ACA | CAG | AGA | AAC | CAA | AAC | TTG | CCT | ATG | AAC | GAG | ATG |
| 1493 | GTA | CTA | TCA | AGC | AAG | AGA | GAG | TTT | TCT | GGA | GAG | TAC | AAA |
| 1522 | TTT | GAG | GAA | CTG | GAA | CTT | CCA | TTG | ATA | GAG | ATG | GAA | ACT |
| 1561 | GTT | GTC | AAA | GCC | ACC | GAA | AAT | TTC | TCC | AGC | TGT | AAC | AAA |
| 1600 | CTC | GGA | CAA | GGT | GGT | TTT | GGT | ATT | GTT | TAC | AAG | GGA | AGA |
| 1639 | TTA | CTT | GAC | GGG | AAA | GAA | ATT | GCA | GTA | AAA | AGG | CTA | TCA |
| 1678 | AAG | ACG | TCA | GTT | CAA | GGG | ACT | GAT | GAG | TTT | ATG | AAT | GAG |
| 1717 | GTG | ACA | CTA | ATT | GCG | AGG | CTT | CAG | CAT | ATA | AAC | CTT | GTT |
| 1756 | CAA | GTT | CTT | GGC | TGT | TGC | ATT | GAA | GGA | GAT | GAG | AAG | ATG |
| 1795 | TTG | ATA | TAT | GAG | TAT | TTG | GAA | AAT | TTA | AGC | CTT | GAT | TCT |
| 1834 | TAT | CTC | TTT | GGT | AAA | ACC | CGA | AGG | TCT | AAG | CTA | AAT | TGG |
| 1883 | AAT | GAG | AGA | TTC | GAC | ATT | ACC | AAT | GGT | GTT | GCT | CGA | GGG |
| 1912 | CTT | TTA | TAT | CTT | CAT | CAA | GAC | TCA | CGG | TTT | AGG | ATA | ATC |
| 1951 | CAC | AGA | GAT | TTG | AAA | GTA | AGT | AAC | ATT | TTG | CTT | GAC | AAA |
| 1990 | AAT | ATG | ATC | CCA | AAG | ATC | TCG | GAT | TTT | GGG | ATG | GCC | AGG |
| 2029 | ATA | TTT | GAA | AGG | GAC | GAA | ACG | GAA | GCT | AAC | ACA | ATG | AAG |
| 2068 | GTG | GTC | GGA | ACA | TAC | GGC | TAC | ATG | TCC | CCG | GAA | TAC | GCA |
| 2107 | ATG | TAT | GGG | ATA | TTC | TCG | GAA | AAA | TCA | GAT | GTT | TTC | AGT |
| 2146 | TTT | GGA | GTC | ATA | GTT | CTT | GAA | ATT | GTT | AGT | GGA | AAG | AAG |
| 2185 | AAC | AGA | GGA | TTC | TAC | AAC | TTG | GAC | TAC | GAA | AAC | GAT | CTC |
| 2224 | CTA | AGC | TAT | GTA | TGG | AGT | CGT | TGG | AAG | GAA | GGA | AGA | GCG |
| 2273 | CTA | GAA | ATC | GTA | GAT | CCC | GTC | ATC | GTA | GAT | TCA | CTG | TCA |
| 2302 | TCA | CAG | CCA | TCA | ATA | TTT | CAA | CCA | CAA | GAA | GTC | CTA | AAA |

| | | | | | | | | | | | | | |
|---|---|---|---|---|---|---|---|---|---|---|---|---|---|
| 2341 | TGT | ATT | CAA | ATT | GGT | CTC | TTG | TGT | GTT | CAA | GAA | CTT | GCA |
| 2380 | GAG | CAC | AGA | CCA | GCG | ATG | TCG | TCT | GTG | GTT | TGG | ATG | TTT |
| 2419 | GGA | AGT | GAA | GCA | ACA | GAG | ATT | CCT | CAG | CCT | AAA | CCG | CCA |
| 2458 | GGT | TAT | TGC | GTC | AGA | AGA | AGT | CCT | TAT | GAA | CTT | GAT | CCT |
| 2497 | TCA | TCA | AGT | TGG | CAA | TGT | GAC | GAA | AAT | GAA | TCC | TGG | ACG |
| 2536 | GTG | AAC | CAG | TAC | ACC | TGC | TCA | GTC | ATT | GAT | GCC | CGG | |
| 2572 | TAATATGATA | | GCTGAGTGAT | | TCAATATCAT | | ATGTGAAAGA | | GGGAAAATAA | | | | |
| 2622 | AATCTCATTA | | GATAAGTAGG | | TTATTTCGAT | | AACCACTTCT | | TGTTATTTTC | | | | |
| 2672 | TGGCGGTGTT | | GTCATTATCC | | CCTTTATATT | | AAAAAGAAGC | | ATTTGTATTA | | | | |
| 2722 | AATCCCCTTG | | CCTCAAGAGA | | TATTCACAAG | | AATACTATTG | | TGACGTGACA | | | | |
| 2772 | GCCTCACTAT | | CGTTTAAACA | | TTACAATGCT | | GACGTGTGGC | | TTGTAAATAG | | | | |
| 2822 | CTTCTCAGAC | | CA | | | | | | | | | | |

In this sequence, bases 1–478 were derived from the genomic clone; the remaining sequence was derived from cDNA clones pJS30 (nucleotides 479–2001), pS6–27 (nucleotides 1723–2763), and pS6–32 (nucleotides 2180–2833). The underlined nucleotides denote the positions of the putative signal-yielding peptide (1–97), and (1340–1399) the transmembrane domains. The S-locus binding domain of this DNA molecule has about 70% sequence identity to an SLG gene from Brassica.

The amino acid sequence for the SRK$_6$ coding region according to the present invention is: (SEQ. NO. 2)

| | | | | | | | | | | | | | | |
|---|---|---|---|---|---|---|---|---|---|---|---|---|---|---|
| Met | Lys | Gly | Ala | Arg | Asn | Ile | Tyr | His | His | Ser | Tyr | Met | Ser | Phe |
| | | | | 5 | | | | | 10 | | | | | 15 |
| Leu | Leu | Val | Phe | Val | Val | Met | Ile | Leu | Ile | His | Pro | Ala | Leu | Ser |
| | | | | 20 | | | | | 25 | | | | | 30 |
| Ile | Tyr | Ile | Asn | Thr | Leu | Ser | Ser | Thr | Glu | Ser | Leu | Thr | Ile | Ser |
| | | | | 35 | | | | | 40 | | | | | 45 |
| Ser | Asn | Lys | Thr | Leu 50 | Val | Ser | Pro | Gly | Ser 55 | Ile | Phe | Glu | Val | Gly 60 |
| Phe | Phe | Arg | Thr | Asn 65 | Ser | Arg | Trp | Tyr | Leu 70 | Gly | Met | Trp | Tyr | Lys 75 |
| Lys | Val | Ser | Asp | Arg 80 | Thr | Tyr | Val | Trp | Val 85 | Ala | Asn | Arg | Asp | Asn 90 |
| Pro | Leu | Ser | Asn | Ala 95 | Ile | Gly | Thr | Leu | Lys 100 | Ile | Ser | Gly | Asn | Asn 105 |
| Leu | Val | Leu | Leu | Asp 110 | His | Ser | Asn | Lys | Pro 115 | Val | Trp | Trp | Thr | Asn 120 |
| Leu | Thr | Arg | Gly | Asn 125 | Glu | Arg | Ser | Pro | Val 130 | Val | Ala | Glu | Leu | Leu 135 |
| Ala | Asn | Gly | Asn | Phe 140 | Val | Met | Arg | Asp | Ser 145 | Ser | Asn | Asn | Asp | Ala 150 |
| Ser | Glu | Tyr | Leu | Trp 155 | Gln | Ser | Phe | Asp | Tyr 160 | Pro | Thr | Asp | Thr | Leu 165 |
| Leu | Pro | Glu | Met | Lys 170 | Leu | Gly | Tyr | Asn | Leu 175 | Lys | Thr | Gly | Leu | Asn 180 |
| Arg | Phe | Leu | Thr | Ser 185 | Trp | Arg | Ser | Ser | Asp 190 | Asp | Pro | Ser | Ser | Gly 195 |
| Asn | Phe | Ser | Tyr | Lys 200 | Leu | Glu | Thr | Gln | Ser 205 | Leu | Pro | Glu | Phe | Tyr 210 |

-continued

| | | | | | | | | | | | | | | |
|---|---|---|---|---|---|---|---|---|---|---|---|---|---|---|
| Leu | Ser | Arg | Glu | Asn 215 | Phe | Pro | Met | His | Arg 220 | Ser | Gly | Pro | Trp | Asn 225 |
| Gly | Ile | Arg | Phe | Ser 230 | Gly | Ile | Pro | Glu | Asp 235 | Gln | Lys | Leu | Ser | Tyr 240 |
| Met | Val | Tyr | Asn | Phe 245 | Ile | Glu | Asn | Asn | Glu 250 | Glu | Val | Ala | Tyr | Thr 255 |
| Phe | Arg | Met | Thr | Asn 260 | Asn | Ser | Phe | Tyr | Ser 265 | Arg | Leu | Thr | Leu | Ile 270 |
| Ser | Glu | Gly | Tyr | Phe 275 | Gln | Arg | Leu | Thr | Trp 280 | Tyr | Pro | Ser | Ile | Arg 285 |
| Ile | Trp | Asn | Arg | Phe 290 | Trp | Ser | Ser | Pro | Val 295 | Asp | Arg | Gln | Cys | Asp 300 |
| Thr | Tyr | Ile | Met | Cys 305 | Gly | Pro | Tyr | Ala | Tyr 310 | Cys | Asp | Val | Asn | Thr 315 |
| Ser | Pro | Val | Cys | Asn 320 | Cys | Ile | Gln | Gly | Phe 325 | Asn | Pro | Arg | Asn | Ile 330 |
| Gln | Gln | Trp | Asp | Gln 335 | Arg | Val | Trp | Ala | Gly 340 | Gly | Cys | Ile | Arg | Arg 345 |
| Thr | Gln | Leu | Ser | Cys 350 | Ser | Gly | Asp | Gly | Phe 355 | Thr | Arg | Met | Lys | Lys 360 |
| Mrt | Lys | Leu | Pro | Glu 365 | Thr | Thr | Met | Ala | Thr 370 | Val | Asp | Arg | Ser | Ile 375 |
| Gly | Val | Lys | Glu | Cys 380 | Lys | Lys | Arg | Cys | Ile 385 | Ser | Asp | Cys | Asn | Cys 390 |
| Thr | Ala | Phe | Ala | Asn 395 | Ala | Asp | Ile | Arg | Asn 400 | Gly | Gly | Ser | Gly | Cys 405 |
| Val | Ile | Trp | Thr | Glu 410 | Arg | Leu | Glu | Asp | Ile 415 | Arg | Asn | Tyr | Ala | Thr 420 |
| Asp | Ala | Ile | Asp | Gly 425 | Gln | Asp | Leu | Tyr | Val 430 | Arg | Leu | Ala | Ala | Ala 435 |
| Asp | Ile | Ala | Lys | Lys 440 | Arg | Asn | Ala | Ser | Gly 445 | Lys | <u>Ile</u> | <u>Ile</u> | <u>Ser</u> | <u>Leu</u> 450 |
| <u>Thr</u> | <u>Val</u> | <u>Gly</u> | <u>Val</u> | <u>Ser</u> 455 | <u>Val</u> | <u>Leu</u> | <u>Leu</u> | <u>Leu</u> | <u>Leu</u> 460 | <u>Ile</u> | <u>Met</u> | <u>Phe</u> | <u>Cys</u> | <u>Leu</u> 465 |
| <u>Trp</u> | Lys | Arg | Lys | Gln 470 | Lys | Arg | Ala | Lys | Ala 475 | Ser | Ala | Ile | Ser | Ile 480 |
| Ala | Asn | Thr | Gln | Arg 485 | Asn | Gln | Asn | Leu | Pro 490 | Met | Asn | Glu | Met | Val 495 |
| Leu | Ser | Ser | Lys | Arg 500 | Glu | Phe | Ser | Gly | Glu 505 | Tyr | Lys | Phe | Glu | Glu 510 |
| Leu | Glu | Leu | Pro | Leu 515 | Ile | Glu | Met | Glu | Thr 520 | Val | Val | Lys | Ala | Thr 525 |
| Glu | Asn | Phe | Ser | Ser 530 | Cys | Asn | Lys | Leu | Gly 535 | Gln | Gly | Gly | Phe | Gly 540 |
| Ile | Val | Tyr | Lys | Gly 545 | Arg | Leu | Leu | Asp | Gly 550 | Lys | Glu | Ile | Ala | Val 555 |
| Lys | Arg | Leu | Ser | Lys 560 | Thr | Ser | Val | Gln | Gly 565 | Thr | Asp | Glu | Phe | Met 570 |
| Asn | Glu | Val | Thr | Leu 575 | Ile | Ala | Arg | Leu | Gln 580 | His | Ile | Asn | Leu | Val 585 |
| Gln | Val | Leu | Gly | Cys | Cys | Ile | Glu | Gly | Asp | Glu | Lys | Met | Leu | Ile |

| | | | | 590 | | | | | 595 | | | | | 600 |
|---|---|---|---|---|---|---|---|---|---|---|---|---|---|---|
| Tyr | Glu | Tyr | Leu | Glu 605 | Asn | Leu | Ser | Leu | Asp 610 | Ser | Tyr | Leu | Phe | Gly 615 |
| Lys | Thr | Arg | Arg | Ser 620 | Lys | Leu | Asn | Trp | Asn 625 | Glu | Arg | Phe | Asp | Ile 630 |
| Thr | Asn | Gly | Val | Ala 635 | Arg | Gly | Leu | Leu | Tyr 640 | Leu | His | Gln | Asp | Ser 645 |
| Arg | Phe | Arg | Ile | Ile 650 | His | Arg | Asp | Leu | Lys 655 | Val | Ser | Asn | Ile | Leu 660 |
| Leu | Asp | Lys | Asn | Met 665 | Ile | Pro | Lys | Ile | Ser 670 | Asp | Phe | Gly | Met | Ala 675 |
| Arg | Ile | Phe | Glu | Arg 680 | Asp | Glu | Thr | Glu | Ala 685 | Asn | Thr | Met | Lys | Val 690 |
| Val | Gly | Thr | Tyr | Gly 695 | Tyr | Met | Ser | Pro | Glu 700 | Tyr | Ala | Met | Tyr | Gly 705 |
| Ile | Phe | Ser | Glu | Lys 710 | Ser | Asp | Val | Phe | Ser 715 | Phe | Gly | Val | Ile | Val 720 |
| Leu | Glu | Ile | Val | Ser 725 | Gly | Lys | Lys | Asn | Arg 730 | Gly | Phe | Tyr | Asn | Leu 735 |
| Asp | Tyr | Glu | Asn | Asp 740 | Leu | Leu | Ser | Tyr | Val 745 | Trp | Ser | Arg | Trp | Lys 750 |
| Glu | Gly | Arg | Ala | Leu 755 | Glu | Ile | Val | Asp | Pro 760 | Val | Ile | Val | Asp | Ser 765 |
| Leu | Ser | Ser | Gln | Pro 770 | Ser | Ile | Phe | Gln | Pro 775 | Gln | Glu | Val | Leu | Lys 780 |
| Cys | Ile | Gln | Ile | Gly 785 | Leu | Leu | Cys | Val | Gln 790 | Glu | Leu | Ala | Glu | His 795 |
| Arg | Pro | Ala | Met | Ser 800 | Ser | Val | Val | Trp | Met 805 | Phe | Gly | Ser | Glu | Ala 810 |
| Thr | Glu | Ile | Pro | Gln 815 | Pro | Lys | Pro | Pro | Gly 820 | Tyr | Cys | Val | Arg | Arg 825 |
| Ser | Pro | Tyr | Glu | Leu 830 | Asp | Pro | Ser | Ser | Ser 835 | Trp | Gln | Cys | Asp | Glu 840 |
| Asn | Glu | Ser | Trp | Thr 845 | Val | Asn | Gln | Tyr | Thr 850 | Cys | Ser | Val | Ile | Asp 855 |
| Ala | Arg | | | | | | | | | | | | | |

In the preceding amino acid sequence, the putative signal peptide and transmembrane domain are underlined. The kinase subdomains, of which there are eleven, are shown extending from amino acid 523 to 814.

In addition, the amino acid sequence for the SRK2 coding region according to the present invention is: (SEQ. NO. 3)

| | | | | | | | | | | | | | | |
|---|---|---|---|---|---|---|---|---|---|---|---|---|---|---|
| Met | Lys | Gly | Val | Gln 5 | Asn | Ile | Tyr | His | His 10 | Ser | Tyr | Thr | Phe | Ser 15 |
| Phe | Leu | Leu | Val | Phe 20 | Leu | Val | Leu | Ile | Leu 25 | Phe | His | Pro | Ala | Leu 30 |
| Ser | Ile | Tyr | Val | Asn 35 | Thr | Leu | Ser | Ser | Ser 40 | Glu | Ser | Leu | Thr | Ile 45 |
| Ser | Ser | Asn | Arg | Thr 50 | Leu | Val | Ser | Pro | Gly 55 | Gly | Val | Phe | Glu | Leu 60 |
| Gly | Phe | Phe | Lys | Pro 65 | Leu | Gly | Arg | Ser | Arg 70 | Trp | Tyr | Leu | Gly | Ile 75 |
| Trp | Tyr | Lys | Lys | Ala | Pro | Trp | Lys | Thr | Tyr | Ala | Trp | Val | Ala | Asn |

-continued

|  |  |  |  |  | 80 |  |  |  |  | 85 |  |  |  | 90 |
|---|---|---|---|---|---|---|---|---|---|---|---|---|---|---|
| Arg | Asp | Asn | Pro | Leu 95 | Ser | Ser | Ser | Ile | Gly 100 | Thr | Leu | Lys | Ile | Ser 105 |
| Gly | Asn | Asn | Leu | Val 110 | Leu | Leu | Ser | Gln | Ser 115 | Thr | Asn | Thr | Val | Trp 120 |
| Ser | Thr | Asn | Leu | Thr 125 | Arg | Gly | Asn | Ala | Arg 130 | Ser | Pro | Val | Ile | Ala 135 |
| Glu | Leu | Leu | Pro | Asn 140 | Gly | Asn | Phe | Val | Ile 145 | Arg | His | Ser | Asn | Val 150 |
| Asn | Lys | Asp | Ser | Ser 155 | Gly | Phe | Leu | Trp | Gln 160 | Ser | Phe | Asp | Phe | Pro 165 |
| Thr | Asp | Thr | Leu | Leu 170 | Pro | Glu | Met | Lys | Leu 175 | Gly | Tyr | Asp | Leu | Lys 180 |
| Thr | Gly | Arg | Asn | Arg 185 | Phe | Leu | Thr | Ser | Trp 190 | Lys | Gly | Ser | Asp | Asp 195 |
| Pro | Ser | Ser | Gly | Asn 200 | Phe | Val | Tyr | Lys | Leu 205 | Asp | Ile | Arg | Arg | Gly 210 |
| Leu | Pro | Glu | Phe | Ile 215 | Leu | Ile | Asn | Gln | Phe 220 | Leu | Asn | Gln | Arg | Val 225 |
| Glu | Thr | Gln | Arg | Ser 230 | Gly | Pro | Trp | Asn | Gly 235 | Met | Glu | Phe | Ser | Gly 240 |
| Ile | Pro | Glu | Val | Gln 245 | Gly | Leu | Asn | Tyr | Met 250 | Val | Tyr | Asn | Tyr | Thr 255 |
| Glu | Asn | Ser | Glu | Glu 260 | Ile | Ala | Tyr | Ser | Phe 265 | His | Met | Thr | Asn | Gln 270 |
| Ser | Ile | Tyr | Ser | Arg 275 | Leu | Thr | Leu | Val | Ser 280 | Glu | Leu | Thr | Leu | Asp 285 |
| Arg | Leu | Thr | Trp | Ile 290 | Pro | Pro | Ser | Arg | Asp 295 | Trp | Trp | Ser | Leu | Phe 300 |
| Trp | Thr | Leu | Pro | Thr 305 | Asp | Val | Cys | Asp | Pro 310 | Leu | Tyr | Leu | Cys | Gly 315 |
| Ser | Tyr | Ser | Tyr | Cys 320 | Asp | Leu | Ile | Thr | Ser 325 | Pro | Asn | Cys | Asn | Cys 330 |
| Ile | Arg | Gly | Phe | Val 335 | Pro | Lys | Asn | Pro | Gln 340 | Gln | Trp | Asp | Leu | Arg 345 |
| Asp | Gly | Thr | Arg | Gly 350 | Cys | Val | Arg | Thr | Thr 355 | Gln | Met | Ser | Cys | Ser 360 |
| Gly | Asp | Gly | Phe | Leu 365 | Arg | Leu | Asn | Asn | Met 370 | Asn | Leu | Pro | Asp | Thr 375 |
| Lys | Thr | Ala | Thr | Val 380 | Asp | Arg | Thr | Met | Asp 385 | Val | Lys | Lys | Cys | Glu 390 |
| Glu | Arg | Cys | Leu | Ser 395 | Asp | Cys | Asn | Cys | Thr 400 | Ser | Phe | Ala | Ile | Ala 405 |
| Asp | Val | Arg | Asn | Gly 410 | Gly | Leu | Gly | Cys | Val 415 | Phe | Trp | Thr | Gly | Glu 420 |
| Leu | Val | Ala | Ile | Arg 425 | Lys | Phe | Ala | Val | Gly 430 | Gly | Gln | Asp | Leu | Tyr 435 |
| Val | Arg | Leu | Asn | Ala 440 | Ala | Asp | Leu | Asp | Ile 445 | Ser | Ser | Gly | Glu | Lys 450 |
| Arg | Asp | Arg | Thr | Gly 455 | Lys | Ile | Ile | Gly | Trp 460 | Ser | Ile | Gly | Ser | Ser 465 |
| Val | Met | Leu | Ile | Leu 470 | Ser | Val | Ile | Leu | Phe 475 | Cys | Phe | Trp | Arg | Arg 480 |

-continued

| | | | | | | | | | | | | | | |
|---|---|---|---|---|---|---|---|---|---|---|---|---|---|---|
| Arg | Gln | Lys | Gln | Ala 485 | Lys | Ala | Asp | Ala | Thr 490 | Pro | Ile | Val | Asn | Asn 495 |
| Gln | Val | Leu | Met | Asn 500 | Glu | Val | Val | Leu | Pro 505 | Arg | Lys | Lys | Arg | Asn 510 |
| Phe | Ser | Gly | Glu | Asp 515 | Asp | Val | Glu | Asn | Leu 520 | Glu | Leu | Pro | Leu | Met 525 |
| Glu | Phe | Glu | Ala | Val 530 | Val | Thr | Ala | Thr | Glu 535 | His | Phe | Ser | Asp | Phe 540 |
| Asn | Lys | Val | Gly | Lys 545 | Gly | Gly | Phe | Gly | Val 550 | Val | Tyr | Lys | Gly | Arg 555 |
| Leu | Val | Asp | Gly | Gln 560 | Glu | Ile | Ala | Val | Lys 565 | Arg | Leu | Ser | Glu | Met 570 |
| Ser | Ala | Gln | Gly | Thr 575 | Asp | Glu | Phe | Met | Asn 580 | Glu | Val | Arg | Leu | Met 585 |
| Gln | Ser | Phe | Ser | His 590 | Asn | Asn | Leu | Val | Arg 595 | Leu | Leu | Gly | Cys | Cys 600 |
| Val | Tyr | Glu | Gly | Glu 605 | Lys | Ile | Leu | Ile | Tyr 610 | Glu | Tyr | Leu | Glu | Asn 615 |
| Leu | Ser | Leu | Asp | Ser 620 | His | Leu | Asp | Glu | Thr 625 | Arg | Ser | Cys | Met | Leu 630 |
| Asn | Trp | Gln | Met | Arg 635 | Phe | Asp | Ile | Ile | Asn 640 | Gly | Ile | Ala | Arg | Gly 645 |
| Leu | Leu | Tyr | Leu | His 650 | Gln | Asp | Ser | Arg | Phe 655 | Arg | Ile | Ile | His | Arg 660 |
| Asp | Leu | Lys | Ala | Ser 665 | Asn | Val | Leu | Leu | Asp 670 | Lys | Asp | Met | Thr | Pro 675 |
| Lys | Ile | Ser | Asp | Phe 680 | Gly | Met | Ala | Arg | Ile 685 | Phe | Gly | Arg | Asp | Glu 690 |
| Thr | Glu | Ala | Asp | Thr 695 | Arg | Lys | Val | Val | Gly 700 | Thr | Tyr | Gly | Tyr | Met 705 |
| Ser | Pro | Glu | Tyr | Ala 710 | Met | Asn | Gly | Thr | Phe 715 | Ser | Met | Lys | Ser | Asp 720 |
| Val | Phe | Ser | Phe | Gly 725 | Val | Ile | Leu | Leu | Glu 730 | Ile | Ile | Ser | Gly | Lys 735 |
| Arg | Asn | Lys | Gly | Leu 740 | Cys | Asp | Leu | Asp | Ser 745 | Ser | Leu | Asn | Leu | Leu 750 |
| Gly | Cys | Val | Trp | Arg 755 | Asn | Trp | Lys | Glu | Gly 760 | Gln | Gly | Leu | Glu | Ile 765 |
| Val | Asp | Lys | Val | Ile 770 | Ile | Asp | Ser | Ser | Ser 775 | Pro | Thr | Phe | Arg | Pro 780 |
| Arg | Glu | Ile | Leu | Arg 785 | Cys | Leu | Gln | Ile | Gly 790 | Leu | Leu | Cys | Val | Gln 795 |
| Glu | Arg | Val | Glu | Asp 800 | Arg | Pro | Met | Met | Ser 805 | Ser | Val | Val | Leu | Met 810 |
| Leu | Gly | Ser | Glu | Ala 815 | Ala | Leu | Ile | Pro | Gln 820 | Pro | Lys | Gln | Pro | Gly 825 |
| Tyr | Cys | Val | Ser | Gly 830 | Ser | Ser | Leu | Glu | Thr 835 | Tyr | Ser | Arg | Arg | Asp 840 |
| Asp | Glu | Asn | Cys | Thr 845 | Val | Asn | Gln | Ile | Thr 850 | Met | Ser | Ile | Ile | Asp 855 |
| Ala | Arg | | | | | | | | | | | | | |

This amino acid sequence corresponds, in part, to the following predicted sequence of the SRK$_2$ coding region determined by the removal of putative promoter and intron sequences from the sequence of the SRK$_2$ gene which included all exons and introns (SEQ. NO. 4). Thus, the initial 2571 nucleotides in the following nucleic acid sequence, the structural gene, was used to determine the polypeptide sequence given above.

| | | | | | | | | | | | | | | | | |
|---|---|---|---|---|---|---|---|---|---|---|---|---|---|---|---|---|
| ATG | AAA | GGG | GTA | CAG | AAC | ATT | TAC | CAC | CAT | TCT | TAC | ACC | TTC | TCG | TTC | TTG | 51 |
| CTA | GTC | TTC | CTT | GTC | TTG | ATT | CTA | TTT | CAT | CCT | GCC | CTT | TCG | ATC | TAT | GTC | 102 |
| AAC | ACT | TTA | TCG | TCT | TCA | GAG | TCT | CTC | ACA | ATC | TCG | AGC | AAT | AGA | ACA | CTT | 153 |
| GTA | TCT | CCC | GGT | GGA | GTC | TTC | GAG | CCT | GGT | TTC | TTC | AAA | CCC | TTG | GGA | CGC | 204 |
| TCG | CGA | TGG | TAT | TAT | GGA | ATA | TGG | TAT | AAA | AAA | GCC | CCC | TGG | AAA | ACC | TAC | 255 |
| GCA | TGG | GTC | GCC | AAC | AGA | GAC | AAC | CCT | TCC | AGT | GCC | TCT | ATT | GGA | ACC | CTC | 306 |
| AAA | ATC | TCT | GGC | AAT | AAT | AAT | CTT | AGT | CTA | CAG | TCT | TCT | ACT | AAC | ACT | GTT | 357 |
| TGG | TCG | ACA | AAT | CTT | ACT | ACT | AGA | GCG | CCG | AGA | GCG | CCG | GTG | ATA | GCA | GAG | 408 |
| CTT | CTT | CCC | AAC | GGT | AAT | AAT | TTT | ATT | CAC | TCC | ACA | AAC | AAC | AAA | TTA | TCA | 459 |
| AGT | GGA | TTC | TTG | CAG | AGT | AGT | CCG | TTT | AGA | CCG | CCG | GAT | ACT | AGG | TTT | CCG | 510 |
| GAG | ATG | AAA | CTA | GGT | TAC | GAT | GAT | CTC | AAA | GGG | CGC | AAT | AGG | GTG | CTT | ACA | 561 |
| TCG | TGG | AAA | AGG | TCA | GAT | TTG | CCT | TCA | TTT | AGC | AAT | TCA | GTG | TAC | TTC | CTC | 612 |
| GAC | ATT | CGA | GAA | GGA | TTG | CCT | GAG | ATT | TTT | CTT | ATA | AAT | CAA | TTT | GAG | AAT | 663 |
| CAA | CGT | GTT | GAG | ACG | CAA | AGC | GAG | CCT | TGG | GGT | AAT | AAT | ATG | TTT | AGT | AGT | 714 |
| GGC | ATA | CCG | GAG | GTG | CGG | TTA | TCG | TAC | ATG | TAC | GTT | GGA | ATT | TAT | AGC | GAG | 765 |
| AAC | AGT | GAG | GAG | ATC | GTC | GCT | AGT | GAG | TCG | CAT | ATG | ACC | CAA | CAA | ATC | TAC | 816 |
| TCC | AGA | ACA | GAC | GTG | AGC | GGA | CGG | CGG | CTA | CTC | GAT | TTA | ACG | TTG | ATC | CCG | 867 |
| CCA | TCA | CGG | GAT | TTA | GGA | TGG | TGT | CTT | ACT | CCA | GAC | GAC | GTG | ACG | TGC | GAT | 918 |
| CCG | CTT | TAC | TTA | AGC | AGA | TCT | TAT | GTT | TAC | TGT | AAG | AAC | CAG | ATT | TCA | CCT | 969 |
| AAC | AAC | GAC | TGT | ATT | ACA | GGA | TGT | GTG | AGG | AGG | ATG | ACG | ACG | CAG | ATG | GAC | 1020 |
| TTG | AGA | GGA | GGA | ACA | CGG | GGA | CTA | ATG | AAT | AGG | AGC | AGC | ATG | AGC | TGT | AGT | 1071 |
| GGA | GAC | TTT | GAT | CGG | ACA | ATG | GAT | GTG | AAT | GTG | TTG | CCG | GAT | GAT | ACT | ACG | 1122 |
| GCA | ACT | GTG | AAC | TGT | ACT | CTG | ACA | ATT | AAA | GCG | TGT | GAC | GCG | CAG | GAA | CTT | 1173 |
| AGC | GAT | TGT | AAC | TGT | GGT | AAT | ATT | GCT | CTC | GTT | GAT | GCG | ATC | TTC | GGA | 1224 |
| TTG | GGT | TGT | GTG | TTT | TGG | ACT | GAG | CTC | AGG | AGG | CCG | GGA | GGA | ATT | FFC | 1275 |
| GTC | GGT | GGT | CAA | GAT | CTT | AAT | TAC | TTG | AGA | TTG | CTA | GCT | GAT | ATT | 1326 |

-continued

| | | | | | | | | | | | | | | | | | |
|---|---|---|---|---|---|---|---|---|---|---|---|---|---|---|---|---|---|
| TCC | TCG | GGT | GAG | AAG | AGA | GAC | CGA | ACT | GGA | AAA | ATC | ATA | GGT | TGG | AGT | ATT | 1377 |
| GGA | TCC | AGC | GTT | ATG | CTT | ATT | CTG | AGT | GTT | ATC | TTG | TTC | TGC | TTT | TGG | AGG | 1428 |
| AGG | AGA | CAA | AAG | CAA | GCA | AAA | GCA | GAT | GCA | ACA | CCT | ATT | GTG | GGA | AAT | CAA | 1479 |
| GTT | CTA | ATG | AAC | GAG | GTG | GTG | TTA | CCA | AGA | AAG | CCT | AGA | AAT | TCT | AAT | TTT | 1530 |
| GAG | GAC | GAT | GTA | GAA | AAT | TTG | GAA | CTT | GAT | TTT | CCA | ATG | AAG | GAG | GCT | GAA | 1581 |
| GTC | ACA | GCC | ACC | GAA | CAT | TTC | TCT | GAT | TTT | CCA | AAC | AAG | GGG | TGC | GGA | GGT | 1632 |
| TTT | GGT | GTT | GTT | TAC | AAG | GGA | AGG | TTA | GGT | AAT | GTT | GAC | GAA | CAA | GAA | GTG | 1683 |
| AAG | AGA | CTA | TCG | GAA | ATG | GCT | AGC | CAA | GGT | ACC | ATT | GAG | TTC | ATG | AAC | GAA | 1734 |
| GTT | AGG | CTA | ATG | CAA | AGC | TTC | AGC | CAC | AAT | CTT | CAC | CTT | CGA | GTC | CTT | GGC | 1785 |
| TGT | TGT | GTT | TAT | GAG | GGC | GAG | CTC | TAC | ATT | ACC | AAA | TAC | GAG | TAC | GAG | AAT | 1836 |
| CTA | AGC | CTC | GAT | AGA | CAT | TTT | ATC | GAT | AAT | GGT | ACC | AGA | AGC | CGA | CTC | TAT | 1887 |
| TGG | CAA | ATG | AGA | TTT | TCT | AGT | ATC | AGA | GGT | ATT | GCC | CGA | CTC | CTC | GCA | AGC | 1938 |
| CTT | CAC | CAA | GAT | TCA | TCA | TTT | ATC | TTT | TTT | CAT | AAA | AGG | GAT | TTG | AAA | ATG | 1989 |
| AAT | GTC | TTG | CTT | GAT | AAA | CGG | ATT | GAT | CCA | ACT | CCA | AAA | ATT | TTT | GAC | ATG | 2040 |
| GCT | AGG | ATC | TTT | GGA | CGG | GAT | GAG | GCT | GAC | ACG | GAA | GCT | AAC | GAG | AGG | GTC | 2091 |
| GGA | ACT | TAT | GGC | TAC | ATG | TCT | AGT | CCA | TAT | GGG | GAA | TAT | ATG | GGG | TTC | ATA | 2142 |
| ATG | AAG | GTG | TTC | TTG | GTT | GGG | CTT | CTT | GTC | CGT | AAC | CTT | GAA | ATA | CTT | TCA | 2193 |
| GGC | AGG | AAA | AGG | GGC | AAT | GCG | TCG | TGC | AAA | AGT | GGA | CTT | AGC | CTA | CTT | AGT | 2244 |
| GGA | TGT | GTA | TGG | AGG | GAT | TTA | GGT | ACG | TTC | GGA | AGC | GTG | AGT | CAA | GTA | CTC | 2295 |
| AAG | GTC | ATA | CAA | AGG | ATT | GAT | CTC | TGT | ATG | AGT | GGA | GAA | AGT | AAT | ATC | GAC | 2346 |
| AGA | ACT | TAT | TTA | CAA | GAC | TAA | GTA | AGT | GTT | CTT | TCT | TAT | CAA | TAT | GAT | TTA | 2397 |
| CCA | AAG | CCT | AGG | TCG | AAA | CAG | GAC | CGG | CCA | TGT | CTC | GTC | ACA | GCA | TTG | AGA | 2448 |
| CCT | CAA | CAA | GTA | AGG | AGC | GAT | TAA | GAA | AAT | GGA | AAC | GTG | GGA | AGC | GCA | CTT | 2499 |
| TAT | TCT | CCT | CGT | GCT | AAA | TAT | GAT | CGG | CAA | ACC | ATA | TAT | TCT | ACC | ATG | GAC | 2550 |
| ATC | ATT | GAC | ACT | AGG | CGT | AAA | AGA | ATT | TAA | GTT | TCT | TCT | TGA | CAC | TAT | TTA | 2601 |
| AGT | TTT | ACT | TCT | TGG | AAA | GAT | AGA | AAT | AGA | TGA | CAA | TCA | AGC | CAA | AGC | AGA | 2652 |
| CCA | AAC | TCT | TCA | GTC | TAT | CGA | AAT | TTT | TCA | TCA | GTA | TAT | TCT | CTC | GTG | 2703 |

-continued

| GAA | TTG | GTT | TCG | TTA | TTT | CGA | GTC | AAT | TCA | CAG | TCA | ACA | ACT | GCA | G | 2749 |

As many of the recombinant DNA techniques employed in this invention are a matter of routine for the person skilled in the art, it is better to give a short description of these generally used techniques here rather than to describe them every time they occur. Except where there is a specific indication to the contrary, all these procedures are described in the Maniatis et al (1982) reference.

A. Cleaving With Restriction Endonucleases.

A reaction batch typically contains about 50 to 500 µg/ml Of DNA in the buffer solution recommended by the manufacturer, New England Biolabs, Beverly, Mass. 2 to 5 units of restriction endonucleases are added for each I-Lg Of DNA and the reaction batch is incubated for from one to three hours at the temperature recommended by the manufacturer. The reaction is terminated by heating at 65° C. for 10 minutes or by extraction with phenol, followed by precipitation of the DNA with ethanol. This technique is also described on pages 104 to 106 of the Maniatis reference.

B. Treatment of the DNA With Polymerase in Order to Produce Blunt ends:

50 to 500 µg/ml of DNA fragments are added to a reaction batch in the buffer recommended by the manufacturer (New England Biolabs). The reaction batch contains all four deoxynucleotide triphosphates in concentrations of 0.2 mM. The reaction takes place over a period of 30 minutes at 15° C. and is then terminated by heating at 65° C. for 10 minutes. For fragments obtained by cleaving with restriction endonucleases that produce 5'-projecting ends, such as EcoRI and BamHI, the large or Klenow fragment of DNA polymerase is used. For fragments obtained by means of endonucleases that produce 3'-projecting ends, such as PstI and SacI, the T4-DNA polymerase is used. The use of these two enzymes is described on pages 113 to 121 of the Maniatis reference.

C. Agarose Gel Electrophoresis and Purification of DNA Fragments from Gels:

Agarose gel electrophoresis is carried out in a horizontal apparatus, as described on pages 150 to 163 of the Maniatis reference. The buffer used is the Tris-borate buffer described therein. The DNA fragments are stained using 0.5 mg/ml of ethidium bromide which is either present in the gel or tank buffer during electrophoresis or is added after electrophoresis. The DNA is made visible by illumination with long-wave ultraviolet light. If the fragments are to be separated from the gel, an agarose is used that gels at low temperature and is obtainable from Sigma Chemical, St. Louis, Mo. After the electrophoresis the desired fragment is cut out, placed in a plastics test tube, heated at 65° C. for about 15 minutes, extracted three times with phenol and precipitated twice with ethanol. As an alternative, the DNA can be isolated from the agarose with the aid of the Geneclean™ kit (Bio 101 Inc., La Jolla, Calif.).

D. Addition of Synthetic Linker Fragments to DNA Ends:

If it is desired to add a new endonuclease cleavage site to the end of a DNA molecule, the molecule is optionally first treated with DNA-polymerase in order to produce blunt ends, as described in the above section. About 0.1 to 1.0 µg of this fragment is added to about 10 ng of phosphorylated linker DNA (New England Biolabs) in a volume of 20 to 30 µl with 2 ILl of T4 DNA ligase (New England Biolabs), and 1 mM ATP in the buffer recommended by the manufacturer.

After incubation overnight at 15° C., the reaction is terminated by heating at 65° C. for 10 minutes. The reaction batch is diluted to about 100 µl in a buffer appropriate for the restriction endonuclease that cleaves the synthetic linker sequence. About 50 to 200 units of this endonuclease are added. The mixture is incubated for 2 to 6 hours at the appropriate temperature, then the fragment is subjected to agarose gel electrophoresis and purified as described above. The resulting fragment will then have ends with endings that were produced by cleaving with the restriction endonuclease. These ends are usually cohesive, so that the resulting fragment can then readily be linked to other fragments having the same cohesive ends.

E. Removal of 5'-Terminal Phosphates from DNA Fragments:

During the plasmid cloning steps, the treatment of the vector plasmid with phosphatase reduces the recircularisation of the vector (discussed on page 13 of Maniatis). After cleavage of the DNA with the correct restriction endonuclease, one unit of calf intestinal alkaline phosphatase (Boehringer-Mannheim) is added. The DNA is incubated at 37° C. for one hour and then extracted twice with phenol and precipitated with ethanol.

F. Linking of the DNA Fragments:

If fragments having complementary cohesive ends are to be linked to one another, about 100 ng of each fragment are incubated in a reaction mixture of 20 to 40 µl containing about 0.2 unit of T4 DNA ligase (New England Biolabs) in buffer recommended by the manufacturer. Incubation is carried out for 1 to 20 hours at 15° C. If DNA fragments having blunt ends are to be linked, they are incubated as above except that the amount of T4 DNA ligase is increased to 2 to 4 units.

G. Transformation of DNA into *E. coil:*

*E. coil* strain HB101 is used for most of the experiments. DNA is introduced into E. coil using the calcium chloride process, as described by Maniatis on pages 250 and 251.

H. Screening of *E. coil* for Plasmids:

After transformation, the resulting colonies of *E. coli* are tested for the presence of the desired plasmid by means of a rapid plasmid isolation process. Two customary processes are described on pages 366 to 369 of the Maniatis reference.

I. Large-Scale Isolation of Plasmid DNA:

Processes for the isolation of plasmids from E. coil on a large scale are described on pages 88 to 94 of the Maniatis reference.

J. Cloning in M13 Phage Vectors:

In the following description it is to be understood that the double-strand replicative form of the phage M13 derivatives is used for routine processes, such as cleaving with restriction endonuclease, linking etc..

Unless there is a specific indication to the contrary, enzymes can be obtained from either Boehringer or Biolabs (BRL), and are used in accordance with the manufacturer's instructions unless otherwise indicated.

K. Southern Blot Analysis:

The extracted DNA is first treated with restriction enzymes, then subjected to electrophoresis in a 0.8% to 1% agarose gel, transferred to a nitrocellulose membrane and hybridized with the DNA to be detected which has previously been subjected to nick-translation (DNA-specific activities of $5 \times 10^8$ to $10 \times 10^8$ C.p.m./µg). The filters are washed three times for 1 hour each time with an aqueous solution of 0.03 M sodium citrate and 0.3 M sodium chloride at 65° C. The hybridized DNA is made visible by blackening an X-ray film over a period of 24 to 48 hours.

L. Western Blot Analysis:

After SDS-polyacrylamide gel electrophoresis, the proteins are transferred electrophoretically to a nitrocellulose or nylon filter. This filter is then pretreated with a blocking agent (for example 5% skim milk powder in PBS: in the following referred to as milk/PBS). The filter is then incubated for several hours with an antiserum that reacts with the compound to be detected. The filter pre-treated in this manner is washed several times with milk/PBS and then incubated with a commercially available secondary antibody that is coupled to an enzyme [for example peroxidase-coupled goat anti-rabbit antibody (BIORAD), 1:2000 diluted in milk/PBS]. The filter is again washed in PBS and then stained with chloronaphthol and hydrogen peroxide in accordance with the manufacturer's [BIORAD] instructions.

M. Northern Blot Analysis:

Total RNA can be prepared in accordance with the method described in Logemann et al (1987), but it is advantageous to introduce an additional precipitation step with 2 M LiCl in order to eliminate any residues of contaminant DNA. The RNA (0.4 mg or 4 mg) is then fractionated by electrophoresis in a 1% agarose gel containing 6.7% formaldehyde, The individual fractions are transferred to Zeta-Probe™ membranes [BIORAD] and hybridized with a 32P-labelled probe. The size of the hybridizing DNA can be estimated by reference to the standard run at the same time.

As described in greater detail in the following description, the structure of $SRK_6$ was determined by sequencing both strands of 4.8 kb genomic fragment and 3 overlapping $S_6S_6$ stigma cDNA clones, pS6–27 (1105 bp), pS6–32(686 bp), and pJS30 (1566 bp) (FIG. 2A). Comparison of the genomic and cDNA sequences revealed 7 exons interspaced with 6 introns ranging in size from 76 bp (intron 3) to 898 bp (intron 1). The coding region (FIG. 2B) has a single open reading frame that predicts a protein of 857 amino acids. Two alternative polyadenylation sites generate a 3' non-coding region of either 192 bp or 261 bp.

The predicted $SRK_6$ polypeptide (98,071 daltons) consists of several domains. Each domain is encoded by separate exons or groups of exons, consistent with the view that multi-domain proteins evolved by exon-shuffling. The 437 amino acid region encoded by exon 1 defines the "S" domain" which is highly similar to $SLG_6$. The hydrophobic residues (–32 to –1) at the N-terminus constitute a putative signal peptide that is 67% identical to the signal sequence of $SLG_6$ (FIGS. 2B & 3). The rest of the "S" domain (residues 1–406) is 89% identical to SLG6, and contains a cluster of 12 cysteine residues, a hallmark of the S-multigene family. Exon 2 encodes a 20 amino acid hydrophobic stretch (residues 415–434) that is likely to form a membrane spanning helix. As is typical of transmembrane domains, of the 8 amino acids that follow this region are basic. The remaining sequence, encoded by exons 3–7, contains a putative protein kinase catalytic domain (residues 489–781) that is flanked by a 55 amino acid juxtamembrane domain and a 44 amino acid carboxy-terminus domain. A diagnostic feature of protein kinases is the presence of 11 conserved subdomains wherein lie 15 invariant or nearly invariant amino acid residues. These subdomains as well as all 15 conserved residues were identified in the predicted protein sequence of $SRK_6$ (FIGS. 2B & 3). The substrate specificity of protein kinases, either serine/threonine or tyrosine, generally correlates with consensus sequences within subdomains VI and VII. The $SRK_6$ sequence in subdomains VI (Asp-Leu-Lys-Val-Ser-Asn) (SEQ. NO. 5) and VIII (Gly-Thr-Tyr-Gly-Tyr-Met-Ser-Pro-Glu) (SEQ No. 6) agrees strongly with the consensus for the serine/threonine kinases. A database search with the $SRK_6$ polypeptide sequence revealed greatest similarity, after SLG, to maize ZmPK1, showing conservation with both the "S" domain (29% identity) and the kinase domain (36% identity). Significant similarity was also found with the catalytic domains of other protein kinases, particularly those of tyrosine kinases and the raf serine/threonine kinase.

These results suggest that $SRK_6$ encodes an integral membrane protein. The "S" domain plus 9 residues encoded by exon 2 would be located extracellularly, and the putative kinase domain and flanking regions would be oriented toward the cytoplasm. Of 10 potential N-glycosylation sites (N-X-S/T), 7 would occur extracellularly (FIG. 2B), and 5 of these are conserved with the 9 sited in $SLG_6$. This structure is similar to receptor tyrosine kinases, which have a glycosylated extracellular domain responsible for ligand-binding, a single-pass transmembrane domain, and an intracellular tyrosine kinase catalytic domain. The existence of receptors with possible serine/threonine kinase specificity has only recently been suggested by the description of ZmPK1, the *Caenorhabditis elegans* daf-1 gene, and the SRK gene reported here. However, sequence-based predictions of kinase substrate specificity can be misleading, and only direct biochemical evidence will determine whether these genes represent a new class of receptor kinases.

The Brassica oleracea plants used in the making of the present invention were inbred lines homozygous for the $S_2$, $S_6$ and $S_{14}$ self-incompatibility alleles. The $S_6$ homozygote belonged to the variety acephala (kale) and was derived from plant material initially obtained from the Gene Bank Facility at Wellesbourne. The $S_{14}$ homozygote was developed at Cornell University and belonged to the variety capitata (cabbage). Because the ability of stigmas to distinguish self pollen occurs late in development, immature bud stigmas are self-compatible. By self-pollinating these compatible immature stigmas, these self-incompatible lines were able to be produced and maintained. The $S_2$ homozygote, as well as the two others mentioned, have been described in the literature [see Nature 326:617 (1987) and Mol. Gen. Genet. 222:241 (1990).

While the following examples illustrate the present invention with respect to the $SRK_6$ and $SLG_6$ genes, the present invention can also be practiced by one skilled in the art with other self-incompatible plants wherein self-incompatibility is determined by an S-locus, which preferably includes both an SLG and an SRK gene. For example, the present invention can be readily practiced with respect to plants utilizing genes isolated from the $S_2$, $S_6$, $S_{13}$, $S_{16}$ and $S_{22}$ alleles of Brassica and related genera.

The $S_6$ homozygous plant was selected as a source of DNA for the present invention, and large quantities of genomic DNA were purified from the $S_6$ homozygous plant according to a procedure modified from Bingham et al [see Cell 25:693 (1981)] and described in the following Example 1.

EXAMPLE 1

Isolation of DNA From $S_6$ Homozygote

Approximately 10 g of young, healthy leaf tissue was frozen in liquid nitrogen and ground by hand in a prechilled mortar and pestle. The ground powder was suspended in 30 ml of ice-cold nuclear isolation buffer comprising 10 mM Tris pH 7.4, 60 mM NaCl, 10 mM EDTA, 0.15 mM spermidine, 0.15 mM spermine, 0.5% (v/v) Triton X-100 and 958 ml water. The suspended mixture was homogenized at medium speed in a motor-driven teflon pestle and homogenizer up and down 10 times. To remove large debris, the homogenate was transferred to a 50 ml polypropylene tube and subjected to 1500 rpm centrifugation in a Beckman J-6B centrifuge for 30 seconds at 4° C. The supernatant was removed to a clean 50 ml tube and nuclei were pelleted by centrifugation at 7,000 RPM for 7 min. at 4° C. in an SS34 rotor. After discarding the supernatant, the white nuclei-containing pellet was washed in 20 ml of the nuclear isolation buffer and repelleted by centrifugation as above. The resulting pellet was resuspended in 5 ml of the nuclear isolation buffer, followed by the addition of 1 ml 10% Sarkosyl and gently mixed several minutes on ice to lyse the nuclei; as the nuclei are lysed, the solution becomes quite viscous. CsCl (11.17 g) was dissolved into the lysed nuclei after which the volume was adjusted to 12 ml with additional nuclear isolation buffer [25 ml nuclear isolation buffer; 5 ml 10% Sarkosyl (3.33 ml 10% stock+6.67 ml water), 60.5 g CsCl, to 65 ml with nuclear isolation buffer): 10% Sarkosyl (5:1), and mixed at room temperature until the CsCl dissolved completely. Insoluble debris was removed following centrifugation at 2000 rpm/10 min./room temperature.

In order to visualize nucleic acids, 3.5 gl 10 mg/ml EtBr was added. The mixture was transferred to a 13 ml ultracentrifuge tube, sealed, and subjected to a centrifugation at 47,000 rpm/15° C./18 hours. This centrifugation created a CsCl density gradient within the tube causing the genomic DNA to form a distinct band that was free from the bulk of the macromolecules, such as RNA and protein. The DNA band was removed using a hypodermic needle and the CsCl centrifugation was repeated in order to further remove contaminants. Final purification of DNA was achieved after dialysis against several changes of TE buffer (10 mM Tris pH 8.0, 1 ml EDTA). Approximately 200 µg of genomic DNA was purified in this way, as determined by spectrophotometry at 260 nM. Utilizing the genomic DNA purified from the $S_6$ homozygous plant according to Example 1, an $S_6$ genomic DNA library was constructed in a λ vector according to the following Example II.

EXAMPLE II

Library Construction and Screening of $S_6$ DNA and Cloning of $SRK_6$ Gene One hundred micrograms of the purified nuclear DNA made in accordance with Example 1 was partially digested utilizing known techniques with the restriction enzyme Sau 3A, and the fragments were size-fractionated by salt centrifugation on salt gradients according to the procedures of Liu et al [see Science 209:1348 (1980)]. DNA in the 10 to 20 kilobase fraction was ligated to Bam HI-digested EMBL4 DNA, and the ligated DNA was packaged in vitro using Gigapack extracts (Stratagene). The packaged bacteriophage library was used further to infect lawn cultures of *Escherichia coil* host Q359, and incubated at 37° C. These conditions favor lysis of host cells and the formation of plaques, each of which are derived from an individual recombinant phage clone.

In order to determine which recombinant phage clones carried genomic regions corresponding to SLG-homologous genes, plaques were transferred to nitrocellulose membranes and hybridized with the $^{32}$P-labelled $SLG_6$-cDNA insert from pBOS6 described by Nasrallah et al [see Nature 326:6113 (1987)] under conditions described by Maniatis [see Molecular cloning: a laboratory manual, Cold Spring Harbor Laboratory Press, Cold Spring Harbor, N.Y. (1982)]. A total of $10^6$ recombinant phage were screened, and of these 77 hybridized to the probe. These SLG homologous clones were purified and their DNA isolated according to the method of Thomas and Davis [see J Mol Biol 91:315 (1975)].

Each cloned insert made in accordance with Example II was characterized by restriction mapping using a wide variety of enzymes; since each restriction enzyme cleaves DNA at specific sequences, unique regions within the nuclear genome have a characteristic distribution of restriction enzyme cleavage sites. These restriction maps were used to place the recombinants into groups of overlapping clones. Several distinct regions of the Brassica genome were identified in this manner. Of the 77 clones analyzed, nine overlapped one another and corresponded to the $SRK_6$ gene.

One of the homologous $SRK_6$ clones contained a 5.8 kb insert which was designated as 281. This insert was subcloned into the pUC13 vector according to the following example:

EXAMPLE III

Sequencing of the $SRK_6$ Gene

Ten ILl Of purified phage DNA containing the 281 insert was digested with Eco RI and the released 5.8 kb insert was purified after submitting the digested DNA to 1% agarose gel electrophoresis. The purified 5.8 kb fragment was cloned into an Eco RI digested plasmid vector using T4 ligase. The resulting ligated mixture was transformed into competent DH5α cells and plated onto LB-Amp media. Transformed cells harboring the recombinant 281-containing plasmid were selected and purified. This plasmid, p281, was used in all subsequent experiments. The plasmid has been deposited under the Budapest Treaty with the American Type Culture Collection, has been accepted and has received accession number 75036.

In order to sequence the insert of p281, the dideoxy method was utilized. All necessary components of the sequencing reactions, except for the template DNA being sequenced, were supplied by commercially available sequencing kits (Pharmacia). Overlapping subclones of 281 were constructed in order to obtain suitable template DNA for sequence reactions. This was accomplished by digesting p281 with enzymes corresponding to sites within 281. The following restriction enzyme sites were utilized: Bgl II, Hinc II, Xba I, Xho I, Pst I, Sal I, Asu II, and Hind III. The resulting overlapping fragments generated by these enzymes were individually subcloned into the pBluescript plasmid vector (Stratagene), and the resulting plasmids were used as sequencing templates. Additional subclones were generated using the Exo III nested deletion method. A 3.7 kb Sail fragment corresponding to the 3' end of the S domain and all of the kinase domain was subcloned into the pUC119 plasmid vector. The resulting plasmid, p281S, was subjected to Exo III digestion from the 5' end of the gene, using the Erase-a-Base™ kit (Promega) based upon the procedure developed by Heinkoff [see Gene 28:351 (1984)].

Following re-ligation, the mixed population of partially deleted plasmids were transformed into DH5α *E. coil* cells. Twenty colonies were selected that harbored plasmids with partially deleted 281 fragments. These were designated p281S-A to p281S-T. Together, the deletions spanned approximately 3 kb. Templates prepared from the above subclones were sequenced using the commercially available Universal or Reverse primers, which bind to vector sites adjacent to the inserted 281 DNA. In order to prime sequencing reactions at sites within 281, 29 oligonucleotides (17–22 mer) were synthesized. These oligonucleotides bind to regularly spaced sites (approximately 200 bp apart) along the length of the $SRK_6$ gene within 281. Template DNA suitable for sequencing reactions were prepared from plasmid minipreps using the following protocol:

After growing overnight, a 5 ml culture of cells was centrifuged at 2,000 rpm for 10 min in a Sorvall centrifuge to pellet the cells. The supernatant was poured off and the pellet resuspended in 0.7 mls of cold STET, pH 8.0 (8% sucrose, 5% TX100, 50 mM EDTA at pH 8.0, and 50 mM Tris at pH 8.0) buffer. Fifty µl of 5 mg/ml lysozyme solution (100 mg lysozyme, 5 ml Tris at pH 8.0, 15 mls of distilled water) was added to the resuspended cells, the mixture transferred to a microfuge tube, and the tube boiled for 45 seconds to lyse the cells. The lysed cells were spun to pellet the cellular mixture, and the pellet was removed. An equal volume (about 0.5 mls) of isopropanol was added, the contents were mixed by inversion, and the tube placed in a −20° C. freezer for 30 minutes. After removing the tube from the freezer, it was spun for 10 minutes to form a pellet, the pellet was rinsed with 1 ml of 95% ethanol, and any fluids were removed by vacuum drying. The dried powder was resuspended in 75 µl of TE (10 mM Tris at pH 7.5, and 1 mM EDTA at pH 8.0) within an ice bath.

EXAMPLE IV

Determination of Linkage of SRK Gene To The S Locus: Genetic Segregation of RFLP Markers DNA gel blot hybridization was performed using DNA isolated from the $S_6$ and $S_{14}$ homozygotes by centrifugation of leaf nuclear DNA as described Example 1. DNA was isolated from $F_2$ progeny plants by a DNA minipreparation procedure based upon a rapid phage DNA extraction method according to the following protocol:

Approximately 0.25 g of leaf tissue harvested from an actively growing young vegetative bud was frozen in liquid nitrogen, and the frozen tissue was pulverized at liquid nitrogen temperature in an Eppendorf tube (1.5 ml) with a Kontes Eppendorf pestle. 400 µl of grind buffer (4 parts homogenization buffer:1 part phage lysis buffer) held at 65° C. was added and the mixture homogenized briefly without foaming. Homogenization buffer consists of 0.1 M NaCl, 0.2 M sucrose, 0.01 M EDTA, and 0.03 M Tris-HCl at pH 8.0; phage lysis buffer consists of 0.25 M EDTA, 2.5% (w/v) SDS, and 0.5 M Tris-HCl at pH 9.2. The suspension was next incubated in a 65° C. water bath for approximately 30 min., and 133 µl of 3 M potassium acetate buffer at pH 4.7 was added. The suspension was incubated on ice approximately 30 minutes and spun in a microfuge for 10 min., and the supernatant transferred to a new Eppendorf tube. 700 l of ethanol was added and the tube left at room temperature for 2 min., followed by centrifugation in a microfuge for 10 min. The pellet was washed in cold 70% ethanol, recentrifuged, and the washing step repeated. The pellet was then dried in a roto-vac, dissolved in 40 µl of water, and 1 µl of a DNase-free RNase solution (10 µg/ml) added.

Either 10 g of CsCl purified DNA or the amount of minipreparation DNA extracted from 300 mg of leaf tissue was restricted with Eco RI. Restriction fragments were fractionated on 0.9% agarose gels and transferred (Southern blots) to GeneScreenPlus™ membranes (DuPont-New England Nuclear). The membranes were prehybridized at 65° C. in a solution of 10% dextran sulfate (wt/vol), 330 mM sodium phosphate at pH 7.0, 10 mM EDTA/5% (w/v), $NaDodSO_4$, and denatured salmon sperm DNA at 100 µg/ml. Two different $^{32}P$-labelled probes prepared by the random primed labelling reaction of Feinberg and Vogelstein [see Anal Blochem 132:6 (1983), and Anal Blochem 137:266 (1984)] were used: (i) a probe specific for the SLG gene and derived from the 3' untranslated region of SLG6 cDNA [see PNAS, USA 85:5551 (1988)]; and (ii) a probe specific for the $SRK_6$ gene. The membranes were washed at 65° C. in a solution of 0.3 M sodium chloride, 40 mM Tris-HCl buffer at pH 7.2, 2 mM EDTA, and 0.5% (w/v) of $NaDodSO_4$. This linkage allows for the use of probes homologous to the SLG genes to isolate and clone SRK genes.

RNA isolation and RNA blot analysis studies were also performed and the chromatographic data from these studies appears in FIG. 5. In these studies, poly A+ RNA was isolated from pistils, stigmas, anther, pollen, leaf, seedling roots and cotyledons using the FastTrack™ RNA purification protocols (Invitrogen) according to the manufacturer's instructions. Seedling roots and cotyledons were derived from seeds germinated in the dark for several days on vermiculite. Floral tissue (corresponding to approximately 30 flowers) and leaf tissues (0.25 g) were harvested from green-house grown plants. Samples containing approximately 2–5 µg Of pOly A+ RNA was subjected to electrophoresis on 1% (w/v) agarose gels in the presence of formaldehyde as described by Maniatis. An RNA ladder (Bethesda Research Laboratories) was used to estimate the molecular weight of mRNA transcripts. The RNA was transferred to GeneScreen™ membranes as described in Example IV, and prehybridization and hybridization conditions were as for DNA blots. Post-hybridization washes were performed at 65° C. in 0.5% SDS, 2 X SSPE, and then 0.5% SDS, 0.2 X SSPE. The following $^{32}P$-labelled probes were used: a DNA fragment containing the S domain of the $SRK_6$ gene, a DNA fragment containing the kinase-homologous domain, and a DNA fragment containing the $SRK_6$-specific intron probe. In addition, a $^{32}P$-labelled actin probe was used to verify that equal quantities of poly A+ RNA were loaded in-each lane of the gel.

Prior to the transformation of Brasslea described in the following example, pCIB 542, an agropine VIR helper plasmid bearing a spectinomycin drug resistance gene in the place of the T-DNA was constructed. The Ti plasmid, pTi Bo 542 is of interest for use in transformation because Agrobacteria bearing this Ti plasmid are able to infect the agronomically important legumes alfalfa and soybean [see Bio/Technology 2:702 (1984)]. The construction of a pTi Bo 542 derivative deleted of the T-DNA has been described [see J. Bacteriology 168:1291 (1986)]. In this construction, named EHA 101, the T-DNA is replaced by the a kanamycin drug resistance gene. A derivative of EHA 101 having the kanamycin drug resistance gene replaced by a spectinomycin drug resistance gene may be constructed as follows: The plasmid p pi delta 307 [see J. Bacteriology 168:1291 (1986)] has a 1.7 kb region of homology to the left side of Bam 5 of pTi Bo 542 and an 8 kb region of homology to the right side of Bam2a of pTi Bo 542, separated by a unique EcoR1 site. The plasmid pMON30/SR20, which has been deposited under the Budapest Treaty with the American Type Culture Collection and designated as accession number 67113, bears the spectinomycin/streptomycin [spc/str] drug resistance gene from Tn7; pMon 30 is digested with EcoR1; the 5.5 kb fragment containing the spc/str gene isolated from an agarose gel; and ligated into EcoR1-restricted p pi delta 307. The desired recombinant is selected as a spectinomycin resistant (50 µg/ml) tetracycline resistant (10 µg/ml) transformant of *E. coil* HB101.

Plasmid DNA can be introduced into Agrobacteria A136/ EHA101 by transformation. The desired transformant is selected by its streptomycin-resistant tetracycline-resistant kanamycin-resistant phenotype. Homogenates [see J. Mol. Appl. Genet. 1:39 (1981)] of EHA101 and the spectinomycin plasmid are selected after conjugal introduction of the eviction plasmid R751-pMG2 [see J. Bacteriol. 127:1278 (1976)] and selection on gentamycin (50 µlg/ml) and spectinomycin. The desired homogenate has a gentamycin-resistant, spectinomycin-resistant, tetracycline-sensitive, and kanamycin-sensitive phenotype. The structure of the resulting plasmid is confirmed by Southern analysis. A derivative cured of the eviction plasmid is then selected by its drug resistance phenotype of gentamycin sensitivity. This selection is confirmed by Southern analysis.

The construction of transformation vectors, according to one embodiment useful in the present invention and using the Brassica gene is designated SLG-13. This encodes the S-locus specific glycoprotein (SLSG) and is isolated from Brassica oleracea S13 homozygote[see PNAS USA 85:5551 (1988)]. SLG-13 is contained on an 11 kilobase (kb) EcoR1 restriction fragment which contains the SLSG-coding region and approximately 4.2 kb of 5' and 5.0 kb of 3' flanking sequence. This EcoR1 fragment is inserted into the multiple cloning site of the binary vector pC1B10 [see Gene 53:153 (1987)] carrying a chimeric kanamycin-resistance gene for selection of transformed plants. The recombinant vector pill [see The Plant Cell 2, 29 (1990)] or SLG-13/pCIB10 carrying the S13 gene is mobilized into Agrobacterium tumefaciens strain pC1B542/A136 [a derivative of strain EHA101] by triparental mating according to standard published procedures.

Transformation vectors carrying SLG genes are also constructed in the Ti plasmids pBI 121 (Clonetech Laboratories) and pBIN 19 [see EMBO J. 6:3901 (1987)]. Plant transformation utilizing these vectors has also been successful.

Transformation of Brassica is performed according to a method as used in the related crucifer Arabidopsis which uses a mixture of *A. tumefaciens* cells harboring the SLG13/ pCIB10 construct and of root-inducing plasmid from the wild type A. rhizogenes strain A4. In this general protocol, using an SLG gene, tissue explants of B.napus var. "Westar" are obtained and treated essentially as described by Fry et al [see Plant Cell Rep 6:321 (1987)]. Following selection on kanamycin, a kanamycin-resistant primary transformant plant is selected and analyzed for the integration and expression of the appropriate gene, such as the desired SLG or SRK transgene.

Using this general protocol, the transformation of Brassica with an SRK gene according to the present invention was conducted as in the following example.

EXAMPLE V

Transformation of Brassica With The SRK Gene

The 5.8 kb EcoRI fragment that contained the $SRK_6$ coding region with 0.45 kb of upstream and 1.42 kb of downstream flanking sequence, and a chimeric hygromycin phosphotransferase gene for selection of transformed plants were inserted into the multiple cloning site of the binary vector pBIN19. The resulting vector, pJN280-1, was introduced into cells of *Agrobacterium tumefaciens* strain pCIB542/A136 that harbored the resulting plasmid were used to transform flowering stem disks of *B. oleracea* as follows:

Two *B. oleracea* commercial $F_1$ hybrids were used as gene recipient plants: "Kairan" (Chinese Kale, *B. oleracea* L. var alboglabra) and broccoli (*B. oleracea* L. var botrytis). Flower stem disks were transformed [see Plant Cell Rep 6:321 (1987)] with the following modifications. Hygromycin (20 mg/l) was used for selecting transformants instead of kanamycin. Hygromycin was added to the medium for 3 weeks starting from a week after co-culture. Hygromycin resistance was confirmed by placing leaf segments of regenerated shoots on an expression assay medium containing 50 mg/l hygromycin. Untransformed leaf segments were bleached in a week, while transformed leaves remained green and produced callus. The transgenic plants thus identified were grown in a greenhouse with supplemental illumination.

The presence of the $SRK_6$ transgene was confirmed in hygromycin-resistant plants by DNA blot analysis of Eco RI digested DNA using the "intron" probe.

EXAMPLE VI

Evaluation of Self-Incompatibility

The procedure developed by Ko and Baer [see Euphytica 17:298 (1968)] is routinely used to evaluate pollen-stigma interactions for compatibility and incompatibility. In this protocol, excised pistils were collected at least 24 to 48 hours after pollination and macerated in 1 N NaOH for 1 to 2 hours at 22° C. to 24° C. The pistils were then washed 3 times in distilled water, 15 minutes per wash, placed in a drop of aniline blue solution [0.1% (w/v) aniline blue dissolved in 0.1 N K3PO4 and left overnight at 37° C. in a light-proof bottle] on a glass microscope slide, covered with a #2 cover slip, and gently squashed under the cover slip to spread the stylar stigmatic tissues into a monolayer. The stigmas and pollen were then viewed with a fluorescence microscope, under short wave illumination (350 to 400 nm). In addition to the test material, compatible and incompatible pollenstigma controls were run with each test.

Callose deposits in the stigmatic papillae exhibited bright yellow green fluorescence as did callose in the pollen tubes. Incompatible Brassica pollen frequently either failed to germinate or produced short curled and often thickened tubes which may or may not penetrate the stigmatic papillae. Papillar cells in incompatible reactions may produce large amounts of callose. Compatible pollen germinates to produce long lightly fluorescing tubes which grow through the style toward the ovules.

In conclusion, we have described the isolation and analysis of unreported genomic and cDNA clones. The isolation of SLG-related genomic clones from libraries of *B. oleracea* homogenous for both $S_6$ and $S_2$ DNA was previously described in this application. Two $SRK_6$ cDNA clones, were isolated from an $S_6S_6$ stigma cDNA library by screening with the kinase-domain probe of the $SRK_6$. A third cDNA clone, pJS30, was isolated following amplification by the polymerase chain reaction (PCR) of $S_6S_6$ stigma cDNA using the mRNA GeneAmp™ kit (Perkin-Elmer/Cetus). The amplification was primed with an upstream oligonucleotide primer (Seq. No. 7) (5'ACTTGTGGCAAAGCTTCGATT3') and a downstream primer (SEQ. NO 8) (5'CCATC-CCGAATTCCGAGATCT3') complementary sequences within the "S" and kinase domains of $SRK_6$ respectively. The resulting fragment was cloned in the vector pCR1000 using the TA cloning kit (Invitrogen). Dideoxy sequencing was performed with double stranded plasmid templated prepared by cloning restriction fragments into appropriate Bluescript™ vectors (Stratagene) and by generating nested deletions with the Erase-a-base kit (Promega). In addition, oligonucleotides complementary to regularly spaced sites along the $SRK_6$ gene were used as sequencing primers. Sequence analysis was performed with the IBI Pustell and GCG version 6.0 (Univ. of Wisconsin Biotechnology Center) software packages, and the GenBank and SWISSPROT data bases were searched for protein similarity using FASTA.

In further studying and characterizing the present invention, DNA probes were labeled with $^{32}P$ using the random primer kit of Boehringer Mannheim. Three $SRK_6$-derived probes were used (see FIG. 2A): the "S-domain" probe was a 1186 bp Hind II fragment that spanned the majority of $SRK_6$ exon 1; the "intron" probe was a 747 bp Pst I/Hind II fragment derived from intron 1; the 2135 bp "kinasedomain" probe spanned exons 2 through 7. The "actin" probe was a 1.6 Kb cDNA derived from a *B. oleracea* actin gene. For DNA blot analysis, we used an SLG-specific probe derived from the 3'-untranslated region of SLG6-cDNA, and the $SRK_6$-specific "intron" probe described above.

A pair of S locus-linked genes were previously isolated from the $S_2$ homozygote genotype and designated SLG-2A and SLG-2B in our earlier publication entitled: "A new class of S sequences defined by a pollen recessive selfincompatibility allele of Brasslea oleracea" which appeared in Mol. Gen Genet 222:241 (1990), the disclosure of which is incorporated in toto herein.

More specifically, as set forth in this publication, the DNA sequence of both of these genomic EcoRI fragments are described in the following sequence alignment map in which identical nucleotides are indicated by "."; two gaps "--" were introduced to optimize alignment between the two sequences:

```
SLG-2A  ATGAAAGGGGTACAGAACATTTACCACCATTCTTACACCTTCTCGTTCTGTTCTTCCTTGTCTTGATTCTTATTCA    80
SLG-2B  ................................................................................

TCCTGCCCTTTCGATCTATGTCAACACTTTATCGTCTTCAGAGTCTCTCACAATCTCGAGCAATAGAACACTTGTATCTC   160
................................................................................

CCGGTGGAGTCTTTCGAGCTTGGTTTCTTCAAACCCTTGGGACGCTCGCAATGTATCTCGGAATATGGTATAAGAAAGTC   240
............................................................G..............A...C

TCCCAGAAAACCTACGACATGGGTCGCAAACAGAGACAACCCTCTACTAATTCCACTTGAACTCTCAAAATCTCTGGCAA   320
C..TG...........................................C.............T.C.G..T........C

CAATCTGTCCCTGCTAGGTCAGTCTAATAACACTGTTTGGTCGACAAATCTTACTAGAGAAAATGTGAGATCACCAGTGA   400
.....A........................................................G..C....T..G....

TAGCAGAGCTTCTTCCCAACGTAATTTTGTAATGAGATACTCCAGCAACAAAGACTCAAGTGGATTCTTGTGGCAGAGT    480
.........................A......C......A.......................................

TTCGATTTTCCGACAGATACTTTACTTCCGGATATGAAACTAGGTTACGATCTCAAAACAGGGCGTACCAGAATTCTTAC   560
.........................G......................................GT.C..........

ATCATGGAAGTTCAGATGATCCGTCAAGCGGGAATACCAGTACAAAATCGACACTCAAAGGGGATTGCCAGAGTTTAGTTA   640
..G......A.G.........................TT..GT.......C........T..G........T.......

TTCTTA---ATCAAG-----GACGTTATGAAATGCAAAGGAGCGGTCCGTGGAATGGAGTTAGTGGCATA              720
.....TAA....TTTTTGAATCA...GT......C.................T..........................

CCGAGGTGCAAGGATTAAATTACATGGTTTACAATTATACGGAGAACAGTGAGAACAGTGAGAGATCTCTTACACGTTCCATATGAC   800
..............G.........................................................G..T...

CAACCAAAGCATCTACTCCAGATTGACAGTCAGTGACTATACACTTAATGACGTGGATCCCGCCATCACGGGCAT         880
..........................................G.TG...CG..........................AT.

GGAGCATGTTCTGGACTTTACCGACGACGTGTGCGATCCACTTTACTTATGTGATCTTATTCTTACTGTGACCTAATT     960
........C.C...........................................G........................

ACGTCACCTAACTGAACTGTATTAGAGGTTGCGTTCCCAAGAACCCGCAGCAGTGGGACTGAGAGACGGAACACAGGG    1040
................................................................G..............

GTGTGTGAGGACGACGCAGATGAGCTGTAGTGGAGATGGCTTTTTGCGGCTAAACAATATGAATTTGCCGGATACTAAGA  1120
................................G................................................

CGGGCACTGTGGATCGGATAATTGATGTGAAAAAATGCGAAGAGAGGTGTCTAAGTGATTGTAACTGTACGTCGTTTGCT  1200
...A....................C..G................................T.C................

AATTGCCGGATGTTCGAAACGGCGAATTGGGGTTGTGTGTTTTGGACCGGAGAGCTCGTTGAGATCAGGAAATTTGCCGTCGG  1280
..............G..T..A..G.............................................C............

TGGTCAAGATCTTTACGTCAGGTTGAATGCTCGCTGATCTAGGTTAG   1326
................A..............................
```

The predicted amino acid sequences of SLG-2A, SLG-2B, and SLG-13 are shown in the following allignment map in which amino acid residues (single letter codes) that are identical between SLG-13 and SLG-2A are boxed, "=" indicates residues conserved between SLG-2A and SLG-2B; "*" represent spaces introduced for optimal alignment; potential glycosylation sites found in SLG-2A, SLG-13 and SLG-2B are indicated by open circles; and arrowheads delineate the interspersed A, B, C, D conserved and variable domains.

Of the 7 $SRK_2$ exons, only the first was reported in the prior publication. The location of the remaining 6 exons begins ≈2.2 kb downstream of the first. Strikingly, both the $SRK_6$ and $SRK_2$ genomic sequences have an in-frame stop codon (TAG) within intron 1, position 2 nucleotides downstream of the 5' splice site. The placement of this stop codon relative to the "S" domain of SRK exactly matches the position of the stop codon used by SLG (FIG. 4A), suggesting that it has functional relevance. For example, the stop codon could be retained in alternative transcripts of SRK, causing the production of a truncated SLG-like protein consisting of only the "S" domain.

```
SLG-13   N E [G V] K K T [S Y T] L [S F L L V F] F [V L I L F] R [P A] F [S I] N * * [T L S S] T  9
SLG-2A   M K [G V] Q N I [S Y T] F [S F L L V F] L [V L I L F] H [P A] L [S I] Y V N [T L S S] S
SLG-2B   = = = = = = = = = = = = = = = = = = = = = = = = = = = = = = = = = = = = =

SLG-13   [E S L T I S S N R T L V S P G] N [V F E L G F F K] T T S S [S] R [W Y L G I W Y K K] F  49
SLG-2A   [E S L T I S S N R T L V S P G] G [V F E L G F F K] P L G R [S] Q [W Y L G I W Y K K] V
SLG-2B   = = = = = = = = = = = = = = = = = = = = = = = = = = = = R = = = = = = = = = A
                                       o

SLG-13   P Y R [T Y] V [W V A N R D N P L] S [N] D [I G T L K I S G N N L V L L] D H [S N] K S [V W]  89
SLG-2A   S Q K [T Y] A [W V A N R D N P L] T [N] S [I G T L K I S G N N L V L L] G Q [S N] N T [V W]
SLG-2B   P W = = = = = = = = = = = = = S S = = = = = = = = = = = = = = S = = T = = = =

SLG-13   [S T N] V [T R G] [N E] [R S P V] V [A E L L] D [N G N F V M R] D [S] N S N N A [S] Q [F L W Q S]  129
SLG-2A   [S T N] L [T R E] [N V] [R S P V] I [A E L L] P [N G N F V M R] Y [S] S N K D I [S] G [F L W Q S]
SLG-2B   = = = = = = G = A = = = = = = = = = = = = = = = = = I = H = N = = = S = = = = = =
                     o

SLG-13   [F D] Y [P T D T L L P] E [M K L G Y D L K T G] L [N R] F [L T S W R S S D D P S S G] D Y  169
SLG-2A   [F D] F [P T D T L L P] D [M K L G Y D L K T G] R [N R] I [L T S W R S S D D P S S G] N T
SLG-2B   = = = = = = = = = = = E = = = = = = = = = = = = = = = F = = = = K G = = = = = = = = = F
                                                                                        o

SLG-13   S [Y K] L E L R [R] * [L P E F] Y L * S S [G] S F * * * R L H [R S G P W N G] F R I [S G I]  209
SLG-2A   T [Y K] I D T Q [R G] [L P E F] I L * N Q [G] R Y * * * E M Q [R S G P W N G] M E F [S G I]
SLG-2B   V = = L = I R = = = = = = = I = = F L N Q R V = T = = = = = = = = = = = = = =

SLG-13   [P E] [D] [Q] K [L] S [Y M V Y N] F [T E N S E E] A A [Y T F] L [M T N] N [S] E [Y S R L T] I [S] S T  249
SLG-2A   [P E] V [Q] G [L] N [Y M V Y N] Y [T E N S E E] I S [Y T F] H [M T N] Q [S] I [Y S R L T] V [S] D Y
SLG-2B   = = = = = = = = = = = = = = = = = = = A = S = = = = = = = = = = = = = = = E L
                                   o                                             o

SLG-13   G Y F E [R L T W] [A] P [S] [S] V V [W] N V [F W] S S [P] N H Q [C D] M Y R M [C G] P [Y S Y C D] V  289
SLG-2A   T L N * [R L T W] I [P] P [S] R A [W] S M [F W] T L [P] T D V [C D] P L Y L [C G] S [Y S Y C D] L
SLG-2B   = = D * = = = = = = = = = = D = = L = = = = = = = = = = = = = = = = = = = = =

SLG-13   N [T S P] V [C N C I] Q [G F R] [P K N] R [Q Q W D L R] I P [T] S [G C] I [R] [R] T R L [S C S G D]  329
SLG-2A   I [T S P] N [C N C I] R [G F V] [P K N] P [Q Q W D L R] D G [T] Q [G C] V [R] T [T] Q M [S C S G D]
SLG-2B   = = = = = = = = = = = = = = = = = = = = = = = = = = = = = = R = = = = = = = = = =

SLG-13   [G F] T [R] M K [N M] K [L P] E [T] T M [A] I [V] H [R] S [I] G L [K] E [C E] K [R C L S D C C N C T] A [F]  369
SLG-2A   [G F] L [R] L N N M N [L P] D [T] K T [A] T [V] D [R] I [I] D V [K] K [C E] E [R C L S D C C N C T] S [F]
SLG-2B   = = = = = = = = = = = = = = = = = = = = T M = = = = = = = = = = = = = = = = = =
                                                                                           o

SLG-13   [A] N [A D] I [R N] R G T [G C V] I [W T G E L] E D [I R] T Y [F A] * D [G Q D L Y V R L] [A] [A A]  409
SLG-2A   [A] I [A D] V [R N] G E L [G C V] F [W T G E L] V E [I R] * K [F A] V G [G Q D L Y V R L] N [A A]
SLG-2B   = = = = = = = G = = = = = = = = = = = A = = * = = = = = = = = = = = = = =

SLG-13   [D L] V
SLG-2A   [D L] G
SLG-2B   = = =
```

The isolation of cDNA clones corresponding to SLG-2A had identified this gene as the $S_2$ homologue of SLG6, and this gene was therefore referred to as $SLG_2$. In making the present invention, we sequenced 7.2 kb of the genomic clone isolated using the SLG-2B sequence as a probe. We therefore have designated the complete gene of which SLG-2B represents the S-domain, as SRK2, the homologue of $SRK_6$ in plants with the S2 recognition genotype.

The predicted 855 amino acid SRK2 polypeptide sequence (FIG. 3) contains all of the structural features predicted for SRK6, however $SRK_2$ and $SRK_6$ are only 68 conserved. The most highly conserved comains are the "S" (67%) and kinase (71%) domains (FIG. 4B). This level of diverlence is surprisingly high for allelic variants, yet it parallels the polymorphism observed between alleles of SLG, since the SLG6 and SLG2 protein sequences are 68% identical. In contrast, each SRK "S" domain was more similar to its corresponding SLG allele (≈90% amino acid identity; FIG. 4B). thus, SRK and SLG are structurally related genes pairs. As a unit, they have apparently evolved in concert within each S genotype, while diverging extensively between genotypes.

As described in the preceding examples, to study the expression of the $SRK_6$ gene, we subjected poly(A) RNA from pistils, anthers, leaves, cotyledons and roots to gel blot analysis using separate probes derived from the kinase domain, the "S" domain, and the first intron of $SRK_6$ (see FIG. 2A). The most intense hybridization signals were obtained in mature pistils where transcripts ranged in size from 1.6 kb to 5.9 kb (FIG. 5A). Some of these transcript species were assigned to genes other than SRK6. In particular, the highly abundant "S"-homologous 1.6 kb transcript was previously shown to be derived from the SLG gene in experiments with transgenic tobacco. Only the transcript species of 3.0 kb (arrowhead), 4.1 kb (asterisk) and 2.3 kb (circle) were unambiguously assigned to the $SRK_6$ gene, and their characterization is described in detail.

The 3.0 kb transcript and a slightly differing transcript in anthers were recognized by both the kinase- and "S"-domain probes, but not the intron probe. These transcript sizes were consistent with the predicted size (2832 bp) of a fully spliced $SRK_6$ transcript. A 3.0 kb transcript was also detected by the kinase-domain probe in leaves, and in cotyledons after very long (>1 week) film exposures, however, not in seedling roots; this leaf transcript did not hybridize to the "S"-domain probe except under low-stringency wash conditions, and thus derived, not from the $SRK_6$ gene, but from any of several SRK-related genes detected in the Brassica genome. The 4.1 kb transcript hybridized to the "intron" probe as well as the kinase- and "S"-domain probes, and was of a size consistent with that predicted for an unspliced $SRK_6$ transcript (4180 bp). The 2.3 kb transcript hybridized to the kinase-domain and "intron" probes but not the "S"-domain probe, and was possibly the result of alternative splicing or the action of an alternative promoter.

The levels of fully spliced and unspliced $SRK_6$ transcripts were regulated in anthers during the rapid succession of pollen development stages (FIG. 5B). Maximal expression of $SRK_6$ was observed in anthers at the binucleate microspore stage. At the uninucleate stage there were low levels of transcript, and by the trinucleate stage no expression was detected. This regulation of message quantity cannot be attributed to general variation of RNA levels since RNA from all stages contained equal amount of actin transcript (FIG. 5B). In order to verify the origin of these transcripts, we introduced the $SRK_6$ gene into a recipient B. oleracea strain that carried the $S_2$ allele. Because the SRK genes derived from the $S_2$ and $S_6$ alleles are highly diverged, the SRK transcripts endogenous to this strain were not recognized by the $SRK_6$-derived probes at the stringency used. In 10 transgenic plants analyzed, several showed detectable levels of the splices and unspliced transcripts (FIG. 5C). These transcripts were observed exclusively in pistil and anther tissue and were not detected in untransformed controls. Transcripts of 1.6 kb were detected in both transformed and untransformed plants, and therefore represented endogenous messages not encoded by the $SRK_6$ transgene.

Thus, like SLG, the SRK gene is specifically transcribed in pistils and anthers. However, SRK transcripts are substantially less abundant in mature pistils than SLG transcripts, since they produced a 140–180 fold weaker hybridization signal with the "S"-domain probe. In addition, SRK directs the synthesis of several mRNA species that potentially encode different protein products. For example, the unspliced 4.1 kb transcript would retain the in-frame stop codon in intron 1 (see above), and would thus encode a secreted C-terminally truncated protein encompassing only "S" domain. In contrast, the 2.3 kb transcript, which lacks most or all of exon 1, possibly encodes an N-terminally truncated protein. Instances in which receptor tyrosine kinase genes encode N-terminally truncated as well as C-terminally truncated forms have been identified.

Several lines of evidence imply that SRK functions in the mechanism of SI. First, SRK is located at the S locus, as was independently demonstrated for two different SRK alleles. Second, the predicted products of these SRK alleles show the high degree of polymorphism expected for proteins responsible for cellular recognition specificity. Finally, SRK transcription is active in the male and female reproductive organs, from which are derived the two interacting cell types that mediate recognition. A possible model for this recognition might involve the allelespecific binding of a putative ligand which might also be encoded at the S locus. Alternatively, SRK and SLG might display allele specific homophilic binding. The concerted evolution of the SLG/SRK gene pair suggests that their products interact functionally, perhaps as components of a ligand binding complex or as unassociated competitors for this binding. Moreover, by phosphorylating intracellular substrates, SRK might couple these initial molecular recognition events to the signal transduction chain that lead to pollen acceptance or rejection. Preliminary evidence for the existence of multiple SRK-like genes, some of which may be transcribed in leaves of Brassica, and the finding that ZmPK1 is transcribed in vegetative tissues of maize, suggests that SRK is a specialized member of a universal class of cell-cell communication receptors that function in higher plants.

Based upon the data provided in this description, it is clear that SLG and SRK are tightly linked genetically and that they reside at the S locus. This conclusion is clear because it was possible to isolate $SRK_6$, the SRK gene derived from a B. oleracea $S_6$ homozygote, from a collection of SLG-homologous genomic clones. Subsequent attempts to characterize clones derived from the S locus identified a genomic region defined by 9 independent overlapping clones. Partial sequence analysis of DNA flanking the region of SLG homology in these clones revealed sequence similarity to known protein kinases and to ZmPK1. $SRK_6$ was next shown to be genetically linked to the S locus by restriction fragment length polymorphism (RFLP) analysis of a population of $F_2$ plants segregating for the $S_6$ and $S_{14}S1$ phenotypes (FIG. 1). As previously reported [see Genetics 127:221 (1991)], an SLG-specific probe identified an EcoRI RFLP between the two parental strains that indicated which SLG allele(s) was present in each of the plants examined (FIG. 1A). When a DNA fragment immediately downstream of the SLG-homologous region of the $SRK_6$ gene (derived from intron 1 of $SRK_6$; see FIG. 2B) was used as a probe, a single EcoRI restriction fragment was identified in the $S_6$ parent but not in the S14 parent (FIG. 1B). A perfect correlation was observed between the presence of the SLG6 allele, the presence of the $SRK_6$ allele, and the $S_6$ incompatibility specificity as determined by pollination assays in a total of 78 $F_2$ plants in this population (16 $S_6$:38 $S_6S_{14}$:24 $S_{14}S_{14}$), of which 9 are shown in FIG. 1.

The SRK genes may be transformed into appropriate plants either alone or together with SLG genes. This may be done by placing the SRK gene on a single vector, or when transformation together with an SLG gene is desired, by placing the SRK and SLG genes on separate vectors or physically linking the genes on a single vector. In addition, separate plants may be transformed with either a single SLG or SRK gene, and these plants may then be crossed with conventional techniques to produce an $F_1$ generation plant containing both sequences within its genome.

The plants which are the product of transformation with the SRK and/or SRK-SLG gene according to the present invention may be incompatible with either pollen of the same genotype as that of the isolated SRK gene or the pollen of the transformed plant may then be rendered incompatible with plants of the same genotype as that of the SRK gene.

In addition to the methods for identifying additional SRK genes using SLG clones to identify and isolate SRK genes described herein, the known homology among SLG genes may also provide other SLG probes for isolating the SRK gene, and these methods using modified but closely related probes are deemed to be within the scope of the present invention. Furthermore, additional techniques may be used for obtaining SRK genes. One such technique described in U.S. patent application Ser. No. 07/568,657 (the disclosure of which has been incorporated herein) describes the cloning of a cDNA encoding a SLG protein from stigmas of selfin-compatible plants.

The following listing contains the nucleotide and amino acid sequences of the compounds described herein:

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
( A ) LENGTH: 2833 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

| | | | | | | | | | | | | | |
|---|---|---|---|---|---|---|---|---|---|---|---|---|---|
| ATG | AAA | GGT | GCA | CGA | AAC | ATC | TAT | CAC | CAT | TCT | TAC | ATG | 3 9 |
| TCC | TTT | TTG | CTC | GTC | TTC | GTT | GTC | ATG | ATT | CTA | ATT | CAT | 7 8 |
| CCT | GCC | CTT | TCG | ATC | TAT | ATC | AAC | ACT | TTG | TCG | TCT | ACA | 1 1 7 |
| GAA | TCT | CTT | ACA | ATC | TCA | AGC | AAC | AAA | ACA | CTT | GTA | TCT | 1 5 6 |
| CCC | GGT | AGT | ATC | TTC | GAG | GTC | GGC | TTC | TTC | AGA | ACC | AAT | 1 9 5 |
| TCT | CGT | TGG | TAT | CTC | GGG | ATG | TGG | TAC | AAG | AAA | GTG | TCC | 2 3 4 |
| GAC | AGA | ACC | TAT | GTA | TGG | GTT | GCC | AAC | AGA | GAT | AAC | CCA | 2 7 3 |
| CTC | TCC | AAT | GCC | ATT | GGA | ACC | CTC | AAA | ATC | TCA | GGC | AAT | 3 1 2 |
| AAT | CTT | GTC | CTC | CTT | GAT | CAC | TCC | AAT | AAA | CCT | GTT | TGG | 3 5 1 |
| TGG | ACG | AAT | CTT | ACT | AGA | GGA | AAT | GAG | AGA | TCT | CCG | GTG | 3 9 0 |
| GTG | GCT | GAG | CTT | CTC | GCT | AAC | GGA | AAC | TTC | GTG | ATG | CGA | 4 2 9 |
| GAC | TCC | AGT | AAC | AAC | GAC | GCA | AGT | GAA | TAC | TTG | TGG | CAA | 4 6 8 |
| AGT | TTC | GAT | TAC | CCT | ACG | GAT | ACT | TTG | CTT | CCA | GAG | ATG | 5 0 7 |
| AAA | CTG | GGT | TAC | AAC | CTC | AAA | ACA | GGG | TTG | AAC | AGG | TTC | 5 4 6 |
| CTT | ACA | TCA | TGG | AGA | AGT | TCA | GAT | GAT | CCA | TCA | AGC | GGG | 5 8 5 |
| AAT | TTC | TCG | TAC | AAG | CTC | GAA | ACC | CAA | AGT | CTT | CCT | GAG | 6 2 4 |
| TTT | TAT | CTA | TCG | CGG | GAG | AAC | TTT | CCA | ATG | CAT | CGG | AGT | 6 6 3 |
| GGT | CCA | TGG | AAT | GGA | ATC | CGA | TTT | AGT | GGC | ATA | CCA | GAG | 7 0 2 |
| GAC | CAA | AAG | CTG | AGT | TAC | ATG | GTG | TAC | AAT | TTC | ATA | GAG | 7 4 1 |
| AAT | AAT | GAA | GAG | GTC | GCT | TAT | ACA | TTC | CGA | ATG | ACC | AAC | 7 8 0 |
| AAC | AGC | TTC | TAC | TCG | AGA | TTG | ACA | CTA | ATT | TCC | GAA | GGG | 8 1 9 |

| | | | | | | | | | | | | |
|---|---|---|---|---|---|---|---|---|---|---|---|---|
| TAT | TTT | CAG | CGA | CTG | ACG | TGG | TAT | CCG | TCA | ATA | AGG | ATA | 858 |
| TGG | AAC | AGG | TTC | TGG | TCT | TCT | CCA | GTG | GAC | CCC | CAG | TGT | 897 |
| GAT | ACT | TAC | ATA | ATG | TGT | GGA | CCT | TAC | GCT | TAC | TGT | GAC | 936 |
| GTG | AAC | ACA | TCA | CCG | GTT | TGT | AAC | TGT | ATC | CAA | GGG | TTC | 975 |
| AAT | CCC | CGG | AAT | ATA | CAG | CAG | TGG | GAT | CAG | AGA | GTC | TGG | 1014 |
| GCA | GGT | GGG | TGT | ATA | AGG | AGG | ACG | CAG | CTT | AGC | TGC | AGT | 1053 |
| GGA | GAT | GGT | TTT | ACC | AGG | ATG | AAG | AAG | ATG | AAG | TTG | CCA | 1092 |
| GAA | ACT | ACG | ATG | GCG | ACT | GTC | GAC | CGT | AGT | ATT | GGT | GTG | 1131 |
| AAA | GAA | TGT | AAG | AAG | AGG | TGC | ATT | AGC | GAT | TGT | AAT | TGT | 1170 |
| ACC | GCT | TTT | GCA | AAT | GCA | GAT | ATC | CGG | AAT | GGT | GGG | TCG | 1209 |
| GGT | TGT | GTG | ATT | TGG | ACC | GAA | CGC | CTT | GAG | GAT | ATC | CGG | 1248 |
| AAT | TAC | GCT | ACT | GAC | GCT | ATT | GAC | GGT | CAA | GAT | CTT | TAT | 1287 |
| GTC | AGA | TTG | GCT | GCA | GCT | GAT | ATC | GCT | AAG | AAG | AGA | AAC | 1326 |
| GCG | AGT | GGG | AAA | ATT | ATA | AGT | TTG | ACT | GTT | GGT | GTT | AGT | 1365 |
| GTT | CTG | CTT | CTG | CTG | ATC | ATG | TTC | TGC | CTC | TGG | AAA | AGA | 1404 |
| AAA | CAA | AAG | CGA | GCA | AAA | GCA | AGT | GCA | ATA | TCC | ATT | GCA | 1443 |
| AAT | ACA | CAG | AGA | AAC | CAA | AAC | TTG | CCT | ATG | AAC | GAG | ATG | 1482 |
| GTA | CTA | TCA | AGC | AAG | AGA | GAG | TTT | TCT | GGA | GAG | TAC | AAA | 1521 |
| TTT | GAG | GAA | CTG | GAA | CTT | CCA | TTG | ATA | GAG | ATG | GAA | ACT | 1560 |
| GTT | GTC | AAA | GCC | ACC | GAA | AAT | TTC | TCC | AGC | TGT | AAC | AAA | 1599 |
| CTC | GGA | CAA | GGT | GGT | TTT | GGT | ATT | GTT | TAC | AAG | GGA | AGA | 1638 |
| TTA | CTT | GAC | GGG | AAA | GAA | ATT | GCA | GTA | AAA | AGG | CTA | TCA | 1677 |
| AAG | ACG | TCA | GTT | CAA | GGG | ACT | GAT | GAG | TTT | ATG | AAT | GAG | 1716 |
| GTG | ACA | CTA | ATT | GCG | AGG | CTT | CAG | CAT | ATA | AAC | CTT | GTT | 1755 |
| CAA | GTT | CTT | GGC | TGT | TGC | ATT | GAA | GGA | GAT | GAG | AAG | ATG | 1794 |
| TTG | ATA | TAT | GAG | TAT | TTG | GAA | AAT | TTA | AGC | CTT | GAT | TCT | 1833 |
| TAT | CTC | TTT | GGT | AAA | ACC | CGA | AGG | TCT | AAG | CTA | AAT | TGG | 1872 |
| AAT | GAG | AGA | TTC | GAC | ATT | ACC | AAT | GGT | GTT | GCT | CGA | GGG | 1911 |
| CTT | TTA | TAT | CTT | CAT | CAA | GAC | TCA | CGG | TTT | AGG | ATA | ATC | 1950 |
| CAC | AGA | GAT | TTG | AAA | GTA | AGT | AAC | ATT | TTG | CTT | GAC | AAA | 1989 |
| AAT | ATG | ATC | CCA | AAG | ATC | TCG | GAT | TTT | GGG | ATG | GCC | AGG | 2028 |
| ATA | TTT | GAA | AGG | GAC | GAA | ACG | GAA | GCT | AAC | ACA | ATG | AAG | 2067 |
| GTG | GTC | GGA | ACA | TAC | GGC | TAC | ATG | TCC | CCG | GAA | TAC | GCA | 2106 |
| ATG | TAT | GGG | ATA | TTC | TCG | GAA | AAA | TCA | GAT | GTT | TTC | AGT | 2145 |
| TTT | GGA | GTC | ATA | GTT | CTT | GAA | ATT | GTT | AGT | GGA | AAG | AAG | 2184 |
| AAC | AGA | GGA | TTC | TAC | AAC | TTG | GAC | TAC | GAA | AAC | GAT | CTC | 2223 |
| CTA | AGC | TAT | GTA | TGG | AGT | CGT | TGG | AAG | GAA | GGA | AGA | GCG | 2262 |
| CTA | GAA | ATC | GTA | GAT | CCC | GTC | ATC | GTA | GAT | TCA | CTG | TCA | 2301 |
| TCA | CAG | CCA | TCA | ATA | TTT | CAA | CCA | CAA | GAA | GTC | CTA | AAA | 2340 |
| TGT | ATT | CAA | ATT | GGT | CTC | TTG | TGT | GTT | CAA | GAA | CTT | GCA | 2379 |

| | | | | | | | | | | | | |
|---|---|---|---|---|---|---|---|---|---|---|---|---|
| GAG | CAC | AGA | CCA | GCG | ATG | TCG | TCT | GTG | GTT | TGG | ATG | TTT | 2418 |
| GGA | AGT | GAA | GCA | ACA | GAG | ATT | CCT | CAG | CCT | AAA | CCG | CCA | 2457 |
| GGT | TAT | TGC | GTC | AGA | AGA | AGT | CCT | TAT | GAA | CTT | GAT | CCT | 2496 |
| TCA | TCA | AGT | TGG | CAA | TGT | GAC | GAA | AAT | GAA | TCC | TGG | ACG | 2535 |
| GTG | AAC | CAG | TAC | ACC | TGC | TCA | GTC | ATT | GAT | GCC | CGG | | 2571 |

| | | |
|---|---|---|
| TAATATGATA GCTGAGTGAT TCAATATCAT ATGTGAAAGA GGGAAAATAA | | 2621 |
| AATCTCATTA GATAAGTAGG TTATTTCGAT AACCACTTCT TGTTATTTTC | | 2671 |
| TGGCGGTGTT GTCATTATCC CCTTTATATT AAAAAGAAGC ATTTGTATTA | | 2721 |
| AATCCCCTTG CCTCAAGAGA TATTCACAAG AATACTATTG TGACGTGACA | | 2771 |
| GCCTCACTAT CGTTTAAACA TTACAATGCT GACGTGTGGC TTGTAAATAG | | 2821 |
| CTTCTCAGAC CA | | 2833 |

( 2 ) INFORMATION FOR SEQ ID NO: 2:

( i ) SEQUENCE CHARACTERISTICS:
        ( A ) LENGTH: 857 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Gly | Ala | Arg<br>5 | Asn | Ile | Tyr | His | His<br>10 | Ser | Tyr | Met | Ser | Phe<br>15 |
| Leu | Leu | Val | Phe | Val<br>20 | Val | Met | Ile | Leu | Ile<br>25 | His | Pro | Ala | Leu | Ser<br>30 |
| Ile | Tyr | Ile | Asn | Thr<br>35 | Leu | Ser | Ser | Thr | Glu<br>40 | Ser | Leu | Thr | Ile | Ser<br>45 |
| Ser | Asn | Lys | Thr | Leu<br>50 | Val | Ser | Pro | Gly | Ser<br>55 | Ile | Phe | Glu | Val | Gly<br>60 |
| Phe | Phe | Arg | Thr | Asn<br>65 | Ser | Arg | Trp | Tyr | Leu<br>70 | Gly | Met | Trp | Tyr | Lys<br>75 |
| Lys | Val | Ser | Asp | Arg<br>80 | Thr | Tyr | Val | Trp | Val<br>85 | Ala | Asn | Arg | Asp | Asn<br>90 |
| Pro | Leu | Ser | Asn | Ala<br>95 | Ile | Gly | Thr | Leu | Lys<br>100 | Ile | Ser | Gly | Asn | Asn<br>105 |
| Leu | Val | Leu | Leu | Asp<br>110 | His | Ser | Asn | Lys | Pro<br>115 | Val | Trp | Trp | Thr | Asn<br>120 |
| Leu | Thr | Arg | Gly | Asn<br>125 | Glu | Arg | Ser | Pro | Val<br>130 | Val | Ala | Glu | Leu | Leu<br>135 |
| Ala | Asn | Gly | Asn | Phe<br>140 | Val | Met | Arg | Asp | Ser<br>145 | Ser | Asn | Asn | Asp | Ala<br>150 |
| Ser | Glu | Tyr | Leu | Trp<br>155 | Gln | Ser | Phe | Asp | Tyr<br>160 | Pro | Thr | Asp | Thr | Leu<br>165 |
| Leu | Pro | Glu | Met | Lys<br>170 | Leu | Gly | Tyr | Asn | Leu<br>175 | Lys | Thr | Gly | Leu | Asn<br>180 |
| Arg | Phe | Leu | Thr | Ser<br>185 | Trp | Arg | Ser | Ser | Asp<br>190 | Asp | Pro | Ser | Ser | Gly<br>195 |
| Asn | Phe | Ser | Tyr | Lys<br>200 | Leu | Glu | Thr | Gln | Ser<br>205 | Leu | Pro | Glu | Phe | Tyr<br>210 |
| Leu | Ser | Arg | Glu | Asn<br>215 | Phe | Pro | Met | His | Arg<br>220 | Ser | Gly | Pro | Trp | Asn<br>225 |

```
Gly  Ile  Arg  Phe  Ser       Gly  Ile  Pro  Glu  Asp       Gln  Lys  Leu  Ser  Tyr
               230                           235                           240

Met  Val  Tyr  Asn  Phe       Ile  Glu  Asn  Asn  Glu       Glu  Val  Ala  Tyr  Thr
               245                           250                           255

Phe  Arg  Met  Thr  Asn       Asn  Ser  Phe  Tyr  Ser       Arg  Leu  Thr  Leu  Ile
               260                           265                           270

Ser  Glu  Gly  Tyr  Phe       Gln  Arg  Leu  Thr  Trp       Tyr  Pro  Ser  Ile  Arg
               275                           280                           285

Ile  Trp  Asn  Arg  Phe       Trp  Ser  Ser  Pro  Val       Asp  Arg  Gln  Cys  Asp
               290                           295                           300

Thr  Tyr  Ile  Met  Cys       Gly  Pro  Tyr  Ala  Tyr       Cys  Asp  Val  Asn  Thr
               305                           310                           315

Ser  Pro  Val  Cys  Asn       Cys  Ile  Gln  Gly  Phe       Asn  Pro  Arg  Asn  Ile
               320                           325                           330

Gln  Gln  Trp  Asp  Gln       Arg  Val  Trp  Ala  Gly       Gly  Cys  Ile  Arg  Arg
               335                           340                           345

Thr  Gln  Leu  Ser  Cys       Ser  Gly  Asp  Gly  Phe       Thr  Arg  Met  Lys  Lys
               350                           355                           360

Met  Lys  Leu  Pro  Glu       Thr  Thr  Met  Ala  Thr       Val  Asp  Arg  Ser  Ile
               365                           370                           375

Gly  Val  Lys  Glu  Cys       Lys  Lys  Arg  Cys  Ile       Ser  Asp  Cys  Asn  Cys
               380                           385                           390

Thr  Ala  Phe  Ala  Asn       Ala  Asp  Ile  Arg  Asn       Gly  Gly  Ser  Gly  Cys
               395                           400                           405

Val  Ile  Trp  Thr  Glu       Arg  Leu  Glu  Asp  Ile       Arg  Asn  Tyr  Ala  Thr
               410                           415                           420

Asp  Ala  Ile  Asp  Gly       Gln  Asp  Leu  Tyr  Val       Arg  Leu  Ala  Ala  Ala
               425                           430                           435

Asp  Ile  Ala  Lys  Lys       Arg  Asn  Ala  Ser  Gly       Lys  Ile  Ile  Ser  Leu
               440                           445                           450

Thr  Val  Gly  Val  Ser       Val  Leu  Leu  Leu  Leu       Ile  Met  Phe  Cys  Leu
               455                           460                           465

Trp  Lys  Arg  Lys  Gln       Lys  Arg  Ala  Lys  Ala       Ser  Ala  Ile  Ser  Ile
               470                           475                           480

Ala  Asn  Thr  Gln  Arg       Asn  Gln  Asn  Leu  Pro       Met  Asn  Glu  Met  Val
               485                           490                           495

Leu  Ser  Ser  Lys  Arg       Glu  Phe  Ser  Gly  Glu       Tyr  Lys  Phe  Glu  Glu
               500                           505                           510

Leu  Glu  Leu  Pro  Leu       Ile  Glu  Met  Glu  Thr       Val  Val  Lys  Ala  Thr
               515                           520                           525

Glu  Asn  Phe  Ser  Ser       Cys  Asn  Lys  Leu  Gly       Gln  Gly  Gly  Phe  Gly
               530                           535                           540

Ile  Val  Tyr  Lys  Gly       Arg  Leu  Leu  Asp  Gly       Lys  Glu  Ile  Ala  Val
               545                           550                           555

Lys  Arg  Leu  Ser  Lys       Thr  Ser  Val  Gln  Gly       Thr  Asp  Glu  Phe  Met
               560                           565                           570

Asn  Glu  Val  Thr  Leu       Ile  Ala  Arg  Leu  Gln       His  Ile  Asn  Leu  Val
               575                           580                           585

Gln  Val  Leu  Gly  Cys       Cys  Ile  Glu  Gly  Asp       Glu  Lys  Met  Leu  Ile
               590                           595                           600

Tyr  Glu  Tyr  Leu  Glu       Asn  Leu  Ser  Leu  Asp       Ser  Tyr  Leu  Phe  Gly
               605                           610                           615

Lys  Thr  Arg  Arg  Ser       Lys  Leu  Asn  Trp  Asn       Glu  Arg  Phe  Asp  Ile
               620                           625                           630
```

| Thr | Asn | Gly | Val | Ala | Arg | Gly | Leu | Leu | Tyr | Leu | His | Gln | Asp | Ser |
|---|---|---|---|---|---|---|---|---|---|---|---|---|---|---|
| | | | | 635 | | | | | 640 | | | | | 645 |

| Arg | Phe | Arg | Ile | Ile | His | Arg | Asp | Leu | Lys | Val | Ser | Asn | Ile | Leu |
|---|---|---|---|---|---|---|---|---|---|---|---|---|---|---|
| | | | | 650 | | | | | 655 | | | | | 660 |

| Leu | Asp | Lys | Asn | Met | Ile | Pro | Lys | Ile | Ser | Asp | Phe | Gly | Met | Ala |
|---|---|---|---|---|---|---|---|---|---|---|---|---|---|---|
| | | | | 665 | | | | | 670 | | | | | 675 |

| Arg | Ile | Phe | Glu | Arg | Asp | Glu | Thr | Glu | Ala | Asn | Thr | Met | Lys | Val |
|---|---|---|---|---|---|---|---|---|---|---|---|---|---|---|
| | | | | 680 | | | | | 685 | | | | | 690 |

| Val | Gly | Thr | Tyr | Gly | Tyr | Met | Ser | Pro | Glu | Tyr | Ala | Met | Tyr | Gly |
|---|---|---|---|---|---|---|---|---|---|---|---|---|---|---|
| | | | | 695 | | | | | 700 | | | | | 705 |

| Ile | Phe | Ser | Glu | Lys | Ser | Asp | Val | Phe | Ser | Phe | Gly | Val | Ile | Val |
|---|---|---|---|---|---|---|---|---|---|---|---|---|---|---|
| | | | | 710 | | | | | 715 | | | | | 720 |

| Leu | Glu | Ile | Val | Ser | Gly | Lys | Lys | Asn | Arg | Gly | Phe | Tyr | Asn | Leu |
|---|---|---|---|---|---|---|---|---|---|---|---|---|---|---|
| | | | | 725 | | | | | 730 | | | | | 735 |

| Asp | Tyr | Glu | Asn | Asp | Leu | Leu | Ser | Tyr | Val | Trp | Ser | Arg | Trp | Lys |
|---|---|---|---|---|---|---|---|---|---|---|---|---|---|---|
| | | | | 740 | | | | | 745 | | | | | 750 |

| Glu | Gly | Arg | Ala | Leu | Glu | Ile | Val | Asp | Pro | Val | Ile | Val | Asp | Ser |
|---|---|---|---|---|---|---|---|---|---|---|---|---|---|---|
| | | | | 755 | | | | | 760 | | | | | 765 |

| Leu | Ser | Ser | Gln | Pro | Ser | Ile | Phe | Gln | Pro | Gln | Glu | Val | Leu | Lys |
|---|---|---|---|---|---|---|---|---|---|---|---|---|---|---|
| | | | | 770 | | | | | 775 | | | | | 780 |

| Cys | Ile | Gln | Ile | Gly | Leu | Leu | Cys | Val | Gln | Glu | Leu | Ala | Glu | His |
|---|---|---|---|---|---|---|---|---|---|---|---|---|---|---|
| | | | | 785 | | | | | 790 | | | | | 795 |

| Arg | Pro | Ala | Met | Ser | Ser | Val | Val | Trp | Met | Phe | Gly | Ser | Glu | Ala |
|---|---|---|---|---|---|---|---|---|---|---|---|---|---|---|
| | | | | 800 | | | | | 805 | | | | | 810 |

| Thr | Glu | Ile | Pro | Gln | Pro | Lys | Pro | Pro | Gly | Tyr | Cys | Val | Arg | Arg |
|---|---|---|---|---|---|---|---|---|---|---|---|---|---|---|
| | | | | 815 | | | | | 820 | | | | | 825 |

| Ser | Pro | Tyr | Glu | Leu | Asp | Pro | Ser | Ser | Ser | Trp | Gln | Cys | Asp | Glu |
|---|---|---|---|---|---|---|---|---|---|---|---|---|---|---|
| | | | | 830 | | | | | 835 | | | | | 840 |

| Asn | Glu | Ser | Trp | Thr | Val | Asn | Gln | Tyr | Thr | Cys | Ser | Val | Ile | Asp |
|---|---|---|---|---|---|---|---|---|---|---|---|---|---|---|
| | | | | 845 | | | | | 850 | | | | | 855 |

Ala Arg ( 2 ) INFORMATION FOR SEQ ID NO: 3:

( i ) SEQUENCE CHARACTERISTICS:
    ( A ) LENGTH: 857 base pairs
    ( B ) TYPE: amino acid
    ( D ) TOPOLOGY: linear ( i i ) MOLECULE TYPE: peptide ( x i ) SEQUENCE DESCRIPTION: SEQ ID NO:3:

| Met | Lys | Gly | Val | Gln | Asn | Ile | Tyr | His | His | Ser | Tyr | Thr | Phe | Ser |
|---|---|---|---|---|---|---|---|---|---|---|---|---|---|---|
| | | | | 5 | | | | | 10 | | | | | 15 |

| Phe | Leu | Leu | Val | Phe | Leu | Val | Leu | Ile | Leu | Phe | His | Pro | Ala | Leu |
|---|---|---|---|---|---|---|---|---|---|---|---|---|---|---|
| | | | | 20 | | | | | 25 | | | | | 30 |

| Ser | Ile | Tyr | Val | Asn | Thr | Leu | Ser | Ser | Ser | Glu | Ser | Leu | Thr | Ile |
|---|---|---|---|---|---|---|---|---|---|---|---|---|---|---|
| | | | | 35 | | | | | 40 | | | | | 45 |

| Ser | Ser | Asn | Arg | Thr | Leu | Val | Ser | Pro | Gly | Gly | Val | Phe | Glu | Leu |
|---|---|---|---|---|---|---|---|---|---|---|---|---|---|---|
| | | | | 50 | | | | | 55 | | | | | 60 |

| Gly | Phe | Phe | Lys | Pro | Leu | Gly | Arg | Ser | Arg | Trp | Tyr | Leu | Gly | Ile |
|---|---|---|---|---|---|---|---|---|---|---|---|---|---|---|
| | | | | 65 | | | | | 70 | | | | | 75 |

| Trp | Tyr | Lys | Lys | Ala | Pro | Trp | Lys | Thr | Tyr | Ala | Trp | Val | Ala | Asn |
|---|---|---|---|---|---|---|---|---|---|---|---|---|---|---|
| | | | | 80 | | | | | 85 | | | | | 90 |

| Arg | Asp | Asn | Pro | Leu | Ser | Ser | Ser | Ile | Gly | Thr | Leu | Lys | Ile | Ser |
|---|---|---|---|---|---|---|---|---|---|---|---|---|---|---|
| | | | | 95 | | | | | 100 | | | | | 105 |

```
Gly Asn Asn Leu Val Leu Leu Ser Gln Ser Thr Asn Thr Val Trp
            110                 115                 120
Ser Thr Asn Leu Thr Arg Gly Asn Ala Arg Ser Pro Val Ile Ala
            125                 130                 135
Glu Leu Leu Pro Asn Gly Asn Phe Val Ile Arg His Ser Asn Val
            140                 145                 150
Asn Lys Asp Ser Ser Gly Phe Leu Trp Gln Ser Phe Asp Phe Pro
            155                 160                 165
Thr Asp Thr Leu Leu Pro Glu Met Lys Leu Gly Tyr Asp Leu Lys
            170                 175                 180
Thr Gly Arg Asn Arg Phe Leu Thr Ser Trp Lys Gly Ser Asp Asp
            185                 190                 195
Pro Ser Ser Gly Asn Phe Val Tyr Lys Leu Asp Ile Arg Arg Gly
            200                 205                 210
Leu Pro Glu Phe Ile Leu Ile Asn Gln Phe Leu Asn Gln Arg Val
            215                 220                 225
Glu Thr Gln Arg Ser Gly Pro Trp Asn Gly Met Glu Phe Ser Gly
            230                 235                 240
Ile Pro Glu Val Gln Gly Leu Asn Tyr Met Val Tyr Asn Tyr Thr
            245                 250                 255
Glu Asn Ser Glu Glu Ile Ala Tyr Ser Phe His Met Thr Asn Gln
            260                 265                 270
Ser Ile Tyr Ser Arg Leu Thr Leu Val Ser Glu Leu Thr Leu Asp
            275                 280                 285
Arg Leu Thr Trp Ile Pro Pro Ser Arg Asp Trp Trp Ser Leu Phe
            290                 295                 300
Trp Thr Leu Pro Thr Asp Val Cys Asp Pro Leu Tyr Leu Cys Gly
            305                 310                 315
Ser Tyr Ser Tyr Cys Asp Leu Ile Thr Ser Pro Asn Cys Asn Cys
            320                 325                 330
Ile Arg Gly Phe Val Pro Lys Asn Pro Gln Gln Trp Asp Leu Arg
            335                 340                 345
Asp Gly Thr Arg Gly Cys Val Arg Thr Thr Gln Met Ser Cys Ser
            350                 355                 360
Gly Asp Gly Phe Leu Arg Leu Asn Asn Met Asn Leu Pro Asp Thr
            365                 370                 375
Lys Thr Ala Thr Val Asp Arg Thr Met Asp Val Lys Lys Cys Glu
            380                 385                 390
Glu Arg Cys Leu Ser Asp Cys Asn Cys Thr Ser Phe Ala Ile Ala
            395                 400                 405
Asp Val Arg Asn Gly Gly Leu Gly Cys Val Phe Trp Thr Gly Glu
            410                 415                 420
Leu Val Ala Ile Arg Lys Phe Ala Val Gly Gly Gln Asp Leu Tyr
            425                 430                 435
Val Arg Leu Asn Ala Ala Asp Leu Asp Ile Ser Ser Gly Glu Lys
            440                 445                 450
Arg Asp Arg Thr Gly Lys Ile Ile Gly Trp Ser Ile Gly Ser Ser
            455                 460                 465
Val Met Leu Ile Leu Ser Val Ile Leu Phe Cys Phe Trp Arg Arg
            470                 475                 480
Arg Gln Lys Gln Ala Lys Ala Asp Ala Thr Pro Ile Val Asn Asn
            485                 490                 495
Gln Val Leu Met Asn Glu Val Val Leu Pro Arg Lys Lys Arg Asn
```

|       |       |       |       | 500   |       |       |       | 505   |       |       |       | 510   |
|-------|-------|-------|-------|-------|-------|-------|-------|-------|-------|-------|-------|-------|
| Phe   | Ser   | Gly   | Glu   | Asp   | Asp   | Val   | Glu   | Asn   | Leu   | Glu   | Leu   | Pro   | Leu | Met |

Phe Ser Gly Glu Asp Asp Val Glu Asn Leu Glu Leu Pro Leu Met
        515                     520                     525

Glu Phe Glu Ala Val Val Thr Ala Thr Glu His Phe Ser Asp Phe
        530                     535                     540

Asn Lys Val Gly Lys Gly Gly Phe Gly Val Val Tyr Lys Gly Arg
        545                     550                     555

Leu Val Asp Gly Gln Glu Ile Ala Val Lys Arg Leu Ser Glu Met
        560                     565                     570

Ser Ala Gln Gly Thr Asp Glu Phe Met Asn Glu Val Arg Leu Met
        575                     580                     585

Gln Ser Phe Ser His Asn Asn Leu Val Arg Leu Leu Gly Cys Cys
        590                     595                     600

Val Tyr Glu Gly Glu Lys Ile Leu Ile Tyr Glu Tyr Leu Glu Asn
        605                     610                     615

Leu Ser Leu Asp Ser His Leu Asp Glu Thr Arg Ser Cys Met Leu
        620                     625                     630

Asn Trp Gln Met Arg Phe Asp Ile Ile Asn Gly Ile Ala Arg Gly
        635                     640                     645

Leu Leu Tyr Leu His Gln Asp Ser Arg Phe Arg Ile Ile His Arg
        650                     655                     660

Asp Leu Lys Ala Ser Asn Val Leu Leu Asp Lys Asp Met Thr Pro
        665                     670                     675

Lys Ile Ser Asp Phe Gly Met Ala Arg Ile Phe Gly Arg Asp Glu
        680                     685                     690

Thr Glu Ala Asp Thr Arg Lys Val Val Gly Thr Tyr Gly Tyr Met
        695                     700                     705

Ser Pro Glu Tyr Ala Met Asn Gly Thr Phe Ser Met Lys Ser Asp
        710                     715                     720

Val Phe Ser Phe Gly Val Ile Leu Leu Glu Ile Ile Ser Gly Lys
        725                     730                     735

Arg Asn Lys Gly Leu Cys Asp Leu Asp Ser Ser Leu Asn Leu Leu
        740                     745                     750

Gly Cys Val Trp Arg Asn Trp Lys Glu Gly Gln Gly Leu Glu Ile
        755                     760                     765

Val Asp Lys Val Ile Ile Asp Ser Ser Ser Pro Thr Phe Arg Pro
        770                     775                     780

Arg Glu Ile Leu Arg Cys Leu Gln Ile Gly Leu Leu Cys Val Gln
        785                     790                     795

Glu Arg Val Glu Asp Arg Pro Met Met Ser Ser Val Val Leu Met
        800                     805                     810

Leu Gly Ser Glu Ala Ala Leu Ile Pro Gln Pro Lys Gln Pro Gly
        815                     820                     825

Tyr Cys Val Ser Gly Ser Ser Leu Glu Thr Tyr Ser Arg Arg Asp
        830                     835                     840

Asp Glu Asn Cys Thr Val Asn Gln Ile Thr Met Ser Ile Ile Asp
        845                     850                     855

Ala Arg ( 2 ) INFORMATION FOR SEQ ID NO: 4:

( i ) SEQUENCE CHARACTERISTICS:
        ( A ) LENGTH: 2749 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:4:

| | | | | | | | | | | | | | | | | |
|---|---|---|---|---|---|---|---|---|---|---|---|---|---|---|---|---|
| ATG | AAA | GGG | GTA | CAG | AAC | ATT | TAC | CAC | CAT | TCT | TAC | ACC | TTC | TCG | TTC | TTG | 51 |
| CTA | GTC | TTC | CTT | GTC | TTG | ATT | CTA | TTT | CAT | CCT | GCC | CTT | TCG | ATC | TAT | GTC | 102 |
| AAC | ACT | TTA | TCG | TCT | TCA | GAG | TCT | CTC | ACA | ATC | TCG | AGC | AAT | AGA | ACA | CTT | 153 |
| GTA | TCT | CCC | GGT | GGA | GTC | TTC | GAG | CTT | GGT | TTC | TTC | AAA | CCC | TTG | GGA | CGC | 204 |
| TCG | CGA | TGG | TAT | CTG | GGA | ATA | TGG | TAT | AAA | AAA | GCC | CCC | TGG | AAA | ACC | TAC | 255 |
| GCA | TGG | GTC | GCC | AAC | AGA | GAC | AAC | CCT | CTC | TCC | AGT | TCT | ATT | GGA | ACC | CTC | 306 |
| AAA | ATC | TCT | GGC | AAC | AAT | CTT | GTC | CTG | CTA | AGT | CAG | TCT | ACT | AAC | ACT | GTT | 357 |
| TGG | TCG | ACA | AAT | CTT | ACT | AGA | GGA | AAT | GCG | AGA | TCT | CCG | GTG | ATA | GCA | GAG | 408 |
| CTT | CTT | CCC | AAC | GGT | AAT | TTT | GTA | ATA | AGA | CAC | TCC | AAC | AAC | AAA | GAC | TCA | 459 |
| AGT | GGA | TTC | TTG | TGG | CAG | AGT | TTC | GAT | TTT | CCG | ACA | GAT | ACT | TTA | CTT | CCG | 510 |
| GAG | ATG | AAA | CTA | GGT | TAC | GAT | CTC | AAA | ACA | GGG | CGC | AAC | AGG | TTC | CTT | ACA | 561 |
| TCG | TGG | AAA | GGT | TCA | GAT | GAT | CCG | TCA | AGC | GGG | AAT | TTC | GTG | TAC | AAA | CTC | 612 |
| GAC | ATT | CGA | AGG | GGA | TTG | CCT | GAG | TTT | ATT | CTT | ATA | AAT | CAA | TTT | TTG | AAT | 663 |
| CAA | CGT | GTT | GAA | ACG | CAA | AGG | AGC | GGT | CCT | TGG | AAT | GGA | ATG | GAG | TTT | AGT | 714 |
| GGC | ATA | CCG | GAG | GTG | CAG | GGA | TTA | AAT | TAC | ATG | GTT | TAC | AAT | TAT | ACG | GAG | 765 |
| AAC | AGT | GAG | GAG | ATC | GCT | TAC | TCG | TTC | CAT | ATG | ACC | AAC | CAA | AGC | ATC | TAC | 816 |
| TCC | AGA | TTG | ACA | GTC | AGT | GAG | TTG | ACA | CTC | GAT | CGA | TTG | ACG | TGG | ATC | CCG | 867 |
| CCA | TCA | CGG | GAT | TGG | AGC | CTC | TTC | TGG | ACT | TTA | CCA | ACG | GAC | GTG | TGC | GAT | 918 |
| CCG | CTT | TAC | TTA | TGT | GGA | TCT | TAT | TCT | TAC | TGT | GAC | CTA | ATT | ACG | TCA | CCT | 969 |
| AAC | TGT | AAC | TGT | ATT | AGA | GGG | TTC | GTT | CCC | AAG | AAC | CCG | CAG | CAG | TGG | GAC | 1020 |
| TTG | AGA | GAC | GGA | ACA | CGG | GGG | TGT | GTG | AGG | ACG | ACG | CAG | ATG | AGC | TGT | AGT | 1071 |
| GGA | GAT | GGG | TTT | TTG | CGG | CTA | AAC | AAT | ATG | AAT | TTG | CCG | GAT | ACT | AAG | ACG | 1122 |
| GCA | ACT | GTG | GAT | CGG | ACA | ATG | GAT | GTG | AAA | AAA | TGT | GAA | GAG | AGG | TGT | CTT | 1173 |
| AGC | GAT | TGT | AAC | TGT | ACT | TCG | TTT | GCT | ATT | GCG | GAT | GTT | CGG | AAT | GGA | GGA | 1224 |
| TTG | GGT | TGT | GTG | TTT | TGG | ACC | GGA | GAG | CTC | GTT | GCG | ATC | AGG | AAA | TTC | GCC | 1275 |
| GTC | GGT | GGT | CAA | GAT | CTT | TAC | GTC | AGA | TTG | AAT | GCT | GCT | GAT | CTA | GAT | ATT | 1326 |
| TCC | TCG | GGT | GAG | AAG | AGA | GAC | CGA | ACT | GGA | AAA | ATC | ATA | GGT | TGG | AGT | ATT | 1377 |
| GGA | TCC | AGC | GTT | ATG | CTT | ATT | CTG | AGT | GTT | ATC | TTG | TTC | TGC | TTT | TGG | AGG | 1428 |
| AGG | AGA | CAA | AAG | CAA | GCA | AAA | GCA | GAT | GCA | ACA | CCT | ATT | GTG | GAA | AAT | CAA | 1479 |
| GTT | CTA | ATG | AAC | GAG | GTG | GTG | TTA | CCA | AGA | AAG | AAG | AGA | AAT | TTT | TCT | GGA | 1530 |
| GAG | GAC | GAT | GTA | GAA | AAT | TTG | GAA | CTT | CCA | TTG | ATG | GAG | TTT | GAA | GCT | GTT | 1581 |
| GTC | ACA | GCC | ACC | GAA | CAT | TTC | TCT | GAT | TTT | AAC | AAG | GTC | GGA | AAA | GGT | GGT | 1632 |
| TTT | GGT | GTT | GTT | TAC | AAG | GGA | AGG | TTA | GTT | GAC | GGG | CAA | GAA | ATT | GCA | GTG | 1683 |
| AAG | AGA | CTA | TCG | GAA | ATG | TCA | GCT | CAA | GGT | ACC | GAT | GAG | TTC | ATG | AAC | GAA | 1734 |
| GTT | AGG | CTA | ATG | CAA | AGC | TTC | AGC | CAC | AAT | AAT | CTT | GTC | CGA | CTT | CTT | GGC | 1785 |
| TGT | TGT | GTT | TAT | GAG | GGC | GAG | AAG | ATC | TTA | ATT | TAC | GAG | TAC | TTG | GAG | AAT | 1836 |
| CTA | AGC | CTC | GAT | TCT | CAT | CTC | TTT | GAT | GAA | ACC | AGA | AGC | TGT | ATG | TTA | AAT | 1887 |

| | | | | | | | | | | | | | | | | |
|---|---|---|---|---|---|---|---|---|---|---|---|---|---|---|---|---|
|TGG|CAA|ATG|AGA|TTT|GAT|ATT|ATC|AAT|GGT|ATT|GCC|CGA|GGG|CTT|CTC|TAT|1938|
|CTT|CAC|CAA|GAT|TCA|CGG|TTT|AGA|ATC|ATC|CAC|AGG|GAT|TTG|AAA|GCA|AGC|1989|
|AAT|GTC|TTG|CTT|GAT|AAA|GAT|ATG|ACT|CCA|AAA|ATT|TCA|GAC|TTT|GGA|ATG|2040|
|GCT|AGG|ATC|TTT|GGA|CGG|GAT|GAG|ACG|GAA|GCT|GAC|ACG|AGG|AAG|GTG|GTC|2091|
|GGA|ACT|TAT|GGC|TAC|ATG|TCT|CCA|GAA|TAT|GCG|ATG|AAC|GGG|ACA|TTC|TCA|2142|
|ATG|AAG|TCA|GAT|GTG|TTC|AGT|TTT|GGG|GTC|TTG|CTT|CTT|GAA|ATT|ATA|AGT|2193|
|GGC|AAG|AGG|AAC|AAA|GGC|TTA|TGC|GAC|TCG|GAT|AGT|AGC|CTT|AAT|CTT|CTC|2244|
|GGA|TGT|GTA|TGG|AGG|AAT|TGG|AAA|GAA|GGT|CAA|GGT|CTA|GAG|ATA|GTA|GAC|2295|
|AAG|GTC|ATC|ATA|GAT|TCT|TCA|TCA|CCA|ACG|TTC|AGG|CCA|CGT|GAA|ATC|TTA|2346|
|AGA|TGC|TTA|CAA|ATT|GGC|CTC|TTG|TGT|GTT|CAA|GAA|CGT|GTG|GAG|GAT|AGA|2397|
|CCA|ATG|ATG|TCG|TCA|GTA|GTT|TTG|ATG|CTC|GGA|AGT|GAA|GCT|GCA|TTG|ATT|2448|
|CCT|CAA|CCT|AAA|CAG|CCA|GGA|TAT|TGC|GTC|AGC|GGA|AGT|CTT|CTT|GAA|ACT|2499|
|TAT|TCT|AGG|CGT|GAC|GAT|GAA|AAT|TGC|ACA|GTG|AAC|CAA|ATC|ACC|ATG|TCG|2550|
|ATC|ATT|GAC|GCT|CGG|TAA|TAT|GAT|AGT|CTT|TGA|TAA|TAT|TCT|CAC|TAT|TAA|2601|
|AGT|TTT|ACT|AAA|TGG|AAA|AAA|AGA|GTT|TTA|CAA|GTT|GAG|TGA|CAA|AGC|GTG|2652|
|CCA|AAC|TCT|TCA|GTC|TAT|CGA|AAT|TTT|CAT|TCA|TCC|TCT|GTA|TAT|TCT|CTC|2703|
|GAA|TTG|GTT|TCG|TTA|TTT|CGA|GTC|AAT|TCA|CAG|TCA|ACA|ACT|GCA|G| |2749|

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Asp Leu Lys Val Ser Asn
               5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Gly Thr Tyr Gly Tyr Met Ser Pro Glu
               5

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

ACTTGTGGCA AAGCTTCGAT T                  21

5,484,905

63

64

-continued ( 2 ) INFORMATION FOR SEQ ID NO: 8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

```
CCATCCCGAA  TTCCGAGATC  T                                              21
```

( 2 ) INFORMATION FOR SEQ ID NO: 9:

( i ) SEQUENCE CHARACTERISTICS:
        ( A ) LENGTH: 2571 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
ATG  AAA  GGT  GCA  CGA  AAC  ATC  TAT  CAC  CAT  TCT  TAC  ATG          39
TCC  TTT  TTG  CTC  GTC  TTC  GTT  GTC  ATG  ATT  CTA  ATT  CAT          78
CCT  GCC  CTT  TCG  ATC  TAT  ATC  AAC  ACT  TTG  TCG  TCT  ACA         117
GAA  TCT  CTT  ACA  ATC  TCA  AGC  AAC  AAA  ACA  CTT  GTA  TCT         156
CCC  GGT  AGT  ATC  TTC  GAG  GTC  GGC  TTC  TTC  AGA  ACC  AAT         195
TCT  CGT  TGG  TAT  CTC  GGG  ATG  TGG  TAC  AAG  AAA  GTG  TCC         234
GAC  AGA  ACC  TAT  GTA  TGG  GTT  GCC  AAC  AGA  GAT  AAC  CCA         273
CTC  TCC  AAT  GCC  ATT  GGA  ACC  CTC  AAA  ATC  TCA  GGC  AAT         312
AAT  CTT  GTC  CTC  CTT  GAT  CAC  TCC  AAT  AAA  CCT  GTT  TGG         351
TGG  ACG  AAT  CTT  ACT  AGA  GGA  AAT  GAG  AGA  TCT  CCG  GTG         390
GTG  GCT  GAG  CTT  CTC  GCT  AAC  GGA  AAC  TTC  GTG  ATG  CGA         429
GAC  TCC  AGT  AAC  AAC  GAC  GCA  AGT  GAA  TAC  TTG  TGG  CAA         468
AGT  TTC  GAT  TAC  CCT  ACG  GAT  ACT  TTG  CTT  CCA  GAG  ATG         507
AAA  CTG  GGT  TAC  AAC  CTC  AAA  ACA  GGG  TTG  AAC  AGG  TTC         546
CTT  ACA  TCA  TGG  AGA  AGT  TCA  GAT  GAT  CCA  TCA  AGC  GGG         585
AAT  TTC  TCG  TAC  AAG  CTC  GAA  ACC  CAA  AGT  CTT  CCT  GAG         624
TTT  TAT  CTA  TCG  CGG  GAG  AAC  TTT  CCA  ATG  CAT  CGG  AGT         663
GGT  CCA  TGG  AAT  GGA  ATC  CGA  TTT  AGT  GGC  ATA  CCA  GAG         702
GAC  CAA  AAG  CTG  AGT  TAC  ATG  GTG  TAC  AAT  TTC  ATA  GAG         741
AAT  AAT  GAA  GAG  GTC  GCT  TAT  ACA  TTC  CGA  ATG  ACC  AAC         780
AAC  AGC  TTC  TAC  TCG  AGA  TTG  ACA  CTA  ATT  TCC  GAA  GGG         819
TAT  TTT  CAG  CGA  CTG  ACG  TGG  TAT  CCG  TCA  ATA  AGG  ATA         858
TGG  AAC  AGG  TTC  TGG  TCT  TCT  CCA  GTG  GAC  CCC  CAG  TGT         897
GAT  ACT  TAC  ATA  ATG  TGT  GGA  CCT  TAC  GCT  TAC  TGT  GAC         936
GTG  AAC  ACA  TCA  CCG  GTT  TGT  AAC  TGT  ATC  CAA  GGG  TTC         975
AAT  CCC  CGG  AAT  ATA  CAG  CAG  TGG  GAT  CAG  AGA  GTC  TGG        1014
```

```
GCA GGT GGG TGT ATA AGG AGG ACG CAG CTT AGC TGC AGT                1053
GGA GAT GGT TTT ACC AGG ATG AAG AAG ATG AAG TTG CCA                1092
GAA ACT ACG ATG GCG ACT GTC GAC CGT AGT ATT GGT GTG                1131
AAA GAA TGT AAG AAG AGG TGC ATT AGC GAT TGT AAT TGT                1170
ACC GCT TTT GCA AAT GCA GAT ATC CGG AAT GGT GGG TCG                1209
GGT TGT GTG ATT TGG ACC GAA CGC CTT GAG GAT ATC CGG                1248
AAT TAC GCT ACT GAC GCT ATT GAC GGT CAA GAT CTT TAT                1287
GTC AGA TTG GCT GCA GCT GAT ATC GCT AAG AAG AGA AAC                1326
GCG AGT GGG AAA ATT ATA AGT TTG ACT GTT GGT GTT AGT                1365
GTT CTG CTT CTG CTG ATC ATG TTC TGC CTC TGG AAA AGA                1404
AAA CAA AAG CGA GCA AAA GCA AGT GCA ATA TCC ATT GCA                1443
AAT ACA CAG AGA AAC CAA AAC TTG CCT ATG AAC GAG ATG                1482
GTA CTA TCA AGC AAG AGA GAG TTT TCT GGA GAG TAC AAA                1521
TTT GAG GAA CTG GAA CTT CCA TTG ATA GAG ATG GAA ACT                1560
GTT GTC AAA GCC ACC GAA AAT TTC TCC AGC TGT AAC AAA                1599
CTC GGA CAA GGT GGT TTT GGT ATT GTT TAC AAG GGA AGA                1638
TTA CTT GAC GGG AAA GAA ATT GCA GTA AAA AGG CTA TCA                1677
AAG ACG TCA GTT CAA GGG ACT GAT GAG TTT ATG AAT GAG                1716
GTG ACA CTA ATT GCG AGG CTT CAG CAT ATA AAC CTT GTT                1755
CAA GTT CTT GGC TGT TGC ATT GAA GGA GAT GAG AAG ATG                1794
TTG ATA TAT GAG TAT TTG GAA AAT TTA AGC CTT GAT TCT                1833
TAT CTC TTT GGT AAA ACC CGA AGG TCT AAG CTA AAT TGG                1872
AAT GAG AGA TTC GAC ATT ACC AAT GGT GTT GCT CGA GGG                1911
CTT TTA TAT CTT CAT CAA GAC TCA CGG TTT AGG ATA ATC                1950
CAC AGA GAT TTG AAA GTA AGT AAC ATT TTG CTT GAC AAA                1989
AAT ATG ATC CCA AAG ATC TCG GAT TTT GGG ATG GCC AGG                2028
ATA TTT GAA AGG GAC GAA ACG GAA GCT AAC ACA ATG AAG                2067
GTG GTC GGA ACA TAC GGC TAC ATG TCC CCG GAA TAC GCA                2106
ATG TAT GGG ATA TTC TCG GAA AAA TCA GAT GTT TTC AGT                2145
TTT GGA GTC ATA GTT CTT GAA ATT GTT AGT GGA AAG AAG                2184
AAC AGA GGA TTC TAC AAC TTG GAC TAC GAA AAC GAT CTC                2223
CTA AGC TAT GTA TGG AGT CGT TGG AAG GAA GGA AGA GCG                2262
CTA GAA ATC GTA GAT CCC GTC ATC GTA GAT TCA CTG TCA                2301
TCA CAG CCA TCA ATA TTT CAA CCA CAA GAA GTC CTA AAA                2340
TGT ATT CAA ATT GGT CTC TTG TGT GTT CAA GAA CTT GCA                2379
GAG CAC AGA CCA GCG ATG TCG TCT GTG GTT TGG ATG TTT                2418
GGA AGT GAA GCA ACA GAG ATT CCT CAG CCT AAA CCG CCA                2457
GGT TAT TGC GTC AGA AGA AGT CCT TAT GAA CTT GAT CCT                2496
TCA TCA AGT TGG CAA TGT GAC GAA AAT GAA TCC TGG ACG                2535
GTG AAC CAG TAC ACC TGC TCA GTC ATT GAT GCC CGG                    2571
```

Thus, while we have illustrated and described the preferred embodiment of our invention, it is to be understood that this invention is capable of variation and modification and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and process of making and using it in such full, clear, concise and exact terms so as to enable any person skilled in the art to which it pertains, or with which it is most nearly connected, to make and use the same;

We claim:

1. An isolated DNA fragment from the genus Brassica, which DNA fragment encodes an S receptor kinase and has a nucleotide sequence as follows:

```
1     ATG AAA GGT GCA CGA AAC
                          ATC TAT CAC CAT TCT TAC ATG
40    TCC TTT TTG CTC GTC TTC
                          GTT GTC ATG ATT CTA ATT CAT
79    CCT GCC CTT TCG ATC TAT
                          ATC AAC ACT TTG TCG TCT ACA
118   GAA TCT CTT ACA ATC TCA
                          AGC AAC AAA ACA CTT GTA TCT
157   CCC GGT AGT ATC TTC GAG
                          GTC GGC TTC TTC AGA ACC AAT
196   TCT CGT TGG TAT CTC GGG
                          ATG TGG TAC AAG AAA GTG TCC
235   GAC AGA ACC TAT GTA TGG
                          GTT GCC AAC AGA GAT AAC CCA
274   CTC TCC AAT GCC ATT GGA
                          ACC CTC AAA ATC TCA GGC AAT
313   AAT CTT GTC CTC CTT GAT
                          CAC TCC AAT AAA CCT GTT TGG
352   TGG ACG AAT CTT ACT AGA
                          GGA AAT GAG AGA TCT CCG GTG
391   GTG GCT GAG CTT CTC GCT
                          AAC GGA AAC TTC GTG ATG CGA
430   GAC TCC AGT AAC AAC GAC
                          GCA AGT GAA TAC TTG TGG CAA
469   AGT TTC GAT TAC CCT ACG
                          GAT ACT TTG CTT CCA GAG ATG
508   AAA CTG GGT TAC AAC CTC
                          AAA ACA GGG TTG AAC AGG TTC
547   CTT ACA TCA TGG AGA AGT
                          TCA GAT GAT CCA TCA AGC GGG
586   AAT TTC TCG TAC AAG CTC
                          GAA ACC AAA GT CCT CCT GAG
625   TTT TAT CTA TCG CGG GAG
                          AAC TTT CCA ATG CAT CGG AGT
664   GGT CCA TGG AAT GGA ATC
                          CGA TTT AGT GGC ATA CCA GAG
703   GAC CAA AAG CTG AGT TAC
                          ATG GTG TAC AAT TTC ATA GAG
742   AAT AAT GAA GAG GTC GCT
                          TAT ACA TTC CGA ATG ACC AAC
781   AAC AGC TTC TAC TCG AGA
                          TTG ACA CTA ATT TCC GAA GGG
820   TAT TTT CAG CGA CTG ACG
                          TGG TAT CCG TCA ATA AGG ATA
859   TGG AAC AGG TTC TGG TCT
                          TCT CCA GTG GAC CCC CAG TGT
898   GAT ACT TAC ATA ATG TGT
                          GGA CCT TAC GCT TAC TGT GAC
937   GTG AAC ACA TCA CCG GTT
                          TGT AAC TGT ATC CAA GGG TTC
976   AAT CCC CGG AAT ATA CAG
                          CAG TGG GAT CAG AGA GTC TGG
1015  GCA GGT GGG TGT ATA AGG
                          AGG ACG CAG CTT AGC TGC AGT
1054  GGA GAT GGT TTT ACC AGG
                          ATG AAG AAG ATG AAG TTG CCA
1093  GAA ACT ACG ATG GCG ACT
                          GTC GAC CGT AGT ATT GGT GTG
1132  AAA GAA TGT AAG AAG AGG
                          TGC ATT AGC GAT TGT AAT TGT
1171  ACC GCT TTT GCA AAT GCA
                          GAT ATC CGG AAT GGT GGG TCG
1210  GGT TGT GTG ATT TGG ACC
                          GAA CGC TTG AGG ATA TCG G
1249  AAT TAC GCT ACT GAC GCT
                          ATT GAC GGT CAA GAT CTT TAT
1288  GTC AGA TTG GCT GCA GCT
                          GAT ATC GCT AAG AAG AGA AAC
1327  GCG AGT GGG AAA ATT ATA
                          AGT TTG ACT GTT GGT GTT AGT
1366  GTT CTG CTT CTG CTG ATC
                          ATG TTC TGC CTC TGG AAA AGA
1405  AAA CAA AAG CGA GCA AAA
                          GCA AGT GCA ATA TCC ATT GCA
1444  AAT ACA CAG AGA AAC CAA
                          AAC TTG CCT ATG AAC GAG ATG
1493  GTA CTA TCA AGC AAG AGA
                          GAG TTT CT GGA GAG TAC AAA
1522  TTT GAG GAA CTG GAA CTT
                          CCA TTG ATA GAG ATG GAA ACT
1561  GTT GTC AAA GCC ACC GAA
                          AAT TTC TCC AGC TGT AAC AAA
1600  CTC GGA CAA GGT GGT TTT
                          GGT ATT GTT TAC AAG GGA AGA
1639  TTA CTT GAC GGG AAA GAA
                          ATT GCA GTA AAA AGG CTA TCA
1678  AAG ACG TCA GTT CAA GGG
                          ACT GAT GAG TTT ATG AAT GAG
1717  GTG ACA CTA ATT GCG AGG
                          CTT CAG CAT ATA AAC CTT GTT
1756  CAA GTT CTT GGC TGT TGC
```

```
                    ATT GAA GGA GAT GAG AAG ATG                              TTG GAC TAC GAA AAC GAT CTC
1795 TTG ATA TAT GAG TAT TTG                    2224 CTA AGC TAT GTA TGG AGT
                    GAA AAT TTA AGC CTT GAT TCT                              CGT TGG AAG GAA GGA AGA GCG
1834 TAT CTC TTT GGT AAA ACC                    2273 CTA GAA ATC GTA GAT CCC
                    CGA AGG TCT AAG CTA AAT TGG                              GTC ATC GTA GAT TCA CTG TCA
1883 AAT GAG AGA TTC GAC ATT                    2302 TCA CAG CCA TCA ATA TTT
                    ACC AAT GGT GTT GCT CGA GGG                              CAA CCA CAA GAA GTC CTA AAA
1912 CTT TTA TAT CTT CAT CAA                    2341 TGT ATT CAA ATT GGT CTC
                    GAC TCA CGG TTT AGG ATA ATC                              TTG TGT GTT CAA GAA CTT GCA
1951 CAC AGA GAT TTG AAA GTA                    2380 GAG CAC AGA CCA GCG ATG
                    AGT AAC ATT TTG CTT GAC AAA                              TCG TCT GTG GTT TGG ATG TTT
1990 AAT ATG ATC CCA AAG ATC                    2419 GGA AGT GAA GCA ACA GAG
                    TCG GAT TTT GGG ATG GCC AGG                              ATT CCT CAG CCT AAA CCG CCA
2029 ATA TTT GAA AGG GAC GAA                    2458 GGT TAT TGC GTC AGA AGA
                    ACG GAA GCT AAC ACA ATG AAG                              AGT CCT TAT GAA CTT GAT CCT
2068 GTG GTC GGA ACA TAC GGC                    2497 TCA TCA AGT TGG CAA TGT
                    TAC ATG TCC CCG GAA TAC GCA                              GAC GAA AAT GAA TCC TGG ACG
2107 ATG TAT GGG ATA TTC TCG                    2536 GTG AAC CAG TAC ACC TGC
                    GAA AAA TCA GAT GTT TTC AGT                              TCA GTC ATT GAT GCC CGG
2146 TTT GGA GTC ATA GTT CTT
                    GAA ATT GTT AGT GGA AAG AAG
2185 AAC AGA GGA TTC TAC AAC
```

2. An isolated DNA fragment from the genus Brassica, which DNA fragment is capable of expressing in plants a peptide having an amino acid sequence as follows:

| | | | | | | | | | | | | | | |
|---|---|---|---|---|---|---|---|---|---|---|---|---|---|---|
| Met | Lys | Gly | Val | G

-continued

| | | | | | | | | | | | | | |
|---|---|---|---|---|---|---|---|---|---|---|---|---|---|
| | | | | 215 | | | | | 220 | | | | 225 |
| Glu | Thr | Gln | Arg | Ser 230 | Gly | Pro | Trp | Asn | Gly 235 | Met | Glu | Phe | Ser | Gly 240 |
| Ile | Pro | Glu | Val | Gln 245 | Gly | Leu | Asn | Tyr | Met 250 | Val | Tyr | Asn | Tyr | Thr 255 |
| Glu | Asn | Ser | Glu | Glu 260 | Ile | Ala | Tyr | Ser | Phe 265 | His | Met | Thr | Asn | Gln 270 |
| Ser | Ile | Tyr | Ser | Arg 275 | Leu | Thr | Leu | Val | Ser 280 | Glu | Leu | Thr | Leu | Asp 285 |
| Arg | Leu | Thr | Trp | Ile 290 | Pro | Pro | Ser | Arg | Asp 295 | Trp | Trp | Ser | Leu | Phe 300 |
| Trp | Thr | Leu | Pro | Thr 305 | Asp | Val | Cys | Asp | Pro 310 | Leu | Tyr | Leu | Cys | Gly 315 |
| Ser | Tyr | Ser | Tyr | Cys 320 | Asp | Leu | Ile | Thr | Ser 325 | Pro | Asn | Cys | Asn | Cys 330 |
| Ile | Arg | Gly | Phe | Val 335 | Pro | Lys | Asn | Pro | Gln 340 | Gln | Trp | Asp | Leu | Arg 345 |
| Asp | Gly | Thr | Arg | Gly 350 | Cys | Val | Arg | Thr | Thr 355 | Gln | Met | Ser | Cys | Ser 360 |
| Gly | Asp | Gly | Phe | Leu 365 | Arg | Leu | Asn | Asn | Met 370 | Asn | Leu | Pro | Asp | Thr 375 |
| Lys | Thr | Ala | Thr | Val 380 | Asp | Arg | Thr | Met | Asp 385 | Val | Lys | Lys | Cys | Glu 390 |
| Glu | Arg | Cys | Leu | Ser 395 | Asp | Cys | Asn | Cys | Thr 400 | Ser | Phe | Ala | Ile | Ala 405 |
| Asp | Val | Arg | Asn | Gly 410 | Gly | Leu | Gly | Cys | Val 415 | Phe | Trp | Thr | Gly | Glu 420 |
| Leu | Val | Ala | Ile | Arg 425 | Lys | Phe | Ala | Val | Gly 430 | Gly | Gln | Asp | Leu | Tyr 435 |
| Val | Arg | Leu | Asn | Ala 440 | Ala | Asp | Leu | Asp | Ile 445 | Ser | Ser | Gly | Glu | Lys 450 |
| Arg | Asp | Arg | Thr | Gly 455 | Lys | Ile | Ile | Gly | Trp 460 | Ser | Ile | Gly | Ser | Ser 465 |
| Val | Met | Leu | Ile | Leu 470 | Ser | Val | Ile | Leu | Phe 475 | Cys | Phe | Trp | Arg | Arg 480 |
| Arg | Gln | Lys | Gln | Ala 485 | Lys | Ala | Asp | Ala | Thr 490 | Pro | Ile | Val | Asn | Asn 495 |
| Gln | Val | Leu | Met | Asn 500 | Glu | Val | Val | Leu | Pro 505 | Arg | Lys | Lys | Arg | Asn 510 |
| Phe | Ser | Gly | Glu | Asp 515 | Asp | Val | Glu | Asn | Leu 520 | Glu | Leu | Pro | Leu | Met 525 |
| Glu | Phe | Glu | Ala | Val 530 | Val | Thr | Ala | Thr | Glu 535 | His | Phe | Ser | Asp | Phe 540 |
| Asn | Lys | Val | Gly | Lys 545 | Gly | Gly | Phe | Gly | Val 550 | Val | Tyr | Lys | Gly | Arg 555 |
| Leu | Val | Asp | Gly | Gln 560 | Glu | Ile | Ala | Val | Lys 565 | Arg | Leu | Ser | Glu | Met 570 |
| Ser | Ala | Gln | Gly | Thr 575 | Asp | Glu | Phe | Met | Asn 580 | Glu | Val | Arg | Leu | Met 585 |
| Gln | Ser | Phe | Ser | His 590 | Asn | Asn | Leu | Val | Arg 595 | Leu | Leu | Gly | Cys | Cys 600 |
| Val | Tyr | Glu | Gly | Glu 605 | Lys | Ile | Leu | Ile | Tyr 610 | Glu | Tyr | Leu | Glu | Asn 615 |

-continued

| | | | | | | | | | | | | | | |
|---|---|---|---|---|---|---|---|---|---|---|---|---|---|---|
| Leu | Ser | Leu | Asp | Ser 620 | His | Leu | Asp | Glu | Thr 625 | Arg | Ser | Cys | Met | Leu 630 |
| Asn | Trp | Gln | Met | Arg 635 | Phe | Asp | Ile | Ile | Asn 640 | Gly | Ile | Ala | Arg | Gly 645 |
| Leu | Leu | Tyr | Leu | His 650 | Gln | Asp | Ser | Arg | Phe 655 | Arg | Ile | Ile | His | Arg 660 |
| Asp | Leu | Lys | Ala | Ser 665 | Asn | Val | Leu | Leu | Asp 670 | Lys | Asp | Met | Thr | Pro 675 |
| Lys | Ile | Ser | Asp | Phe 680 | Gly | Met | Ala | Arg | Ile 685 | Phe | Gly | Arg | Asp | Glu 690 |
| Thr | Glu | Ala | Asp | Thr 695 | Arg | Lys | Val | Val | Gly 700 | Thr | Tyr | Gly | Tyr | Met 705 |
| Ser | Pro | Glu | Tyr | Ala 710 | Met | Asn | Gly | Thr | Phe 715 | Ser | Met | Lys | Ser | Asp 720 |
| Val | Phe | Ser | Phe | Gly 725 | Val | Ile | Leu | Leu | Glu 730 | Ile | Ile | Ser | Gly | Lys 735 |
| Arg | Asn | Lys | Gly | Leu 740 | Cys | Asp | Leu | Asp | Ser 745 | Ser | Leu | Asn | Leu | Leu 750 |
| Gly | Cys | Val | Trp | Arg 755 | Asn | Trp | Lys | Glu | Gly 760 | Gln | Gly | Leu | Glu | Ile 765 |
| Val | Asp | Lys | Val | Ile 770 | Ile | Asp | Ser | Ser | Ser 775 | Pro | Thr | Phe | Arg | Pro 780 |
| Arg | Glu | Ile | Leu | Arg 785 | Cys | Leu | Gln | Ile | Gly 790 | Leu | Leu | Cys | Val | Gln 795 |
| Glu | Arg | Val | Glu | Asp 800 | Arg | Pro | Met | Met | Ser 805 | Ser | Val | Val | Leu | Met 810 |
| Leu | Gly | Ser | Glu | Ala 815 | Ala | Leu | Ile | Pro | Gln 820 | Pro | Lys | Gln | Pro | Gly 825 |
| Tyr | Cys | Val | Ser | Gly 830 | Ser | Ser | Leu | Glu | Thr 835 | Tyr | Ser | Arg | Arg | Asp 840 |
| Asp | Glu | Asn | Cys | Thr 845 | Val | Asn | Gln | Ile | Thr 850 | Met | Ser | Ile | Ile | Asp 855 |
| Ala | Arg | (SEQ ID NO:3) | | | | | | | | | | | | |

3. An isolated DNA fragment from the genus Brassica, which DNA fragment is capable of expressing in plants a peptide having an amino acid sequence as follows:

| | | | | | | | | | | | | | | |
|---|---|---|---|---|---|---|---|---|---|---|---|---|---|---|
| Met | Lys | Gly | Ala | Arg 5 | Asn | Ile | Tyr | His | His 10 | Ser | Tyr | Met | Ser | Phe 15 |
| Leu | Leu | Val | Phe | Val 20 | Val | Met | Ile | Leu | Ile 25 | His | Pro | Ala | Leu | Ser 30 |
| Ile | Tyr | Ile | Asn | Thr 35 | Leu | Ser | Ser | Thr | Glu 40 | Ser | Leu | Thr | Ile | Ser 45 |
| Ser | Asn | Lys | Thr | Leu 50 | Val | Ser | Pro | Gly | Ser 55 | Ile | Phe | Glu | Val | Gly 60 |
| Phe | Phe | Arg | Thr | Asn 65 | Ser | Arg | Trp | Tyr | Leu 70 | Gly | Met | Trp | Tyr | Lys 75 |
| Lys | Val | Ser | Asp | Arg 80 | Thr | Tyr | Val | Trp | Val 85 | Ala | Asn | Arg | Asp | Asn 90 |
| Pro | Leu | Ser | Asn | Ala 95 | Ile | Gly | Thr | Leu | Lys 100 | Ile | Ser | Gly | Asn | Asn 105 |
| Leu | Val | Leu | Leu | Asp | His | Ser | Asn | Lys | Pro | Val | Trp | Trp | Thr | Asn |

|     |     |     |     | 110 |     |     |     |     | 115 |     |     |     |     | 120 |
| --- | --- | --- | --- | --- | --- | --- | --- | --- | --- | --- | --- | --- | --- | --- |
| Leu | Thr | Arg | Gly | Asn 125 | Glu | Arg | Ser | Pro | Val 130 | Val | Ala | Glu | Leu | Leu 135 |
| Ala | Asn | Gly | Asn | Phe 140 | Val | Met | Arg | Asp | Ser 145 | Ser | Asn | Asn | Asp | Ala 150 |
| Ser | Glu | Tyr | Leu | Trp 155 | Gln | Ser | Phe | Asp | Tyr 160 | Pro | Thr | Asp | Thr | Leu 165 |
| Leu | Pro | Glu | Met | Lys 170 | Leu | Gly | Tyr | Asn | Leu 175 | Lys | Thr | Gly | Leu | Asn 180 |
| Arg | Phe | Leu | Thr | Ser 185 | Trp | Arg | Ser | Ser | Asp 190 | Asp | Pro | Ser | Ser | Gly 195 |
| Asn | Phe | Ser | Tyr | Lys 200 | Leu | Glu | Thr | Gln | Ser 205 | Leu | Pro | Glu | Phe | Tyr 210 |
| Leu | Ser | Arg | Glu | Asn 215 | Phe | Pro | Met | His | Arg 220 | Ser | Gly | Pro | Trp | Asn 225 |
| Gly | Ile | Arg | Phe | Ser 230 | Gly | Ile | Pro | Glu | Asp 235 | Gln | Lys | Leu | Ser | Tyr 240 |
| Met | Val | Tyr | Asn | Phe 245 | Ile | Glu | Asn | Asn | Glu 250 | Glu | Val | Ala | Tyr | Thr 255 |
| Phe | Arg | Met | Thr | Asn 260 | Asn | Ser | Phe | Tyr | Ser 265 | Arg | Leu | Thr | Leu | Ile 270 |
| Ser | Glu | Gly | Tyr | Phe 275 | Gln | Arg | Leu | Thr | Trp 280 | Tyr | Pro | Ser | Ile | Arg 285 |
| Ile | Trp | Asn | Arg | Phe 290 | Trp | Ser | Ser | Pro | Val 295 | Asp | Arg | Gln | Cys | Asp 300 |
| Thr | Tyr | Ile | Met | Cys 305 | Gly | Pro | Tyr | Ala | Tyr 310 | Cys | Asp | Val | Asn | Thr 315 |
| Ser | Pro | Val | Cys | Asn 320 | Cys | Ile | Gln | Gly | Phe 325 | Asn | Pro | Arg | Asn | Ile 330 |
| Gln | Gln | Trp | Asp | Gln 335 | Arg | Val | Trp | Ala | Gly 340 | Gly | Cys | Ile | Arg | Arg 345 |
| Thr | Gln | Leu | Ser | Cys 350 | Ser | Gly | Asp | Gly | Phe 355 | Thr | Arg | Met | Lys | Lys 360 |
| Mrt | Lys | Leu | Pro | Glu 365 | Thr | Thr | Met | Ala | Thr 370 | Val | Asp | Arg | Ser | Ile 375 |
| Gly | Val | Lys | Glu | Cys 380 | Lys | Lys | Arg | Cys | Ile 385 | Ser | Asp | Cys | Asn | Cys 390 |
| Thr | Ala | Phe | Ala | Asn 395 | Ala | Asp | Ile | Arg | Asn 400 | Gly | Gly | Ser | Gly | Cys 405 |
| Val | Ile | Trp | Thr | Glu 410 | Arg | Leu | Glu | Asp | Ile 415 | Arg | Asn | Tyr | Ala | Thr 420 |
| Asp | Ala | Ile | Asp | Gly 425 | Gln | Asp | Leu | Tyr | Val 430 | Arg | Leu | Ala | Ala | Ala 435 |
| Asp | Ile | Ala | Lys | Lys 440 | Arg | Asn | Ala | Ser | Gly 445 | Lys | Ile | Ile | Ser | Leu 450 |
| Thr | Val | Gly | Val | Ser 455 | Val | Leu | Leu | Leu | Leu 460 | Ile | Met | Phe | Cys | Leu 465 |
| Trp | Lys | Arg | Lys | Gln 470 | Lys | Arg | Ala | Lys | Ala 475 | Ser | Ala | Ile | Ser | Ile 480 |
| Ala | Asn | Thr | Gln | Arg 485 | Asn | Gln | Asn | Leu | Pro 490 | Met | Asn | Glu | Met | Val 495 |
| Leu | Ser | Ser | Lys | Arg 500 | Glu | Phe | Ser | Gly | Glu 505 | Tyr | Lys | Phe | Glu | Glu 510 |

| | | | | | | | | | | | | | |
|---|---|---|---|---|---|---|---|---|---|---|---|---|---|
| Leu | Glu | Leu | Pro | Leu 515 | Ile | Glu | Met | Glu | Thr 520 | Val | Val | Lys | Ala | Thr 525 |
| Glu | Asn | Phe | Ser | Ser 530 | Cys | Asn | Lys | Leu | Gly 535 | Gln | Gly | Gly | Phe | Gly 540 |
| Ile | Val | Tyr | Lys | Gly 545 | Arg | Leu | Leu | Asp | Gly 550 | Lys | Glu | Ile | Ala | Val 555 |
| Lys | Arg | Leu | Ser | Lys 560 | Thr | Ser | Val | Gln | Gly 565 | Thr | Asp | Glu | Phe | Met 570 |
| Asn | Glu | Val | Thr | Leu 575 | Ile | Ala | Arg | Leu | Gln 580 | His | Ile | Asn | Leu | Val 585 |
| Gln | Val | Leu | Gly | Cys 590 | Cys | Ile | Glu | Gly | Asp 595 | Glu | Lys | Met | Leu | Ile 600 |
| Tyr | Glu | Tyr | Leu | Glu 605 | Asn | Leu | Ser | Leu | Asp 610 | Ser | Tyr | Leu | Phe | Gly 615 |
| Lys | Thr | Arg | Arg | Ser 620 | Lys | Leu | Asn | Trp | Asn 625 | Glu | Arg | Phe | Asp | Ile 630 |
| Thr | Asn | Gly | Val | Ala 635 | Arg | Gly | Leu | Leu | Tyr 640 | Leu | His | Gln | Asp | Ser 645 |
| Arg | Phe | Arg | Ile | Ile 650 | His | Arg | Asp | Leu | Lys 655 | Val | Ser | Asn | Ile | Leu 660 |
| Leu | Asp | Lys | Asn | Met 665 | Ile | Pro | Lys | Ile | Ser 670 | Asp | Phe | Gly | Met | Ala 675 |
| Arg | Ile | Phe | Glu | Arg 680 | Asp | Glu | Thr | Glu | Ala 685 | Asn | Thr | Met | Lys | Val 690 |
| Val | Gly | Thr | Tyr | Gly 695 | Tyr | Met | Ser | Pro | Glu 700 | Tyr | Ala | Met | Tyr | Gly 705 |
| Ile | Phe | Ser | Glu | Lys 710 | Ser | Asp | Val | Phe | Ser 715 | Phe | Gly | Val | Ile | Val 720 |
| Leu | Glu | Ile | Val | Ser 725 | Gly | Lys | Lys | Asn | Arg 730 | Gly | Phe | Tyr | Asn | Leu 735 |
| Asp | Tyr | Glu | Asn | Asp 740 | Leu | Leu | Ser | Tyr | Val 745 | Trp | Ser | Arg | Trp | Lys 750 |
| Glu | Gly | Arg | Ala | Leu 755 | Glu | Ile | Val | Asp | Pro 760 | Val | Ile | Val | Asp | Ser 765 |
| Leu | Ser | Ser | Gln | Pro 770 | Ser | Ile | Phe | Gln | Pro 775 | Gln | Glu | Val | Leu | Lys 780 |
| Cys | Ile | Gln | Ile | Gly 785 | Leu | Leu | Cys | Val | Gln 790 | Glu | Leu | Ala | Glu | His 795 |
| Arg | Pro | Ala | Met | Ser 800 | Ser | Val | Val | Trp | Met 805 | Phe | Gly | Ser | Glu | Ala 810 |
| Thr | Glu | Ile | Pro | Gln 815 | Pro | Lys | Pro | Pro | Gly 820 | Tyr | Cys | Val | Arg | Arg 825 |
| Ser | Pro | Tyr | Glu | Leu 830 | Asp | Pro | Ser | Ser | Ser 835 | Trp | Gln | Cys | Asp | Glu 840 |
| Asn | Glu | Ser | Trp | Thr 845 | Val | Asn | Gln | Tyr | Thr 850 | Cys | Ser | Val | Ile | Asp 855 |
| Ala | Arg | (SEQ ID NO:2) | | | | | | | | | | | | |

4. An isolated DNA molecule from the genus Brassica, which DNA molecule is an SRK gene which encodes a protein comprising an S-locus binding domain, a transmembrane domain, and a protein kinase domain.

5. An isolated DNA molecule according to claim 4 wherein said S-locus binding domain has about 70% sequence identity with an S-locus binding domain of an SLG gene.

6. An isolated DNA molecule according to claim 5 wherein said S-locus binding domain has a sequence of an S-locus binding domain of an SLG from Brassica or an allelic variant thereof.

7. An isolated DNA molecule according to claim 6 wherein said S-locus binding domain has a sequence of an S-locus binding domain of an SLG selected from the group consisting of Brassica oleracea S2, Brassica oleracea S6, Brassica oleracea S13, Brassica oleracea S14, Brassica oleracea S22, and Brassica campestris S8.

8. An isolated DNA molecule according to claim 4 wherein the DNA encoding the S-locus binding domain is isolated from p281.

9. An isolated DNA molecule according to claim 4 wherein the DNA encoding the S-locus binding domain is isolated from pJN280-1.

10. An isolated DNA molecule according to claim 4 wherein the DNA encoding the kinase domain has 70% sequence identity with the DNA encoding the kinase domain of a gene selected from the group consisting of the SRK6, SRK2, and ZMPK1 genes.

11. An isolated DNA molecule according to claim 4 wherein the DNA encodign the kinase domain is isolated from p281.

12. An isolated DNA molecule according to claim 4 wherein the DNA encoding the kinase domain is isolated from pJN280-1.

| | | | | | | | | | | | | | | | | | |
|---|---|---|---|---|---|---|---|---|---|---|---|---|---|---|---|---|---|
| ATG | AAA | GGG | GTA | CAG | AAC | ATT | TAC | CAC | CAT | TCT | TAC | ACC | TTC | TCG | TTC | TTG | 51 |
| CTA | GTC | TTC | CTT | GTC | TTG | ATT | CTA | TTT | CAT | CCT | GCC | CTT | TCG | ATC | TAT | GTC | 102 |
| AAC | ACT | TTA | TCG | TCT | TCA | GAG | TCT | CTC | ACA | ATC | TCG | AGC | AAT | AGA | ACA | CTT | 153 |
| GTA | TCT | CCC | GGT | GGA | GTC | TTC | GAG | CCT | GGT | TTC | TTC | AAA | CCC | TTG | GGA | CGC | 204 |
| TCG | CGA | TGG | TAT | CTG | GGA | ATA | TGG | TAT | AAA | AAA | GCC | CCC | TGG | AAA | ACC | TAC | 255 |
| GCA | TGG | GTC | GCC | AAC | AGA | GAC | AAC | CCT | CTC | TCC | AGT | TCT | ATT | GGA | ACC | CTC | 306 |
| AAA | ATC | TCT | GGC | AAC | AAT | CTT | GTC | CTG | CTA | AGT | CAG | TCT | ACT | AAC | ACT | GTT | 357 |
| TGG | TCG | ACA | AAT | CTT | ACT | AGA | GGA | AAT | GCG | AGA | TCT | CCG | GTG | ATA | GCA | GAG | 408 |
| CTT | CTT | CCC | AAC | GGT | AAT | TTT | GTA | ATA | AGA | CAC | TCC | AAC | AAC | AAA | GAC | TCA | 459 |
| AGT | GGA | TTC | TTG | TGG | CAG | AGT | TTC | GAT | TTT | CCG | ACA | GAT | ACT | TTA | CTT | CCG | 510 |
| GAG | ATG | AAA | CTA | GGT | TAC | GAT | CTC | AAA | ACA | GGG | CGC | AAC | AGG | TTC | CTT | ACA | 561 |
| TCG | TGG | AAA | GGT | TCA | GAT | GAT | CCG | TCA | AGC | GGG | AAT | TTC | GTG | TAC | AAA | CTC | 612 |
| GAC | ATT | CGA | AGG | GGA | TTG | CCT | GAG | TTT | ATT | CTT | ATA | AAT | CAA | TTT | TTG | AAT | 663 |
| CAA | CGT | GTT | GAA | ACG | CAA | AGG | AGC | GGT | CCT | TGG | AAT | GGA | ATG | GAG | TTT | AGT | 714 |
| GGC | ATA | CCG | GAG | GTG | CAG | GGA | TTA | AAT | TAC | ATG | GTT | TAC | AAT | TAT | ACG | GAG | 765 |
| AAC | AGT | GAG | GAG | ATC | GCT | TAC | TCG | TTC | CAT | ATG | ACC | AAC | CAA | AGC | ATC | TAC | 816 |
| TCC | AGA | TTG | ACA | GTC | AGT | GAG | TTG | ACA | CTC | GAT | CGA | TTG | ACG | TGG | ATC | CCG | 867 |
| CCA | TCA | CGG | GAT | TGG | AGC | CTC | TTC | TGG | ACT | TTA | CCA | ACG | GAC | GTG | TGC | GAT | 918 |
| CCG | CTT | TAC | TTA | TGT | GGA | TCT | TAT | TCT | TAC | TGT | GAC | CTA | ATT | ACG | TCA | CCT | 969 |
| AAC | TGT | AAC | TGT | ATT | AGA | GGG | TTC | GTT | CCC | AAG | AAC | CCG | CAG | CAG | TGG | GAC | 1020 |
| TTG | AGA | GAC | GGA | ACA | CGG | GGG | TGT | GTG | AGG | ACG | ACG | CAG | ATG | AGC | TGT | AGT | 1071 |
| GGA | GAT | GGG | TTT | TTG | CGG | CTA | AAC | AAT | ATG | AAT | TTG | CCG | GAT | ACT | AAG | ACG | 1122 |
| GCA | ACT | GTG | GAT | CGG | ACA | ATG | GAT | GTG | AAA | AAA | TGT | GAA | GAG | AGG | TGT | CTT | 1173 |
| AGC | GAT | TGT | AAC | TGT | ACT | TCG | TTT | GCT | ATT | GCG | GAT | GTT | CGG | AAT | GGA | GGA | 1224 |
| TTG | GGT | TGT | GTG | TTT | TGG | ACC | GGA | GAG | CTC | GTT | GCG | ATC | AGG | AAA | TTC | GCC | 1275 |
| GTC | GGT | GGT | CAA | GAT | CTT | TAC | GTC | AGA | TTG | AAT | GCT | GCT | GAT | CTA | GAT | ATT | 1326 |

-continued

| TCC | TCG | GGT | GAG | AAG | AGA | GAC | CGA | ACT | GGA | AAA | ATC | ATA | GGT | TGG | AGT | ATT | 1377 |
|---|---|---|---|---|---|---|---|---|---|---|---|---|---|---|---|---|---|
| GGA | TCC | AGC | GTT | ATG | CTT | ATT | CTG | AGT | GTT | ATC | ACA | TTC | TGC | TTT | TGG | AGG | 1428 |
| AGG | AGA | CAA | AAG | CAA | GCA | AAA | GCA | GAT | CCA | AAG | ACA | ATT | GTG | GGA | AAT | CAA | 1479 |
| GTT | CTA | ATG | AAC | GTG | GTG | GTG | TTA | CCA | AGA | TTG | AAG | AAT | TCT | TTT | GGA | GTT | 1530 |
| GAG | GAC | GAT | GTA | GAA | AAT | CAT | GAA | CTT | GAT | CCA | ATG | AAG | GAG | GCT | GGT | GAA | 1581 |
| GTC | ACA | GCC | ACC | GAA | CAT | TTC | TCT | GAT | TTT | AAC | GGG | TTA | AAC | GAA | GGT | GTG | 1632 |
| TTT | GGT | GTT | TAC | AAG | AGG | GGA | TCA | TTA | AGG | GCT | GTT | TAC | CAA | GAC | CAT | GCA | 1683 |
| AAG | AGA | CTA | TCG | GAA | ATG | ATG | TCA | CAA | GGT | ACC | ATT | GAT | GGG | ATG | TTC | GAA | 1734 |
| GTT | AGG | CTA | ATG | CAA | AGC | AGC | CGG | CAC | AAT | TTC | CTT | TAC | CGA | CCT | TTG | GGC | 1785 |
| TGT | TGT | GTT | TAT | GAG | GGC | CAT | CAT | TAC | AGA | ACC | ATT | TGT | GAG | TTG | ATG | AAT | 1836 |
| CTA | AGC | CTC | GAT | TCT | TTT | CAT | TT | T GAT | GAA | ACC | ATT | GGG | CTT | GAG | TTA | AAT | 1887 |
| TGG | CAA | ATG | AGA | TTT | TCA | ATT | AIC | AAT | GGT | ATC | CAC | AAA | GCC | CGA | GAG | TAT | 1938 |
| CTT | CAC | CAA | GAT | GAT | CGG | TTT | AGA | ATC | CCA | AAA | AGG | GAT | TCA | GCA | CTC | AGC | 1989 |
| AAT | GTC | TTG | CTT | AAA | CGG | ATG | ATG | ACT | CCA | GAA | ATT | GAC | ACG | TTT | GGA | ATG | 2040 |
| GCT | AGG | ATC | TTT | GGA | CGG | TAC | ATG | GAG | GAG | GCT | ACG | GAA | AAG | ACA | AGG | GTC | 2091 |
| GGA | ACT | TAT | GGC | TAC | ATG | TTC | AGT | TCT | CCA | GAA | TAT | ATG | GAG | GGG | GAA | TTC | ATA | TCA | 2142 |
| ATG | AAG | GTG | TTC | GTA | CCA | TGT | GTT | CTC | TTG | CTT | AGT | GGA | AGT | GCT | TCT | AGT | 2193 |
| GGC | AAG | AGG | AAC | GGC | AAT | GGC | TTA | GGC | AAT | AGT | GGA | GCA | CTT | AAT | CTT | ATT | 2244 |
| GGA | TGT | GTA | TGG | AGG | AAT | AGG | GAT | TGG | GAC | GAA | AAC | GGT | CAA | ATA | GTA | GTA | CTT | 2295 |
| AAG | GTC | ATC | CAT | GAT | GAC | ACG | AGG | GAA | TTC | GTT | CTC | CCA | CGT | GAG | ATC | ATG | 2346 |
| AGA | TGC | TTA | TAT | ATT | GGC | GTA | GGA | TAA | TGA | CAA | C

-continued

| GAA | TTG | GTT | TCG | TTA | TTT | CGA | GTC | AAT | TCA | CAG | TCA | ACA | ACT | GCA | G | 2749 |

(SEQ ID NO:4)

13. An isolated DNA molecule according to claim 4 wherein said kinase domain has a sequence of a kinase domain from an SRK selected from the group consisting of Brassica oleracea SRK2, Brassica oleracea $SRK_6$, Brassica oleracea SRK13, Brassica oleracea SRK14, Brassica oleracea SRK22, and Brassica campestris SRK8.

14. An isolated DNA fragment from the genus Brassica, which DNA fragment encodes an S receptor kinase and has a nucleotide sequence as follows:

* * * * *

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

Column 13, line 52 to Column 18 (in full), delete in its entirety, and insert therefor --

```
ATG AAA GGG GTA CAG AAC ATT TAC CAC CAT TCT TAC ACC TTC TCG TTC      48
Met Lys Gly Val Gln Asn Ile Tyr His His Ser Tyr Thr Phe Ser Phe
 1           5                  10                      15

TTG CTA GTC TTC CTT GTC TTG ATT CTA TTT CAT CCT GCC CTT TCG ATC      96
Leu Leu Val Phe Leu Val Leu Ile Leu Phe His Pro Ala Leu Ser Ile
            20                  25                  30

TAT GTC AAC ACT TTA TCG TCT TCA GAG TCT CTC ACA ATC TCG AGC AAT     144
Tyr Val Asn Thr Leu Ser Ser Ser Glu Ser Leu Thr Ile Ser Ser Asn
        35                  40                  45

AGA ACA CTT GTA TCT CCC GGT GGA GTC TTC GAG CTT GGT TTC TTC AAA     192
Arg Thr Leu Val Ser Pro Gly Gly Val Phe Glu Leu Gly Phe Phe Lys
    50              55                  60

CCC TTG GGA CGC TCG CGA TGG TAT CTG GGA ATA TGG TAT AAA AAA GCC     240
Pro Leu Gly Arg Ser Arg Trp Tyr Leu Gly Ile Trp Tyr Lys Lys Ala
65              70                  75                      80

CCC TGG AAA ACC TAC GCA TGG GTC GCC AAC AGA GAC AAC CCT CTC TCC     288
Pro Trp Lys Thr Tyr Ala Trp Val Ala Asn Arg Asp Asn Pro Leu Ser
            85                  90                  95

AGT TCT ATT GGA ACC CTC AAA ATC TCT GGC AAC AAT CTT GTC CTG CTA     336
Ser Ser Ile Gly Thr Leu Lys Ile Ser Gly Asn Asn Leu Val Leu Leu
        100                 105                 110

AGT CAG TCT ACT AAC ACT GTT TGG TCG ACA AAT CTT ACT AGA GGA AAT     384
Ser Gln Ser Thr Asn Thr Val Trp Ser Thr Asn Leu Thr Arg Gly Asn
    115                 120                 125

GCG AGA TCT CCG GTG ATA GCA GAG CTT CTT CCC AAC GGT AAT TTT GTA     432
Ala Arg Ser Pro Val Ile Ala Glu Leu Leu Pro Asn Gly Asn Phe Val
130                 135                 140

ATA AGA CAC TCC AAC AAC AAA GAC TCA AGT GGA TTC TTG TGG CAG AGT     480
Ile Arg His Ser Asn Asn Lys Asp Ser Ser Gly Phe Leu Trp Gln Ser
145             150                 155                 160
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

```
TTC GAT TTT CCG ACA GAT ACT TTA CTT CCG GAG ATG AAA CTA GGT TAC        528
Phe Asp Phe Pro Thr Asp Thr Leu Leu Pro Glu Met Lys Leu Gly Tyr
            165             170             175

GAT CTC AAA ACA GGG CGC AAC AGG TTC CTT ACA TCG TGG AAA GGT TCA        576
Asp Leu Lys Thr Gly Arg Asn Arg Phe Leu Thr Ser Trp Lys Gly Ser
        180             185             190

GAT GAT CCG TCA AGC GGG AAT TTC GTG TAC AAA CTC GAC ATT CGA AGG        624
Asp Asp Pro Ser Ser Gly Asn Phe Val Tyr Lys Leu Asp Ile Arg Arg
        195             200             205

GGA TTG CCT GAG TTT ATT CTT ATA AAT CAA TTT TTG AAT CAA CGT GTT        672
Gly Leu Pro Glu Phe Ile Leu Ile Asn Gln Phe Leu Asn Gln Arg Val
        210             215             220

GAA ACG CAA AGG AGC GGT CCT TGG AAT GGA ATG GAG TTT AGT GGC ATA        720
Glu Thr Gln Arg Ser Gly Pro Trp Asn Gly Met Glu Phe Ser Gly Ile
225             230             235             240

CCG GAG GTG CAG GGA TTA AAT TAC ATG GTT TAC AAT TAT ACG GAG AAC        768
Pro Glu Val Gln Gly Leu Asn Tyr Met Val Tyr Asn Tyr Thr Glu Asn
            245             250             255

AGT GAG GAG ATC GCT TAC TCG TTC CAT ATG ACC AAC CAA AGC ATC TAC        816
Ser Glu Glu Ile Ala Tyr Ser Phe His Met Thr Asn Gln Ser Ile Tyr
            260             265             270

TCC AGA TTG ACA GTC AGT GAG TTG ACA CTC GAT CGA TTG ACG TGG ATC        864
Ser Arg Leu Thr Val Ser Glu Leu Thr Leu Asp Arg Leu Thr Trp Ile
        275             280             285

CCG CCA TCA CGG GAT TGG AGC CTC TTC TGG ACT TTA CCA ACG GAC GTG        912
Pro Pro Ser Arg Asp Trp Ser Leu Phe Trp Thr Leu Pro Thr Asp Val
        290             295             300

TGC GAT CCG CTT TAC TTA TGT GGA TCT TAT TCT TAC TGT GAC CTA ATT        960
Cys Asp Pro Leu Tyr Leu Cys Gly Ser Tyr Ser Tyr Cys Asp Leu Ile
305             310             315             320

ACG TCA CCT AAC TGT AAC TGT ATT AGA GGG TTC GTT CCC AAG AAC CCG       1008
Thr Ser Pro Asn Cys Asn Cys Ile Arg Gly Phe Val Pro Lys Asn Pro
            325             330             335

CAG CAG TGG GAC TTG AGA GAC GGA ACA CGG GGG TGT GTG AGG ACG ACG       1056
Gln Gln Trp Asp Leu Arg Asp Gly Thr Arg Gly Cys Val Arg Thr Thr
            340             345             350
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

Page 3 of 15

It is certified that error appears in the above-identified patent and that said Letters Patent is hereby corrected as shown below:

```
CAG ATG AGC TGT AGT GGA GAT GGG TTT TTG CGG CTA AAC AAT ATG AAT    1104
Gln Met Ser Cys Ser Gly Asp Gly Phe Leu Arg Leu Asn Asn Met Asn
        355             360             365

TTG CCG GAT ACT AAG ACG GCA ACT GTG GAT CGG ACA ATG GAT GTG AAA    1152
Leu Pro Asp Thr Lys Thr Ala Thr Val Asp Arg Thr Met Asp Val Lys
        370             375             380

AAA TGT GAA GAG AGG TGT CTT AGC GAT TGT AAC TGT ACT TCG TTT GCT    1200
Lys Cys Glu Glu Arg Cys Leu Ser Asp Cys Asn Cys Thr Ser Phe Ala
385             390             395             400

ATT GCG GAT GTT CGG AAT GGA GGA TTG GGT TGT GTG TTT TGG ACC GGA    1248
Ile Ala Asp Val Arg Asn Gly Gly Leu Gly Cys Val Phe Trp Thr Gly
        405             410             415

GAG CTC GTT GCG ATC AGG AAA TTC GCC GTC GGT GGT CAA GAT CTT TAC    1296
Glu Leu Val Ala Ile Arg Lys Phe Ala Val Gly Gly Gln Asp Leu Tyr
        420             425             430

GTC AGA TTG AAT GCT GCT GAT CTA GAT ATT TCC TCG GGT GAG AAG AGA    1344
Val Arg Leu Asn Ala Ala Asp Leu Asp Ile Ser Ser Gly Glu Lys Arg
        435             440             445

GAC CGA ACT GGA AAA ATC ATA GGT TGG AGT ATT GGA TCC AGC GTT ATG    1392
Asp Arg Thr Gly Lys Ile Ile Gly Trp Ser Ile Gly Ser Ser Val Met
        450             455             460

CTT ATT CTG AGT GTT ATC TTG TTC TGC TTT TGG AGG AGG AGA CAA AAG    1440
Leu Ile Leu Ser Val Ile Leu Phe Cys Phe Trp Arg Arg Arg Gln Lys
465             470             475             480

CAA GCA AAA GCA GAT GCA ACA CCT ATT GTG GGA AAT CAA GTT CTA ATG    1488
Gln Ala Lys Ala Asp Ala Thr Pro Ile Val Gly Asn Gln Val Leu Met
        485             490             495

AAC GAG GTG GTG TTA CCA AGA AAG AAG AGA AAT TTT TCT GGA GAG GAC    1536
Asn Glu Val Val Leu Pro Arg Lys Lys Arg Asn Phe Ser Gly Glu Asp
        500             505             510

GAT GTA GAA AAT TTG GAA CTT CCA TTG ATG GAG TTT GAA GCT GTT GTC    1584
Asp Val Glu Asn Leu Glu Leu Pro Leu Met Glu Phe Glu Ala Val Val
        515             520             525

ACA GCC ACC GAA CAT TTC TCT GAT TTT AAC AAG GTC GGA AAA GGT GGT    1632
Thr Ala Thr Glu His Phe Ser Asp Phe Asn Lys Val Gly Lys Gly Gly
        530             535             540
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

Page 4 of 15

It is certified that error appears in the above-identified patent and that said Letters Patent is hereby corrected as shown below:

```
TTT GGT GTT GTT TAC AAG GGA AGG TTA GTT GAC GGG CAA GAA ATT GCA      1680
Phe Gly Val Val Tyr Lys Gly Arg Leu Val Asp Gly Gln Glu Ile Ala
545                 550                 555                 560

GTG AAG AGA CTA TCG GAA ATG TCA GCT CAA GGT ACC GAT GAG TTC ATG      1728
Val Lys Arg Leu Ser Glu Met Ser Ala Gln Gly Thr Asp Glu Phe Met
                565                 570                 575

AAC GAA GTT AGG CTA ATG CAA AGC TTC AGC CAC AAT AAT CTT GTC CGA      1776
Asn Glu Val Arg Leu Met Gln Ser Phe Ser His Asn Asn Leu Val Arg
            580                 585                 590

CTT CTT GGC TGT TGT GTT TAT GAG GGC GAG AAG ATC TTA ATT TAC GAG      1824
Leu Leu Gly Cys Cys Val Tyr Glu Gly Glu Lys Ile Leu Ile Tyr Glu
        595                 600                 605

TAC TTG GAG AAT CTA AGC CTC GAT TCT CAT CTC TTT GAT GAA ACC AGA      1872
Tyr Leu Glu Asn Leu Ser Leu Asp Ser His Leu Phe Asp Glu Thr Arg
    610                 615                 620

AGC TGT ATG TTA AAT TGG CAA ATG AGA TTT GAT ATT ATC AAT GGT ATT      1920
Ser Cys Met Leu Asn Trp Gln Met Arg Phe Asp Ile Ile Asn Gly Ile
625                 630                 635                 640

GCC CGA GGG CTT CTC TAT CTT CAC CAA GAT TCA CGG TTT AGA ATC ATC      1968
Ala Arg Gly Leu Leu Tyr Leu His Gln Asp Ser Arg Phe Arg Ile Ile
                645                 650                 655

CAC AGG GAT TTG AAA GCA AGC AAT GTC TTG CTT GAT AAA GAT ATG ACT      2016
His Arg Asp Leu Lys Ala Ser Asn Val Leu Leu Asp Lys Asp Met Thr
            660                 665                 670

CCA AAA ATT TCA GAC TTT GGA ATG GCT AGG ATC TTT GGA CGG GAT GAG      2064
Pro Lys Ile Ser Asp Phe Gly Met Ala Arg Ile Phe Gly Arg Asp Glu
        675                 680                 685

ACG GAA GCT GAC ACG AGG AAG GTG GTC GGA ACT TAT GGC TAC ATG TCT      2112
Thr Glu Ala Asp Thr Arg Lys Val Val Gly Thr Tyr Gly Tyr Met Ser
    690                 695                 700

CCA GAA TAT GCG ATG AAC GGG ACA TTC TCA ATG AAG TCA GAT GTG TTC      2160
Pro Glu Tyr Ala Met Asn Gly Thr Phe Ser Met Lys Ser Asp Val Phe
705                 710                 715                 720

AGT TTT GGG GTC TTG CTT CTT GAA ATT ATA AGT GGC AAG AGG AAC AAA      2208
Ser Phe Gly Val Leu Leu Leu Glu Ile Ile Ser Gly Lys Arg Asn Lys
                725                 730                 735
```

UNITED STATES PATENT AND TRADEMARK OFFICE
CERTIFICATE OF CORRECTION

PATENT NO. : 5,484,905   Page 5 of 15
DATED : January 16, 1996
INVENTOR(S) : June B. Nasrallah, Mikhasil E. Nasrallah, Joshua Stein It is certified that error appears in the above-identified patent and that said Letters Patent is hereby corrected as shown below:

```
CCA GAA TAT GCG ATG AAC GGG ACA TTC TCA ATG AAG TCA GAT GTG TTC         2160
Pro Glu Tyr Ala Met Asn Gly Thr Phe Ser Met Lys Ser Asp Val Phe
705                 710                 715                 720

AGT TTT GGG GTC TTG CTT CTT GAA ATT ATA AGT GGC AAG AGG AAC AAA         2208
Ser Phe Gly Val Leu Leu Leu Glu Ile Ile Ser Gly Lys Arg Asn Lys
                725                 730                 735

GGC TTA TGC GAC TCG GAT AGT AGC CTT AAT CTT CTC GGA TGT GTA TGG         2256
Gly Leu Cys Asp Ser Asp Ser Ser Leu Asn Leu Leu Gly Cys Val Trp
            740                 745                 750

AGG AAT TGG AAA GAA GGT CAA GGT CTA GAG ATA GTA GAC AAG GTC ATC         2304
Arg Asn Trp Lys Glu Gly Gln Gly Leu Glu Ile Val Asp Lys Val Ile
        755                 760                 765

ATA GAT TCT TCA TCA CCA ACG TTC AGG CCA CGT GAA ATC TTA AGA TGC         2352
Ile Asp Ser Ser Ser Pro Thr Phe Arg Pro Arg Glu Ile Leu Arg Cys
    770                 775                 780

TTA CAA ATT GGC CTC TTG TGT GTT CAA GAA CGT GTG GAG GAT AGA CCA         2400
Leu Gln Ile Gly Leu Leu Cys Val Gln Glu Arg Val Glu Asp Arg Pro
785                 790                 795                 800

ATG ATG TCG TCA GTA GTT TTG ATG CTC GGA AGT GAA GCT GCA TTG ATT         2448
Met Met Ser Ser Val Val Leu Met Leu Gly Ser Glu Ala Ala Leu Ile
                805                 810                 815

CCT CAA CCT AAA CAG CCA GGA TAT TGC GTC AGC GGA AGT TCT CTT GAA         2496
Pro Gln Pro Lys Gln Pro Gly Tyr Cys Val Ser Gly Ser Ser Leu Glu
            820                 825                 830

ACT TAT TCT AGG CGT GAC GAT GAA AAT TGC ACA GTG AAC CAA ATC ACC         2544
Thr Tyr Ser Arg Arg Asp Asp Glu Asn Cys Thr Val Asn Gln Ile Thr
        835                 840                 845

ATG TCG ATC ATT GAC GCT CGG TAATATGATA GTCTTTGATA ATATTCTCAC            2595
Met Ser Ile Ile Asp Ala Arg
850                 855

TATTAAAGTT TTACTAAATG GAAAAAAAGA GTTTTACAAG TTGAGTGACA AAGCGTGCCA       2655

AACTCTTCAG TCTATCGAAA TTTTCATTCA TCCTCTGTAT ATTCTCTCGA ATTGGTTTCG       2715

TTATTTCGAG TCAATTCACA GTCAACAACT GCAG                                   2749

(SEQ ID NO:3)                                                           --.
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

Page 6 of 15

It is certified that error appears in the above-identified patent and that said Letters Patent is hereby corrected as shown below:

Column 53 to Column 58 (SEQ ID NO:3 in full), delete in its entirety, and insert therefor --

```
ATG AAA GGG GTA CAG AAC ATT TAC CAC CAT TCT TAC ACC TTC TCG TTC      48
Met Lys Gly Val Gln Asn Ile Tyr His His Ser Tyr Thr Phe Ser Phe
 1           5                  10                  15

TTG CTA GTC TTC CTT GTC TTG ATT CTA TTT CAT CCT GCC CTT TCG ATC      96
Leu Leu Val Phe Leu Val Leu Ile Leu Phe His Pro Ala Leu Ser Ile
             20                  25                  30

TAT GTC AAC ACT TTA TCG TCT TCA GAG TCT CTC ACA ATC TCG AGC AAT     144
Tyr Val Asn Thr Leu Ser Ser Ser Glu Ser Leu Thr Ile Ser Ser Asn
         35                  40                  45

AGA ACA CTT GTA TCT CCC GGT GGA GTC TTC GAG CTT GGT TTC TTC AAA     192
Arg Thr Leu Val Ser Pro Gly Gly Val Phe Glu Leu Gly Phe Phe Lys
     50                  55                  60

CCC TTG GGA CGC TCG CGA TGG TAT CTG GGA ATA TGG TAT AAA AAA GCC     240
Pro Leu Gly Arg Ser Arg Trp Tyr Leu Gly Ile Trp Tyr Lys Lys Ala
 65                  70                  75                  80

CCC TGG AAA ACC TAC GCA TGG GTC GCC AAC AGA GAC AAC CCT CTC TCC     288
Pro Trp Lys Thr Tyr Ala Trp Val Ala Asn Arg Asp Asn Pro Leu Ser
             85                  90                  95

AGT TCT ATT GGA ACC CTC AAA ATC TCT GGC AAC AAT CTT GTC CTG CTA     336
Ser Ser Ile Gly Thr Leu Lys Ile Ser Gly Asn Asn Leu Val Leu Leu
         100                 105                 110

AGT CAG TCT ACT AAC ACT GTT TGG TCG ACA AAT CTT ACT AGA GGA AAT     384
Ser Gln Ser Thr Asn Thr Val Trp Ser Thr Asn Leu Thr Arg Gly Asn
     115                 120                 125

GCG AGA TCT CCG GTG ATA GCA GAG CTT CTT CCC AAC GGT AAT TTT GTA     432
Ala Arg Ser Pro Val Ile Ala Glu Leu Leu Pro Asn Gly Asn Phe Val
 130                 135                 140

ATA AGA CAC TCC AAC AAC AAA GAC TCA AGT GGA TTC TTG TGG CAG AGT     480
Ile Arg His Ser Asn Asn Lys Asp Ser Ser Gly Phe Leu Trp Gln Ser
 145                 150                 155                 160
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

```
TTC GAT TTT CCG ACA GAT ACT TTA CTT CCG GAG ATG AAA CTA GGT TAC      528
Phe Asp Phe Pro Thr Asp Thr Leu Leu Pro Glu Met Lys Leu Gly Tyr
            165             170             175

GAT CTC AAA ACA GGG CGC AAC AGG TTC CTT ACA TCG TGG AAA GGT TCA      576
Asp Leu Lys Thr Gly Arg Asn Arg Phe Leu Thr Ser Trp Lys Gly Ser
            180             185             190

GAT GAT CCG TCA AGC GGG AAT TTC GTG TAC AAA CTC GAC ATT CGA AGG      624
Asp Asp Pro Ser Ser Gly Asn Phe Val Tyr Lys Leu Asp Ile Arg Arg
            195             200             205

GGA TTG CCT GAG TTT ATT CTT ATA AAT CAA TTT TTG AAT CAA CGT GTT      672
Gly Leu Pro Glu Phe Ile Leu Ile Asn Gln Phe Leu Asn Gln Arg Val
    210             215             220

GAA ACG CAA AGG AGC GGT CCT TGG AAT GGA ATG GAG TTT AGT GGC ATA      720
Glu Thr Gln Arg Ser Gly Pro Trp Asn Gly Met Glu Phe Ser Gly Ile
225             230             235             240

CCG GAG GTG CAG GGA TTA AAT TAC ATG GTT TAC AAT TAT ACG GAG AAC      768
Pro Glu Val Gln Gly Leu Asn Tyr Met Val Tyr Asn Tyr Thr Glu Asn
            245             250             255

AGT GAG GAG ATC GCT TAC TCG TTC CAT ATG ACC AAC CAA AGC ATC TAC      816
Ser Glu Glu Ile Ala Tyr Ser Phe His Met Thr Asn Gln Ser Ile Tyr
            260             265             270

TCC AGA TTG ACA GTC AGT GAG TTG ACA CTC GAT CGA TTG ACG TGG ATC      864
Ser Arg Leu Thr Val Ser Glu Leu Thr Leu Asp Arg Leu Thr Trp Ile
            275             280             285

CCG CCA TCA CGG GAT TGG AGC CTC TTC TGG ACT TTA CCA ACG GAC GTG      912
Pro Pro Ser Arg Asp Trp Ser Leu Phe Trp Thr Leu Pro Thr Asp Val
            290             295             300

TGC GAT CCG CTT TAC TTA TGT GGA TCT TAT TCT TAC TGT GAC CTA ATT      960
Cys Asp Pro Leu Tyr Leu Cys Gly Ser Tyr Ser Tyr Cys Asp Leu Ile
305             310             315             320

ACG TCA CCT AAC TGT AAC TGT ATT AGA GGG TTC GTT CCC AAG AAC CCG     1008
Thr Ser Pro Asn Cys Asn Cys Ile Arg Gly Phe Val Pro Lys Asn Pro
            325             330             335

CAG CAG TGG GAC TTG AGA GAC GGA ACA CGG GGG TGT GTG AGG ACG ACG     1056
Gln Gln Trp Asp Leu Arg Asp Gly Thr Arg Gly Cys Val Arg Thr Thr
            340             345             350
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

```
CAG ATG AGC TGT AGT GGA GAT GGG TTT TTG CGG CTA AAC AAT ATG AAT      1104
Gln Met Ser Cys Ser Gly Asp Gly Phe Leu Arg Leu Asn Asn Met Asn
    355                 360                 365

TTG CCG GAT ACT AAG ACG GCA ACT GTG GAT CGG ACA ATG GAT GTG AAA      1152
Leu Pro Asp Thr Lys Thr Ala Thr Val Asp Arg Thr Met Asp Val Lys
    370                 375                 380

AAA TGT GAA GAG AGG TGT CTT AGC GAT TGT AAC TGT ACT TCG TTT GCT      1200
Lys Cys Glu Glu Arg Cys Leu Ser Asp Cys Asn Cys Thr Ser Phe Ala
385                 390                 395                 400

ATT GCG GAT GTT CGG AAT GGA GGA TTG GGT TGT GTG TTT TGG ACC GGA      1248
Ile Ala Asp Val Arg Asn Gly Gly Leu Gly Cys Val Phe Trp Thr Gly
                405                 410                 415

GAG CTC GTT GCG ATC AGG AAA TTC GCC GTC GGT GGT CAA GAT CTT TAC      1296
Glu Leu Val Ala Ile Arg Lys Phe Ala Val Gly Gly Gln Asp Leu Tyr
        420                 425                 430

GTC AGA TTG AAT GCT GCT GAT CTA GAT ATT TCC TCG GGT GAG AAG AGA      1344
Val Arg Leu Asn Ala Ala Asp Leu Asp Ile Ser Ser Gly Glu Lys Arg
        435                 440                 445

GAC CGA ACT GGA AAA ATC ATA GGT TGG AGT ATT GGA TCC AGC GTT ATG      1392
Asp Arg Thr Gly Lys Ile Ile Gly Trp Ser Ile Gly Ser Ser Val Met
    450                 455                 460

CTT ATT CTG AGT GTT ATC TTG TTC TGC TTT TGG AGG AGG AGA CAA AAG      1440
Leu Ile Leu Ser Val Ile Leu Phe Cys Phe Trp Arg Arg Arg Gln Lys
465                 470                 475                 480

CAA GCA AAA GCA GAT GCA ACA CCT ATT GTG GGA AAT CAA GTT CTA ATG      1488
Gln Ala Lys Ala Asp Ala Thr Pro Ile Val Gly Asn Gln Val Leu Met
            485                 490                 495

AAC GAG GTG GTG TTA CCA AGA AAG AAG AGA AAT TTT TCT GGA GAG GAC      1536
Asn Glu Val Val Leu Pro Arg Lys Lys Arg Asn Phe Ser Gly Glu Asp
            500                 505                 510

GAT GTA GAA AAT TTG GAA CTT CCA TTG ATG GAG TTT GAA GCT GTT GTC      1584
Asp Val Glu Asn Leu Glu Leu Pro Leu Met Glu Phe Glu Ala Val Val
        515                 520                 525

ACA GCC ACC GAA CAT TTC TCT GAT TTT AAC AAG GTC GGA AAA GGT GGT      1632
Thr Ala Thr Glu His Phe Ser Asp Phe Asn Lys Val Gly Lys Gly Gly
    530                 535                 540
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

```
TTT GGT GTT GTT TAC AAG GGA AGG TTA GTT GAC GGG CAA GAA ATT GCA      1680
Phe Gly Val Val Tyr Lys Gly Arg Leu Val Asp Gly Gln Glu Ile Ala
545                 550                 555                 560

GTG AAG AGA CTA TCG GAA ATG TCA GCT CAA GGT ACC GAT GAG TTC ATG      1728
Val Lys Arg Leu Ser Glu Met Ser Ala Gln Gly Thr Asp Glu Phe Met
                565                 570                 575

AAC GAA GTT AGG CTA ATG CAA AGC TTC AGC CAC AAT AAT CTT GTC CGA      1776
Asn Glu Val Arg Leu Met Gln Ser Phe Ser His Asn Asn Leu Val Arg
            580                 585                 590

CTT CTT GGC TGT TGT GTT TAT GAG GGC GAG AAG ATC TTA ATT TAC GAG      1824
Leu Leu Gly Cys Cys Val Tyr Glu Gly Glu Lys Ile Leu Ile Tyr Glu
        595                 600                 605

TAC TTG GAG AAT CTA AGC CTC GAT TCT CAT CTC TTT GAT GAA ACC AGA      1872
Tyr Leu Glu Asn Leu Ser Leu Asp Ser His Leu Phe Asp Glu Thr Arg
    610                 615                 620

AGC TGT ATG TTA AAT TGG CAA ATG AGA TTT GAT ATT ATC AAT GGT ATT      1920
Ser Cys Met Leu Asn Trp Gln Met Arg Phe Asp Ile Ile Asn Gly Ile
625                 630                 635                 640

GCC CGA GGG CTT CTC TAT CTT CAC CAA GAT TCA CGG TTT AGA ATC ATC      1968
Ala Arg Gly Leu Leu Tyr Leu His Gln Asp Ser Arg Phe Arg Ile Ile
                645                 650                 655

CAC AGG GAT TTG AAA GCA AGC AAT GTC TTG CTT GAT AAA GAT ATG ACT      2016
His Arg Asp Leu Lys Ala Ser Asn Val Leu Leu Asp Lys Asp Met Thr
            660                 665                 670

CCA AAA ATT TCA GAC TTT GGA ATG GCT AGG ATC TTT GGA CGG GAT GAG      2064
Pro Lys Ile Ser Asp Phe Gly Met Ala Arg Ile Phe Gly Arg Asp Glu
        675                 680                 685

ACG GAA GCT GAC ACG AGG AAG GTG GTC GGA ACT TAT GGC TAC ATG TCT      2112
Thr Glu Ala Asp Thr Arg Lys Val Val Gly Thr Tyr Gly Tyr Met Ser
    690                 695                 700

CCA GAA TAT GCG ATG AAC GGG ACA TTC TCA ATG AAG TCA GAT GTG TTC      2160
Pro Glu Tyr Ala Met Asn Gly Thr Phe Ser Met Lys Ser Asp Val Phe
705                 710                 715                 720

AGT TTT GGG GTC TTG CTT CTT GAA ATT ATA AGT GGC AAG AGG AAC AAA      2208
Ser Phe Gly Val Leu Leu Leu Glu Ile Ile Ser Gly Lys Arg Asn Lys
                725                 730                 735

GGC TTA TGC GAC TCG GAT AGT AGC CTT AAT CTT CTC GGA TGT GTA TGG      2256
Gly Leu Cys Asp Ser Asp Ser Ser Leu Asn Leu Leu Gly Cys Val Trp
            740                 745                 750
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

```
AGG AAT TGG AAA GAA GGT CAA GGT CTA GAG ATA GTA GAC AAG GTC ATC        2304
Arg Asn Trp Lys Glu Gly Gln Gly Leu Glu Ile Val Asp Lys Val Ile
        755             760                 765

ATA GAT TCT TCA TCA CCA ACG TTC AGG CCA CGT GAA ATC TTA AGA TGC        2352
Ile Asp Ser Ser Ser Pro Thr Phe Arg Pro Arg Glu Ile Leu Arg Cys
        770             775                 780

TTA CAA ATT GGC CTC TTG TGT GTT CAA GAA CGT GTG GAG GAT AGA CCA        2400
Leu Gln Ile Gly Leu Leu Cys Val Gln Glu Arg Val Glu Asp Arg Pro
785             790                 795                 800

ATG ATG TCG TCA GTA GTT TTG ATG CTC GGA AGT GAA GCT GCA TTG ATT        2448
Met Met Ser Ser Val Val Leu Met Leu Gly Ser Glu Ala Ala Leu Ile
                805                 810                 815

CCT CAA CCT AAA CAG CCA GGA TAT TGC GTC AGC GGA AGT TCT CTT GAA        2496
Pro Gln Pro Lys Gln Pro Gly Tyr Cys Val Ser Gly Ser Ser Leu Glu
                820                 825                 830

ACT TAT TCT AGG CGT GAC GAT GAA AAT TGC ACA GTG AAC CAA ATC ACC        2544
Thr Tyr Ser Arg Arg Asp Asp Glu Asn Cys Thr Val Asn Gln Ile Thr
            835                 840                 845

ATG TCG ATC ATT GAC GCT CGG TAATATGATA GTCTTTGATA ATATTCTCAC           2595
Met Ser Ile Ile Asp Ala Arg
850                 855

TATTAAAGTT TTACTAAATG GAAAAAAAGA GTTTTACAAG TTGAGTGACA AAGCGTGCCA      2655

AACTCTTCAG TCTATCGAAA TTTTCATTCA TCCTCTGTAT ATTCTCTCGA ATTGGTTTCG      2715

TTATTTCGAG TCAATTCACA GTCAACAACT GCAG                                  2749 --.
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

Page 11 of 15

It is certified that error appears in the above-identified patent and that said Letters Patent is hereby corrected as shown below:

In Claim 2, line 4 (Column 69-70) to Column 74 (SEQ ID NO:3 in full), delete in its entirety, and insert therefor --

```
ATG AAA GGG GTA CAG AAC ATT TAC CAC CAT TCT TAC ACC TTC TCG TTC        48
Met Lys Gly Val Gln Asn Ile Tyr His His Ser Tyr Thr Phe Ser Phe
 1               5                  10                  15

TTG CTA GTC TTC CTT GTC TTG ATT CTA TTT CAT CCT GCC CTT TCG ATC        96
Leu Leu Val Phe Leu Val Leu Ile Leu Phe His Pro Ala Leu Ser Ile
                20                  25                  30

TAT GTC AAC ACT TTA TCG TCT TCA GAG TCT CTC ACA ATC TCG AGC AAT       144
Tyr Val Asn Thr Leu Ser Ser Ser Glu Ser Leu Thr Ile Ser Ser Asn
            35                  40                  45

AGA ACA CTT GTA TCT CCC GGT GGA GTC TTC GAG CTT GGT TTC TTC AAA       192
Arg Thr Leu Val Ser Pro Gly Gly Val Phe Glu Leu Gly Phe Phe Lys
        50                  55                  60

CCC TTG GGA CGC TCG CGA TGG TAT CTG GGA ATA TGG TAT AAA AAA GCC       240
Pro Leu Gly Arg Ser Arg Trp Tyr Leu Gly Ile Trp Tyr Lys Lys Ala
    65                  70                  75                  80

CCC TGG AAA ACC TAC GCA TGG GTC GCC AAC AGA GAC AAC CCT CTC TCC       288
Pro Trp Lys Thr Tyr Ala Trp Val Ala Asn Arg Asp Asn Pro Leu Ser
                85                  90                  95

AGT TCT ATT GGA ACC CTC AAA ATC TCT GGC AAC AAT CTT GTC CTG CTA       336
Ser Ser Ile Gly Thr Leu Lys Ile Ser Gly Asn Asn Leu Val Leu Leu
            100                 105                 110

AGT CAG TCT ACT AAC ACT GTT TGG TCG ACA AAT CTT ACT AGA GGA AAT       384
Ser Gln Ser Thr Asn Thr Val Trp Ser Thr Asn Leu Thr Arg Gly Asn
        115                 120                 125

GCG AGA TCT CCG GTG ATA GCA GAG CTT CTT CCC AAC GGT AAT TTT GTA       432
Ala Arg Ser Pro Val Ile Ala Glu Leu Leu Pro Asn Gly Asn Phe Val
    130                 135                 140
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

Page 12 of 15

It is certified that error appears in the above-identified patent and that said Letters Patent is hereby corrected as shown below:

```
ATA AGA CAC TCC AAC AAC AAA GAC TCA AGT GGA TTC TTG TGG CAG AGT          480
Ile Arg His Ser Asn Asn Lys Asp Ser Ser Gly Phe Leu Trp Gln Ser
145                     150                 155                 160

TTC GAT TTT CCG ACA GAT ACT TTA CTT CCG GAG ATG AAA CTA GGT TAC          528
Phe Asp Phe Pro Thr Asp Thr Leu Leu Pro Glu Met Lys Leu Gly Tyr
                165                 170                 175

GAT CTC AAA ACA GGG CGC AAC AGG TTC CTT ACA TCG TGG AAA GGT TCA          576
Asp Leu Lys Thr Gly Arg Asn Arg Phe Leu Thr Ser Trp Lys Gly Ser
            180                 185                 190

GAT GAT CCG TCA AGC GGG AAT TTC GTG TAC AAA CTC GAC ATT CGA AGG          624
Asp Asp Pro Ser Ser Gly Asn Phe Val Tyr Lys Leu Asp Ile Arg Arg
        195                 200                 205

GGA TTG CCT GAG TTT ATT CTT ATA AAT CAA TTT TTG AAT CAA CGT GTT          672
Gly Leu Pro Glu Phe Ile Leu Ile Asn Gln Phe Leu Asn Gln Arg Val
210                 215                 220

GAA ACG CAA AGG AGC GGT CCT TGG AAT GGA ATG GAG TTT AGT GGC ATA          720
Glu Thr Gln Arg Ser Gly Pro Trp Asn Gly Met Glu Phe Ser Gly Ile
225                 230                 235                 240

CCG GAG GTG CAG GGA TTA AAT TAC ATG GTT TAC AAT TAT ACG GAG AAC          768
Pro Glu Val Gln Gly Leu Asn Tyr Met Val Tyr Asn Tyr Thr Glu Asn
                245                 250                 255

AGT GAG GAG ATC GCT TAC TCG TTC CAT ATG ACC AAC CAA AGC ATC TAC          816
Ser Glu Glu Ile Ala Tyr Ser Phe His Met Thr Asn Gln Ser Ile Tyr
            260                 265                 270

TCC AGA TTG ACA GTC AGT GAG TTG ACA CTC GAT CGA TTG ACG TGG ATC          864
Ser Arg Leu Thr Val Ser Glu Leu Thr Leu Asp Arg Leu Thr Trp Ile
        275                 280                 285

CCG CCA TCA CGG GAT TGG AGC CTC TTC TGG ACT TTA CCA ACG GAC GTG          912
Pro Pro Ser Arg Asp Trp Ser Leu Phe Trp Thr Leu Pro Thr Asp Val
290                 295                 300

TGC GAT CCG CTT TAC TTA TGT GGA TCT TAT TCT TAC TGT GAC CTA ATT          960
Cys Asp Pro Leu Tyr Leu Cys Gly Ser Tyr Ser Tyr Cys Asp Leu Ile
305                 310                 315                 320

ACG TCA CCT AAC TGT AAC TGT ATT AGA GGG TTC GTT CCC AAG AAC CCG         1008
Thr Ser Pro Asn Cys Asn Cys Ile Arg Gly Phe Val Pro Lys Asn Pro
                325                 330                 335
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

```
CAG CAG TGG GAC TTG AGA GAC GGA ACA CGG GGG TGT GTG AGG ACG ACG     1056
Gln Gln Trp Asp Leu Arg Asp Gly Thr Arg Gly Cys Val Arg Thr Thr
            340             345             350

CAG ATG AGC TGT AGT GGA GAT GGG TTT TTG CGG CTA AAC AAT ATG AAT     1104
Gln Met Ser Cys Ser Gly Asp Gly Phe Leu Arg Leu Asn Asn Met Asn
        355             360             365

TTG CCG GAT ACT AAG ACG GCA ACT GTG GAT CGG ACA ATG GAT GTG AAA     1152
Leu Pro Asp Thr Lys Thr Ala Thr Val Asp Arg Thr Met Asp Val Lys
        370             375             380

AAA TGT GAA GAG AGG TGT CTT AGC GAT TGT AAC TGT ACT TCG TTT GCT     1200
Lys Cys Glu Glu Arg Cys Leu Ser Asp Cys Asn Cys Thr Ser Phe Ala
385             390             395             400

ATT GCG GAT GTT CGG AAT GGA GGA TTG GGT TGT GTG TTT TGG ACC GGA     1248
Ile Ala Asp Val Arg Asn Gly Gly Leu Gly Cys Val Phe Trp Thr Gly
                405             410             415

GAG CTC GTT GCG ATC AGG AAA TTC GCC GTC GGT GGT CAA GAT CTT TAC     1296
Glu Leu Val Ala Ile Arg Lys Phe Ala Val Gly Gly Gln Asp Leu Tyr
                420             425             430

GTC AGA TTG AAT GCT GCT GAT CTA GAT ATT TCC TCG GGT GAG AAG AGA     1344
Val Arg Leu Asn Ala Ala Asp Leu Asp Ile Ser Ser Gly Glu Lys Arg
            435             440             445

GAC CGA ACT GGA AAA ATC ATA GGT TGG AGT ATT GGA TCC AGC GTT ATG     1392
Asp Arg Thr Gly Lys Ile Ile Gly Trp Ser Ile Gly Ser Ser Val Met
        450             455             460

CTT ATT CTG AGT GTT ATC TTG TTC TGC TTT TGG AGG AGG AGA CAA AAG     1440
Leu Ile Leu Ser Val Ile Leu Phe Cys Phe Trp Arg Arg Arg Gln Lys
465             470             475             480

CAA GCA AAA GCA GAT GCA ACA CCT ATT GTG GGA AAT CAA GTT CTA ATG     1488
Gln Ala Lys Ala Asp Ala Thr Pro Ile Val Gly Asn Gln Val Leu Met
                485             490             495

AAC GAG GTG GTG TTA CCA AGA AAG AAG AGA AAT TTT TCT GGA GAG GAC     1536
Asn Glu Val Val Leu Pro Arg Lys Lys Arg Asn Phe Ser Gly Glu Asp
            500             505             510
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

Page 14 of 15

It is certified that error appears in the above-identified patent and that said Letters Patent is hereby corrected as shown below:

```
GAT GTA GAA AAT TTG GAA CTT CCA TTG ATG GAG TTT GAA GCT GTT GTC       1584
Asp Val Glu Asn Leu Glu Leu Pro Leu Met Glu Phe Glu Ala Val Val
        515             520             525

ACA GCC ACC GAA CAT TTC TCT GAT TTT AAC AAG GTC GGA AAA GGT GGT       1632
Thr Ala Thr Glu His Phe Ser Asp Phe Asn Lys Val Gly Lys Gly Gly
        530             535             540

TTT GGT GTT GTT TAC AAG GGA AGG TTA GTT GAC GGG CAA GAA ATT GCA       1680
Phe Gly Val Val Tyr Lys Gly Arg Leu Val Asp Gly Gln Glu Ile Ala
545             550             555             560

GTG AAG AGA CTA TCG GAA ATG TCA GCT CAA GGT ACC GAT GAG TTC ATG       1728
Val Lys Arg Leu Ser Glu Met Ser Ala Gln Gly Thr Asp Glu Phe Met
            565             570             575

AAC GAA GTT AGG CTA ATG CAA AGC TTC AGC CAC AAT AAT CTT GTC CGA       1776
Asn Glu Val Arg Leu Met Gln Ser Phe Ser His Asn Asn Leu Val Arg
            580             585             590

CTT CTT GGC TGT TGT GTT TAT GAG GGC GAG AAG ATC TTA ATT TAC GAG       1824
Leu Leu Gly Cys Cys Val Tyr Glu Gly Glu Lys Ile Leu Ile Tyr Glu
        595             600             605

TAC TTG GAG AAT CTA AGC CTC GAT TCT CAT CTC TTT GAT GAA ACC AGA       1872
Tyr Leu Glu Asn Leu Ser Leu Asp Ser His Leu Phe Asp Glu Thr Arg
610             615             620

AGC TGT ATG TTA AAT TGG CAA ATG AGA TTT GAT ATT ATC AAT GGT ATT       1920
Ser Cys Met Leu Asn Trp Gln Met Arg Phe Asp Ile Ile Asn Gly Ile
625             630             635             640

GCC CGA GGG CTT CTC TAT CTT CAC CAA GAT TCA CGG TTT AGA ATC ATC       1968
Ala Arg Gly Leu Leu Tyr Leu His Gln Asp Ser Arg Phe Arg Ile Ile
            645             650             655

CAC AGG GAT TTG AAA GCA AGC AAT GTC TTG CTT GAT AAA GAT ATG ACT       2016
His Arg Asp Leu Lys Ala Ser Asn Val Leu Leu Asp Lys Asp Met Thr
            660             665             670

CCA AAA ATT TCA GAC TTT GGA ATG GCT AGG ATC TTT GGA CGG GAT GAG       2064
Pro Lys Ile Ser Asp Phe Gly Met Ala Arg Ile Phe Gly Arg Asp Glu
        675             680             685

ACG GAA GCT GAC ACG AGG AAG GTG GTC GGA ACT TAT GGC TAC ATG TCT       2112
Thr Glu Ala Asp Thr Arg Lys Val Val Gly Thr Tyr Gly Tyr Met Ser
690             695             700
```

UNITED STATES PATENT AND TRADEMARK OFFICE
CERTIFICATE OF CORRECTION

PATENT NO. : 5,484,905

DATED : January 16, 1996

INVENTOR(S) : June B. Nasrallah, Mikhasil E. Nasrallah, Joshua Stein

It is certified that error appears in the above-identified patent and that said Letters Patent is hereby corrected as shown below:

```
GCC TTA TGC GAC TCG GAT AGT AGC CTT AAT CTT CTC GGA TGT GTA TGG    2256
Gly Leu Cys Asp Ser Asp Ser Ser Leu Asn Leu Leu Gly Cys Val Trp
             740             745                 750

AGG AAT TGG AAA GAA GGT CAA GGT CTA GAG ATA GTA GAC AAG GTC ATC    2304
Arg Asn Trp Lys Glu Gly Gln Gly Leu Glu Ile Val Asp Lys Val Ile
             755             760                 765

ATA GAT TCT TCA TCA CCA ACG TTC AGG CCA CGT GAA ATC TTA AGA TGC    2352
Ile Asp Ser Ser Ser Pro Thr Phe Arg Pro Arg Glu Ile Leu Arg Cys
             770             775                 780

TTA CAA ATT GGC CTC TTG TGT GTT CAA GAA CGT GTG GAG GAT AGA CCA    2400
Leu Gln Ile Gly Leu Leu Cys Val Gln Glu Arg Val Glu Asp Arg Pro
785              790             795                 800

ATG ATG TCG TCA GTA GTT TTG ATG CTC GGA AGT GAA GCT GCA TTG ATT    2448
Met Met Ser Ser Val Val Leu Met Leu Gly Ser Glu Ala Ala Leu Ile
             805             810                 815

CCT CAA CCT AAA CAG CCA GGA TAT TGC GTC AGC GGA AGT TCT CTT GAA    2496
Pro Gln Pro Lys Gln Pro Gly Tyr Cys Val Ser Gly Ser Ser Leu Glu
             820             825                 830

ACT TAT TCT AGG CGT GAC GAT GAA AAT TGC ACA GTG AAC CAA ATC ACC    2544
Thr Tyr Ser Arg Arg Asp Asp Glu Asn Cys Thr Val Asn Gln Ile Thr
             835             840                 845

ATG TCG ATC ATT GAC GCT CGG TAATATGATA GTCTTTGATA ATATTCTCAC       2595
Met Ser Ile Ile Asp Ala Arg
850              855

TATTAAAGTT TTACTAAATG GAAAAAAAGA GTTTTACAAG TTGAGTGACA AAGCGTGCCA  2655

AACTCTTCAG TCTATCGAAA TTTTCATTCA TCCTCTGTAT ATTCTCTCGA ATTGGTTTCG  2715

TTATTTCGAG TCAATTCACA GTCAACAACT GCAG                             2749 --.
```

Signed and Sealed this

Twenty-seventh Day of January, 1998

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,484,905

Page 1 of 17

DATED : January 16, 1996

INVENTOR(S) : June B. Nasrallah, Mikhail E. Nasrallah, Joshua Stein

It is certified that error appears in the above-identified patent and that said Letters Patent is hereby corrected as shown below:

Delete the title page, and replaced with the attached title page.

This certificate supersedes certificate of correction issued January 27, 1998.

United States Patent [19]

Nasrallah et al.

[11] Patent Number: 5,484,905
[45] Date of Patent: Jan. 16, 1996

[54] RECEPTOR PROTEIN KINASE GENE ENCODED AT THE SELF-INCOMPATIBILITY LOCUS

[75] Inventors: June B. Nasrallah; Mikhail E. Nasrallah, both of Ithaca; Joshua Stein, Cortland, all of N.Y.

[73] Assignee: Cornell Research Foundation, Inc., Ithaca, N.Y.

[21] Appl. No.: 717,331

[22] Filed: Jun. 19, 1991

[51] Int. Cl.$^6$ .................. C07H 21/04; C12N 15/29; C12N 9/12
[52] U.S. Cl. .............. 536/23.6; 536/23.1; 536/23.2; 530/379; 435/194
[58] Field of Search ................. 536/27; 435/172.3, 435/320.1, 194; 935/6, 9; 530/379

[56] References Cited

FOREIGN PATENT DOCUMENTS

WO9013654 11/1990 European Pat. Off. ........ C12N 15/83

OTHER PUBLICATIONS

Nature, 345:743, Jun. 21st, 1990.
Molecular and General Genetics, 222:241, (1990).
Proceedings of the National Academy of Sciences of USA, 88:8816 (Oct. 1991).
Biotechnol. Plant Sci.: Relevance Agric. Eighties (Symp), pp. 259–264 (1985).
The Plant Cell, 2(1):29 Jan. 1990.
Theor. Appl. Genet, *1(6):769, Jun. 1991.
C. H. Chen et al., (1990), Mol. Gen. Genet., 222:241–248.
B. A. Lalonde et al., (1989), Plant Cell, 1:249–258.
M. Trick et al., (1989), Mol. Gen. Genet., 218:112–117.
M. K. Kandasamy et al., (1989), Devel. Biol., 134:462–472.

*Primary Examiner*—David T. Fox
*Assistant Examiner*—Bruce R. Campbell
*Attorney, Agent, or Firm*—Sughrue, Mion, Zinn, Macpeak & Seas

[57] ABSTRACT

Described herein is a S receptor kinase gene (SRK), derived from the S locus in *Brassica oleracea*, having a extracellular domain highly similar to the secreted product of the S-locus glycoprotein gene.

14 Claims, 9 Drawing Sheets

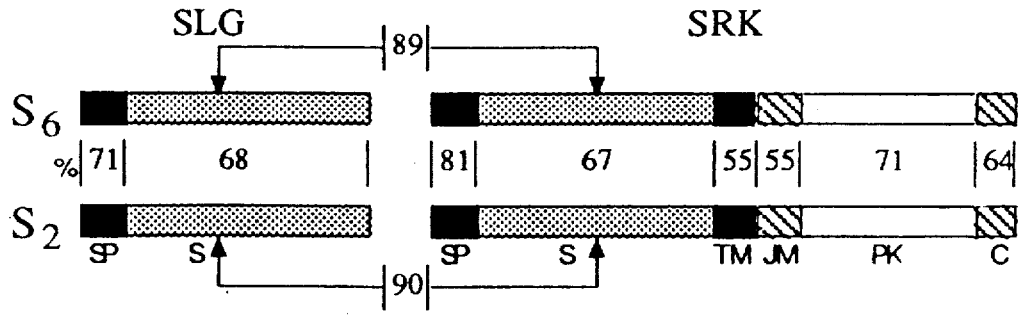

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

Column 13, line 52 to Column 18 (in full), delete in its entirety, and insert therefor --

```
ATG AAA GGG GTA CAG AAC ATT TAC CAC CAT TCT TAC ACC TTC TCG TTC        48
Met Lys Gly Val Gln Asn Ile Tyr His His Ser Tyr Thr Phe Ser Phe
 1               5                  10                  15

TTG CTA GTC TTC CTT GTC TTG ATT CTA TTT CAT CCT GCC CTT TCG ATC        96
Leu Leu Val Phe Leu Val Leu Ile Leu Phe His Pro Ala Leu Ser Ile
             20                  25                  30

TAT GTC AAC ACT TTA TCG TCT TCA GAG TCT CTC ACA ATC TCG AGC AAT       144
Tyr Val Asn Thr Leu Ser Ser Ser Glu Ser Leu Thr Ile Ser Ser Asn
             35                  40                  45

AGA ACA CTT GTA TCT CCC GGT GGA GTC TTC GAG CTT GGT TTC TTC AAA       192
Arg Thr Leu Val Ser Pro Gly Gly Val Phe Glu Leu Gly Phe Phe Lys
 50                  55                  60

CCC TTG GGA CGC TCG CGA TGG TAT CTG GGA ATA TGG TAT AAA AAA GCC       240
Pro Leu Gly Arg Ser Arg Trp Tyr Leu Gly Ile Trp Tyr Lys Lys Ala
 65                  70                  75                  80

CCC TGG AAA ACC TAC GCA TGG GTC GCC AAC AGA GAC AAC CCT CTC TCC       288
Pro Trp Lys Thr Tyr Ala Trp Val Ala Asn Arg Asp Asn Pro Leu Ser
             85                  90                  95

AGT TCT ATT GGA ACC CTC AAA ATC TCT GGC AAC AAT CTT GTC CTG CTA       336
Ser Ser Ile Gly Thr Leu Lys Ile Ser Gly Asn Asn Leu Val Leu Leu
             100                 105                 110

AGT CAG TCT ACT AAC ACT GTT TGG TCG ACA AAT CTT ACT AGA GGA AAT       384
Ser Gln Ser Thr Asn Thr Val Trp Ser Thr Asn Leu Thr Arg Gly Asn
             115                 120                 125

GCG AGA TCT CCG GTG ATA GCA GAG CTT CTT CCC AAC GGT AAT TTT GTA       432
Ala Arg Ser Pro Val Ile Ala Glu Leu Leu Pro Asn Gly Asn Phe Val
 130                 135                 140

ATA AGA CAC TCC AAC AAC AAA GAC TCA AGT GGA TTC TTG TGG CAG AGT       480
Ile Arg His Ser Asn Asn Lys Asp Ser Ser Gly Phe Leu Trp Gln Ser
 145                 150                 155                 160
```

UNITED STATES PATENT AND TRADEMARK OFFICE
CERTIFICATE OF CORRECTION

PATENT NO. : 5,484,905                                                  Page 4 of 17

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
TTC GAT TTT CCG ACA GAT ACT TTA CTT CCG GAG ATG AAA CTA GGT TAC       528
Phe Asp Phe Pro Thr Asp Thr Leu Leu Pro Glu Met Lys Leu Gly Tyr
            165             170             175

GAT CTC AAA ACA GGG CGC AAC AGG TTC CTT ACA TCG TGG AAA GGT TCA       576
Asp Leu Lys Thr Gly Arg Asn Arg Phe Leu Thr Ser Trp Lys Gly Ser
            180             185             190

GAT GAT CCG TCA AGC GGG AAT TTC GTG TAC AAA CTC GAC ATT CGA AGG       624
Asp Asp Pro Ser Ser Gly Asn Phe Val Tyr Lys Leu Asp Ile Arg Arg
            195             200             205

GGA TTG CCT GAG TTT ATT CTT ATA AAT CAA TTT TTG AAT CAA CGT GTT       672
Gly Leu Pro Glu Phe Ile Leu Ile Asn Gln Phe Leu Asn Gln Arg Val
            210             215             220

GAA ACG CAA AGG AGC GGT CCT TGG AAT GGA ATG GAG TTT AGT GGC ATA       720
Glu Thr Gln Arg Ser Gly Pro Trp Asn Gly Met Glu Phe Ser Gly Ile
225             230             235             240

CCG GAG GTG CAG GGA TTA AAT TAC ATG GTT TAC AAT TAT ACG GAG AAC       768
Pro Glu Val Gln Gly Leu Asn Tyr Met Val Tyr Asn Tyr Thr Glu Asn
            245             250             255

AGT GAG GAG ATC GCT TAC TCG TTC CAT ATG ACC AAC CAA AGC ATC TAC       816
Ser Glu Glu Ile Ala Tyr Ser Phe His Met Thr Asn Gln Ser Ile Tyr
            260             265             270

TCC AGA TTG ACA GTC AGT GAG TTG ACA CTC GAT CGA TTG ACG TGG ATC       864
Ser Arg Leu Thr Val Ser Glu Leu Thr Leu Asp Arg Leu Thr Trp Ile
            275             280             285

CCG CCA TCA CGG GAT TGG AGC CTC TTC TGG ACT TTA CCA ACG GAC GTG       912
Pro Pro Ser Arg Asp Trp Ser Leu Phe Trp Thr Leu Pro Thr Asp Val
            290             295             300

TGC GAT CCG CTT TAC TTA TGT GGA TCT TAT TCT TAC TGT GAC CTA ATT       960
Cys Asp Pro Leu Tyr Leu Cys Gly Ser Tyr Ser Tyr Cys Asp Leu Ile
305             310             315             320

ACG TCA CCT AAC TGT AAC TGT ATT AGA GGG TTC GTT CCC AAG AAC CCG      1008
Thr Ser Pro Asn Cys Asn Cys Ile Arg Gly Phe Val Pro Lys Asn Pro
            325             330             335

CAG CAG TGG GAC TTG AGA GAC GGA ACA CGG GGG TGT GTG AGG ACG ACG      1056
Gln Gln Trp Asp Leu Arg Asp Gly Thr Arg Gly Cys Val Arg Thr Thr
            340             345             350
```

UNITED STATES PATENT AND TRADEMARK OFFICE
CERTIFICATE OF CORRECTION

PATENT NO. : 5,484,905            Page 5 of 17

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
CAG ATG AGC TGT AGT GGA GAT GGG TTT TTG CGG CTA AAC AAT ATG AAT       1104
Gln Met Ser Cys Ser Gly Asp Gly Phe Leu Arg Leu Asn Asn Met Asn
        355                 360                 365

TTG CCG GAT ACT AAG ACG GCA ACT GTG GAT CGG ACA ATG GAT GTG AAA       1152
Leu Pro Asp Thr Lys Thr Ala Thr Val Asp Arg Thr Met Asp Val Lys
        370                 375                 380

AAA TGT GAA GAG AGG TGT CTT AGC GAT TGT AAC TGT ACT TCG TTT GCT       1200
Lys Cys Glu Glu Arg Cys Leu Ser Asp Cys Asn Cys Thr Ser Phe Ala
385                 390                 395                 400

ATT GCG GAT GTT CGG AAT GGA GGA TTG GGT TGT GTG TTT TGG ACC GGA       1248
Ile Ala Asp Val Arg Asn Gly Gly Leu Gly Cys Val Phe Trp Thr Gly
                405                 410                 415

GAG CTC GTT GCG ATC AGG AAA TTC GCC GTC GGT GGT CAA GAT CTT TAC       1296
Glu Leu Val Ala Ile Arg Lys Phe Ala Val Gly Gly Gln Asp Leu Tyr
                420                 425                 430

GTC AGA TTG AAT GCT GCT GAT CTA GAT ATT TCC TCG GGT GAG AAG AGA       1344
Val Arg Leu Asn Ala Ala Asp Leu Asp Ile Ser Ser Gly Glu Lys Arg
        435                 440                 445

GAC CGA ACT GGA AAA ATC ATA GGT TGG AGT ATT GGA TCC AGC GTT ATG       1392
Asp Arg Thr Gly Lys Ile Ile Gly Trp Ser Ile Gly Ser Ser Val Met
        450                 455                 460

CTT ATT CTG AGT GTT ATC TTG TTC TGC TTT TGG AGG AGG AGA CAA AAG       1440
Leu Ile Leu Ser Val Ile Leu Phe Cys Phe Trp Arg Arg Arg Gln Lys
465                 470                 475                 480

CAA GCA AAA GCA GAT GCA ACA CCT ATT GTG GGA AAT CAA GTT CTA ATG       1488
Gln Ala Lys Ala Asp Ala Thr Pro Ile Val Gly Asn Gln Val Leu Met
                485                 490                 495

AAC GAG GTG GTG TTA CCA AGA AAG AAG AGA AAT TTT TCT GGA GAG GAC       1536
Asn Glu Val Val Leu Pro Arg Lys Lys Arg Asn Phe Ser Gly Glu Asp
                500                 505                 510

GAT GTA GAA AAT TTG GAA CTT CCA TTG ATG GAG TTT GAA GCT GTT GTC       1584
Asp Val Glu Asn Leu Glu Leu Pro Leu Met Glu Phe Glu Ala Val Val
        515                 520                 525

ACA GCC ACC GAA CAT TTC TCT GAT TTT AAC AAG GTC GGA AAA GGT GGT       1632
Thr Ala Thr Glu His Phe Ser Asp Phe Asn Lys Val Gly Lys Gly Gly
        530                 535                 540
```

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
TTT GGT GTT GTT TAC AAG GGA AGG TTA GTT GAC GGG CAA GAA ATT GCA     1680
Phe Gly Val Val Tyr Lys Gly Arg Leu Val Asp Gly Gln Glu Ile Ala
545             550                 555                 560

GTG AAG AGA CTA TCG GAA ATG TCA GCT CAA GGT ACC GAT GAG TTC ATG     1728
Val Lys Arg Leu Ser Glu Met Ser Ala Gln Gly Thr Asp Glu Phe Met
                565                 570                 575

AAC GAA GTT AGG CTA ATG CAA AGC TTC AGC CAC AAT AAT CTT GTC CGA     1776
Asn Glu Val Arg Leu Met Gln Ser Phe Ser His Asn Asn Leu Val Arg
            580                 585                 590

CTT CTT GGC TGT TGT GTT TAT GAG GGC GAG AAG ATC TTA ATT TAC GAG     1824
Leu Leu Gly Cys Cys Val Tyr Glu Gly Glu Lys Ile Leu Ile Tyr Glu
        595                 600                 605

TAC TTG GAG AAT CTA AGC CTC GAT TCT CAT CTC TTT GAT GAA ACC AGA     1872
Tyr Leu Glu Asn Leu Ser Leu Asp Ser His Leu Phe Asp Glu Thr Arg
    610                 615                 620

AGC TGT ATG TTA AAT TGG CAA ATG AGA TTT GAT ATT ATC AAT GGT ATT     1920
Ser Cys Met Leu Asn Trp Gln Met Arg Phe Asp Ile Ile Asn Gly Ile
625                 630                 635                 640

GCC CGA GGG CTT CTC TAT CTT CAC CAA GAT TCA CGG TTT AGA ATC ATC     1968
Ala Arg Gly Leu Leu Tyr Leu His Gln Asp Ser Arg Phe Arg Ile Ile
                645                 650                 655

CAC AGG GAT TTG AAA GCA AGC AAT GTC TTG CTT GAT AAA GAT ATG ACT     2016
His Arg Asp Leu Lys Ala Ser Asn Val Leu Leu Asp Lys Asp Met Thr
            660                 665                 670

CCA AAA ATT TCA GAC TTT GGA ATG GCT AGG ATC TTT GGA CGG GAT GAG     2064
Pro Lys Ile Ser Asp Phe Gly Met Ala Arg Ile Phe Gly Arg Asp Glu
        675                 680                 685

ACG GAA GCT GAC ACG AGG AAG GTG GTC GGA ACT TAT GGC TAC ATG TCT     2112
Thr Glu Ala Asp Thr Arg Lys Val Val Gly Thr Tyr Gly Tyr Met Ser
    690                 695                 700

CCA GAA TAT GCG ATG AAC GGG ACA TTC TCA ATG AAG TCA GAT GTG TTC     2160
Pro Glu Tyr Ala Met Asn Gly Thr Phe Ser Met Lys Ser Asp Val Phe
705                 710                 715                 720

AGT TTT GGG GTC TTG CTT CTT GAA ATT ATA AGT GGC AAG AGG AAC AAA     2208
Ser Phe Gly Val Leu Leu Leu Glu Ile Ile Ser Gly Lys Arg Asn Lys
                725                 730                 735
```

UNITED STATES PATENT AND TRADEMARK OFFICE
CERTIFICATE OF CORRECTION

PATENT NO. : 5,484,905                                      Page 7 of 17
DATED : January 16, 1996
INVENTOR(S) : June B. NASRALLAH, Mikhail E. NASRALLAH, Joshua STEIN It is certified that error appears in the above-indentified patent and that said Letters Patent is hereby corrected as shown below:

```
GGC TTA TGC GAC TCG GAT AGT AGC CTT AAT CTT CTC GGA TGT GTA TGG       2256
Gly Leu Cys Asp Ser Asp Ser Ser Leu Asn Leu Leu Gly Cys Val Trp
        740                     745                 750

AGG AAT TGG AAA GAA GGT CAA GGT CTA GAG ATA GTA GAC AAG GTC ATC       2304
Arg Asn Trp Lys Glu Gly Gln Gly Leu Glu Ile Val Asp Lys Val Ile
        755                     760                 765

ATA GAT TCT TCA TCA CCA ACG TTC AGG CCA CGT GAA ATA TTA AGA TGC       2352
Ile Asp Ser Ser Ser Pro Thr Phe Arg Pro Arg Glu Ile Leu Arg Cys
        770                     775                 780

TTA CAA ATT GGC CTC TTG TGT GTT CAA GAA CGT GTG GAG GAT AGA CCA       2400
Leu Gln Ile Gly Leu Leu Cys Val Gln Glu Arg Val Glu Asp Arg Pro
785                     790                 795                 800

ATG ATG TCG TCA GTA GTT TTG ATG CTC GGA AGT GAA GCT GCA TTG ATT       2448
Met Met Ser Ser Val Val Leu Met Leu Gly Ser Glu Ala Ala Leu Ile
                805                     810                 815

CCT CAA CCT AAA CAG CCA GGA TAT TGC GTC AGC GGA AGT TCT CTT GAA       2496
Pro Gln Pro Lys Gln Pro Gly Tyr Cys Val Ser Gly Ser Ser Leu Glu
            820                     825                 830

ACT TAT TCT AGG CGT GAC GAT GAA AAT TGC ACA GTG AAC CAA ATC ACC       2544
Thr Tyr Ser Arg Arg Asp Asp Glu Asn Cys Thr Val Asn Gln Ile Thr
        835                     840                 845

ATG TCG ATC ATT GAC GCT CGG TAATATGATA GTCTTTGATA ATATTCTCAC          2595
Met Ser Ile Ile Asp Ala Arg
850                     855

TATTAAAGTT TTACTAAATG GAAAAAAAGA GTTTTACAAG TTGAGTGACA AAGCGTGCCA     2655

AACTCTTCAG TCTATCGAAA TTTTCATTCA TCCTCTGTAT ATTCTCTCGA ATTGGTTTCG     2715

TTATTTCGAG TCAATTCACA GTCAACAACT GCAG                                 2749 --.
```

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

Column 53 to Column 58 (SEQ ID NO:3 in full), delete in its entirety, and insert therefor --

| | | | | | | | | | | | | | | | | |
|---|---|---|---|---|---|---|---|---|---|---|---|---|---|---|---|---|
| ATG | AAA | GGG | GTA | CAG | AAC | ATT | TAC | CAC | CAT | TCT | TAC | ACC | TTC | TCG | TTC | 48 |
| Met | Lys | Gly | Val | Gln | Asn | Ile | Tyr | His | His | Ser | Tyr | Thr | Phe | Ser | Phe | |
| 1 | | | | 5 | | | | | 10 | | | | | 15 | | |
| TTG | CTA | GTC | TTC | CTT | GTC | TTG | ATT | CTA | TTT | CAT | CCT | GCC | CTT | TCG | ATC | 96 |
| Leu | Leu | Val | Phe | Leu | Val | Leu | Ile | Leu | Phe | His | Pro | Ala | Leu | Ser | Ile | |
| | | | 20 | | | | | 25 | | | | | 30 | | | |
| TAT | GTC | AAC | ACT | TTA | TCG | TCT | TCA | GAG | TCT | CTC | ACA | ATC | TCG | AGC | AAT | 144 |
| Tyr | Val | Asn | Thr | Leu | Ser | Ser | Ser | Glu | Ser | Leu | Thr | Ile | Ser | Ser | Asn | |
| | | 35 | | | | | 40 | | | | | 45 | | | | |
| AGA | ACA | CTT | GTA | TCT | CCC | GGT | GGA | GTC | TTC | GAG | CTT | GGT | TTC | TTC | AAA | 192 |
| Arg | Thr | Leu | Val | Ser | Pro | Gly | Gly | Val | Phe | Glu | Leu | Gly | Phe | Phe | Lys | |
| | 50 | | | | | 55 | | | | | 60 | | | | | |
| CCC | TTG | GGA | CGC | TCG | CGA | TGG | TAT | CTG | GGA | ATA | TGG | TAT | AAA | AAA | GCC | 240 |
| Pro | Leu | Gly | Arg | Ser | Arg | Trp | Tyr | Leu | Gly | Ile | Trp | Tyr | Lys | Lys | Ala | |
| 65 | | | | | 70 | | | | | 75 | | | | | 80 | |
| CCC | TGG | AAA | ACC | TAC | GCA | TGG | GTC | GCC | AAC | AGA | GAC | AAC | CCT | CTC | TCC | 288 |
| Pro | Trp | Lys | Thr | Tyr | Ala | Trp | Val | Ala | Asn | Arg | Asp | Asn | Pro | Leu | Ser | |
| | | | | 85 | | | | | 90 | | | | | 95 | | |
| AGT | TCT | ATT | GGA | ACC | CTC | AAA | ATC | TCT | GGC | AAC | AAT | CTT | GTC | CTG | CTA | 336 |
| Ser | Ser | Ile | Gly | Thr | Leu | Lys | Ile | Ser | Gly | Asn | Asn | Leu | Val | Leu | Leu | |
| | | | 100 | | | | | 105 | | | | | 110 | | | |
| AGT | CAG | TCT | ACT | AAC | ACT | GTT | TGG | TCG | ACA | AAT | CTT | ACT | AGA | GGA | AAT | 384 |
| Ser | Gln | Ser | Thr | Asn | Thr | Val | Trp | Ser | Thr | Asn | Leu | Thr | Arg | Gly | Asn | |
| | | 115 | | | | | 120 | | | | | 125 | | | | |
| GCG | AGA | TCT | CCG | GTG | ATA | GCA | GAG | CTT | CTT | CCC | AAC | GGT | AAT | TTT | GTA | 432 |
| Ala | Arg | Ser | Pro | Val | Ile | Ala | Glu | Leu | Leu | Pro | Asn | Gly | Asn | Phe | Val | |
| | 130 | | | | | 135 | | | | | 140 | | | | | |
| ATA | AGA | CAC | TCC | AAC | AAC | AAA | GAC | TCA | AGT | GGA | TTC | TTG | TGG | CAG | AGT | 480 |
| Ile | Arg | His | Ser | Asn | Asn | Lys | Asp | Ser | Ser | Gly | Phe | Leu | Trp | Gln | Ser | |
| 145 | | | | | 150 | | | | | 155 | | | | | 160 | |

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
TTC GAT TTT CCG ACA GAT ACT TTA CTT CCG GAG ATG AAA CTA GGT TAC         528
Phe Asp Phe Pro Thr Asp Thr Leu Leu Pro Glu Met Lys Leu Gly Tyr
            165             170             175

GAT CTC AAA ACA GGG CGC AAC AGG TTC CTT ACA TCG TGG AAA GGT TCA         576
Asp Leu Lys Thr Gly Arg Asn Arg Phe Leu Thr Ser Trp Lys Gly Ser
            180             185             190

GAT GAT CCG TCA AGC GGG AAT TTC GTG TAC AAA CTC GAC ATT CGA AGG         624
Asp Asp Pro Ser Ser Gly Asn Phe Val Tyr Lys Leu Asp Ile Arg Arg
            195             200             205

GGA TTG CCT GAG TTT ATT CTT ATA AAT CAA TTT TTG AAT CAA CGT GTT         672
Gly Leu Pro Glu Phe Ile Leu Ile Asn Gln Phe Leu Asn Gln Arg Val
            210             215             220

GAA ACG CAA AGG AGC GGT CCT TGG AAT GGA ATG GAG TTT AGT GGC ATA         720
Glu Thr Gln Arg Ser Gly Pro Trp Asn Gly Met Glu Phe Ser Gly Ile
225             230             235             240

CCG GAG GTG CAG GGA TTA AAT TAC ATG GTT TAC AAT TAT ACG GAG AAC         768
Pro Glu Val Gln Gly Leu Asn Tyr Met Val Tyr Asn Tyr Thr Glu Asn
            245             250             255

AGT GAG GAG ATC GCT TAC TCG TTC CAT ATG ACC AAC CAA AGC ATC TAC         816
Ser Glu Glu Ile Ala Tyr Ser Phe His Met Thr Asn Gln Ser Ile Tyr
            260             265             270

TCC AGA TTG ACA GTC AGT GAG TTG ACA CTC GAT CGA TTG ACG TGG ATC         864
Ser Arg Leu Thr Val Ser Glu Leu Thr Leu Asp Arg Leu Thr Trp Ile
            275             280             285

CCG CCA TCA CGG GAT TGG AGC CTC TTC TGG ACT TTA CCA ACG GAC GTG         912
Pro Pro Ser Arg Asp Trp Ser Leu Phe Trp Thr Leu Pro Thr Asp Val
            290             295             300

TGC GAT CCG CTT TAC TTA TGT GGA TCT TAT TCT TAC TGT GAC CTA ATT         960
Cys Asp Pro Leu Tyr Leu Cys Gly Ser Tyr Ser Tyr Cys Asp Leu Ile
305             310             315             320

ACG TCA CCT AAC TGT AAC TGT ATT AGA GGG TTC GTT CCC AAG AAC CCG        1008
Thr Ser Pro Asn Cys Asn Cys Ile Arg Gly Phe Val Pro Lys Asn Pro
            325             330             335

CAG CAG TGG GAC TTG AGA GAC GGA ACA CGG GGG TGT GTG AGG ACG ACG        1056
Gln Gln Trp Asp Leu Arg Asp Gly Thr Arg Gly Cys Val Arg Thr Thr
            340             345             350
```

UNITED STATES PATENT AND TRADEMARK OFFICE
CERTIFICATE OF CORRECTION

PATENT NO. : 5,484,905                                    Page 10 of 17

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
CAG ATG AGC TGT AGT GGA GAT GGG TTT TTG CGG CTA AAC AAT ATG AAT      1104
Gln Met Ser Cys Ser Gly Asp Gly Phe Leu Arg Leu Asn Asn Met Asn
        355                 360                 365

TTG CCG GAT ACT AAG ACG GCA ACT GTG GAT CGG ACA ATG GAT GTG AAA      1152
Leu Pro Asp Thr Lys Thr Ala Thr Val Asp Arg Thr Met Asp Val Lys
        370                 375                 380

AAA TGT GAA GAG AGG TGT CTT AGC GAT TGT AAC TGT ACT TCG TTT GCT      1200
Lys Cys Glu Glu Arg Cys Leu Ser Asp Cys Asn Cys Thr Ser Phe Ala
385                 390                 395                 400

ATT GCG GAT GTT CGG AAT GGA GGA TTG GGT TGT GTG TTT TGG ACC GGA      1248
Ile Ala Asp Val Arg Asn Gly Gly Leu Gly Cys Val Phe Trp Thr Gly
                405                 410                 415

GAG CTC GTT GCG ATC AGG AAA TTC GCC GTC GGT GGT CAA GAT CTT TAC      1296
Glu Leu Val Ala Ile Arg Lys Phe Ala Val Gly Gly Gln Asp Leu Tyr
            420                 425                 430

GTC AGA TTG AAT GCT GCT GAT CTA GAT ATT TCC TCG GGT GAG AAG AGA      1344
Val Arg Leu Asn Ala Ala Asp Leu Asp Ile Ser Ser Gly Glu Lys Arg
        435                 440                 445

GAC CGA ACT GGA AAA ATC ATA GGT TGG AGT ATT GGA TCC AGC GTT ATG      1392
Asp Arg Thr Gly Lys Ile Ile Gly Trp Ser Ile Gly Ser Ser Val Met
        450                 455                 460

CTT ATT CTG AGT GTT ATC TTG TTC TGC TTT TGG AGG AGG AGA CAA AAG      1440
Leu Ile Leu Ser Val Ile Leu Phe Cys Phe Trp Arg Arg Arg Gln Lys
465                 470                 475                 480

CAA GCA AAA GCA GAT GCA ACA CCT ATT GTG GGA AAT CAA GTT CTA ATG      1488
Gln Ala Lys Ala Asp Ala Thr Pro Ile Val Gly Asn Gln Val Leu Met
                485                 490                 495

AAC GAG GTG GTG TTA CCA AGA AAG AAG AGA AAT TTT TCT GGA GAG GAC      1536
Asn Glu Val Val Leu Pro Arg Lys Lys Arg Asn Phe Ser Gly Glu Asp
            500                 505                 510

GAT GTA GAA AAT TTG GAA CTT CCA TTG ATG GAG TTT GAA GCT GTT GTC      1584
Asp Val Glu Asn Leu Glu Leu Pro Leu Met Glu Phe Glu Ala Val Val
        515                 520                 525

ACA GCC ACC GAA CAT TTC TCT GAT TTT AAC AAG GTC GGA AAA GGT GGT      1632
Thr Ala Thr Glu His Phe Ser Asp Phe Asn Lys Val Gly Lys Gly Gly
        530                 535                 540
```

UNITED STATES PATENT AND TRADEMARK OFFICE
CERTIFICATE OF CORRECTION

PATENT NO. : 5,484,905

Page 11 of 17

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
TTT GGT GTT GTT TAC AAG GGA AGG TTA GTT GAC GGG CAA GAA ATT GCA      1680
Phe Gly Val Val Tyr Lys Gly Arg Leu Val Asp Gly Gln Glu Ile Ala
545             550                 555                 560

GTG AAG AGA CTA TCG GAA ATG TCA GCT CAA GGT ACC GAT GAG TTC ATG      1728
Val Lys Arg Leu Ser Glu Met Ser Ala Gln Gly Thr Asp Glu Phe Met
                565                 570                 575

AAC GAA GTT AGG CTA ATG CAA AGC TTC AGC CAC AAT AAT CTT GTC CGA      1776
Asn Glu Val Arg Leu Met Gln Ser Phe Ser His Asn Asn Leu Val Arg
            580                 585                 590

CTT CTT GGC TGT TGT GTT TAT GAG GGC GAG AAG ATC TTA ATT TAC GAG      1824
Leu Leu Gly Cys Cys Val Tyr Glu Gly Glu Lys Ile Leu Ile Tyr Glu
        595                 600                 605

TAC TTG GAG AAT CTA AGC CTC GAT TCT CAT CTC TTT GAT GAA ACC AGA      1872
Tyr Leu Glu Asn Leu Ser Leu Asp Ser His Leu Phe Asp Glu Thr Arg
    610                 615                 620

AGC TGT ATG TTA AAT TGG CAA ATG AGA TTT GAT ATT ATC AAT GGT ATT      1920
Ser Cys Met Leu Asn Trp Gln Met Arg Phe Asp Ile Ile Asn Gly Ile
625             630                 635                 640

GCC CGA GGG CTT CTC TAT CTT CAC CAA GAT TCA CGG TTT AGA ATC ATC      1968
Ala Arg Gly Leu Leu Tyr Leu His Gln Asp Ser Arg Phe Arg Ile Ile
                645                 650                 655

CAC AGG GAT TTG AAA GCA AGC AAT GTC TTG CTT GAT AAA GAT ATG ACT      2016
His Arg Asp Leu Lys Ala Ser Asn Val Leu Leu Asp Lys Asp Met Thr
            660                 665                 670

CCA AAA ATT TCA GAC TTT GGA ATG GCT AGG ATC TTT GGA CGG GAT GAG      2064
Pro Lys Ile Ser Asp Phe Gly Met Ala Arg Ile Phe Gly Arg Asp Glu
        675                 680                 685

ACG GAA GCT GAC ACG AGG AAG GTG GTC GGA ACT TAT GGC TAC ATG TCT      2112
Thr Glu Ala Asp Thr Arg Lys Val Val Gly Thr Tyr Gly Tyr Met Ser
    690                 695                 700

CCA GAA TAT GCG ATG AAC GGG ACA TTC TCA ATG AAG TCA GAT GTG TTC      2160
Pro Glu Tyr Ala Met Asn Gly Thr Phe Ser Met Lys Ser Asp Val Phe
705             710                 715                 720

AGT TTT GGG GTC TTG CTT CTT GAA ATT ATA AGT GGC AAG AGG AAC AAA      2208
Ser Phe Gly Val Leu Leu Leu Glu Ile Ile Ser Gly Lys Arg Asn Lys
                725                 730                 735

GGC TTA TGC GAC TCG GAT AGT AGC CTT AAT CTT CTC GGA TGT GTA TGG      2256
Gly Leu Cys Asp Ser Asp Ser Ser Leu Asn Leu Leu Gly Cys Val Trp
            740                 745                 750
```

UNITED STATES PATENT AND TRADEMARK OFFICE
CERTIFICATE OF CORRECTION

PATENT NO. : 5,484,905
DATED : January 16, 1996
INVENTOR(S) : June B. NASRALLAH, Mikhail E. NASRALLAH, Joshua STEIN It is certified that error appears in the above-indentified patent and that said Letters Patent is hereby corrected as shown below:

```
AGG AAT TGG AAA GAA GGT CAA GGT CTA GAG ATA GTA GAC AAG GTC ATC        2304
Arg Asn Trp Lys Glu Gly Gln Gly Leu Glu Ile Val Asp Lys Val Ile
        755             760             765

ATA GAT TCT TCA TCA CCA ACG TTC AGG CCA CGT GAA ATC TTA AGA TGC        2352
Ile Asp Ser Ser Ser Pro Thr Phe Arg Pro Arg Glu Ile Leu Arg Cys
        770             775             780

TTA CAA ATT GGC CTC TTG TGT GTT CAA GAA CGT GTG GAG GAT AGA CCA        2400
Leu Gln Ile Gly Leu Leu Cys Val Gln Glu Arg Val Glu Asp Arg Pro
785             790             795             800

ATG ATG TCG TCA GTA GTT TTG ATG CTC GGA AGT GAA GCT GCA TTG ATT        2448
Met Met Ser Ser Val Val Leu Met Leu Gly Ser Glu Ala Ala Leu Ile
                805             810             815

CCT CAA CCT AAA CAG CCA GGA TAT TGC GTC AGC GGA AGT TCT CTT GAA        2496
Pro Gln Pro Lys Gln Pro Gly Tyr Cys Val Ser Gly Ser Ser Leu Glu
            820             825             830

ACT TAT TCT AGG CGT GAC GAT GAA AAT TGC ACA GTG AAC CAA ATC ACC        2544
Thr Tyr Ser Arg Arg Asp Asp Glu Asn Cys Thr Val Asn Gln Ile Thr
        835             840             845

ATG TCG ATC ATT GAC GCT CGG TAATATGATA GTCTTTGATA ATATTCTCAC           2595
Met Ser Ile Ile Asp Ala Arg
850             855

TATTAAAGTT TTACTAAATG GAAAAAAAGA GTTTTACAAG TTGAGTGACA AAGCGTGCCA      2655

AACTCTTCAG TCTATCGAAA TTTTCATTCA TCCTCTGTAT ATTCTCTCGA ATTGGTTTCG      2715

TTATTTCGAG TCAATTCACA GTCAACAACT GCAG                                  2749 --.
```

UNITED STATES PATENT AND TRADEMARK OFFICE
CERTIFICATE OF CORRECTION

PATENT NO. : 5,484,905                    Page 13 of 17

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

In Claim 2, line 4 (Column 69-70) to Column 74 (SEQ ID NO:3 in full), delete in its entirety, and insert therefor --

```
ATG AAA GGG GTA CAG AAC ATT TAC CAC CAT TCT TAC ACC TTC TCG TTC       48
Met Lys Gly Val Gln Asn Ile Tyr His His Ser Tyr Thr Phe Ser Phe
 1           5               10                  15

TTG CTA GTC TTC CTT GTC TTG ATT CTA TTT CAT CCT GCC CTT TCG ATC       96
Leu Leu Val Phe Leu Val Leu Ile Leu Phe His Pro Ala Leu Ser Ile
            20               25                  30

TAT GTC AAC ACT TTA TCG TCT TCA GAG TCT CTC ACA ATC TCG AGC AAT      144
Tyr Val Asn Thr Leu Ser Ser Ser Glu Ser Leu Thr Ile Ser Ser Asn
        35               40                  45

AGA ACA CTT GTA TCT CCC GGT GGA GTC TTC GAG CTT GGT TTC TTC AAA      192
Arg Thr Leu Val Ser Pro Gly Gly Val Phe Glu Leu Gly Phe Phe Lys
    50               55                  60

CCC TTG GGA CGC TCG CGA TGG TAT CTG GGA ATA TGG TAT AAA AAA GCC      240
Pro Leu Gly Arg Ser Arg Trp Tyr Leu Gly Ile Trp Tyr Lys Lys Ala
65               70                  75                  80

CCC TGG AAA ACC TAC GCA TGG GTC GCC AAC AGA GAC AAC CCT CTC TCC      288
Pro Trp Lys Thr Tyr Ala Trp Val Ala Asn Arg Asp Asn Pro Leu Ser
             85                  90                  95

AGT TCT ATT GGA ACC CTC AAA ATC TCT GGC AAC AAT CTT GTC CTG CTA      336
Ser Ser Ile Gly Thr Leu Lys Ile Ser Gly Asn Asn Leu Val Leu Leu
            100              105                 110

AGT CAG TCT ACT AAC ACT GTT TGG TCG ACA AAT CTT ACT AGA GGA AAT      384
Ser Gln Ser Thr Asn Thr Val Trp Ser Thr Asn Leu Thr Arg Gly Asn
        115              120                 125

GCG AGA TCT CCG GTG ATA GCA GAG CTT CTT CCC AAC GGT AAT TTT GTA      432
Ala Arg Ser Pro Val Ile Ala Glu Leu Leu Pro Asn Gly Asn Phe Val
    130              135                 140
```

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
ATA AGA CAC TCC AAC AAC AAA GAC TCA AGT GGA TTC TTG TGG CAG AGT        480
Ile Arg His Ser Asn Asn Lys Asp Ser Ser Gly Phe Leu Trp Gln Ser
145             150                 155                 160

TTC GAT TTT CCG ACA GAT ACT TTA CTT CCG GAG ATG AAA CTA GGT TAC        528
Phe Asp Phe Pro Thr Asp Thr Leu Leu Pro Glu Met Lys Leu Gly Tyr
                165                 170                 175

GAT CTC AAA ACA GGG CGC AAC AGG TTC CTT ACA TCG TGG AAA GGT TCA        576
Asp Leu Lys Thr Gly Arg Asn Arg Phe Leu Thr Ser Trp Lys Gly Ser
            180                 185                 190

GAT GAT CCG TCA AGC GGG AAT TTC GTG TAC AAA CTC GAC ATT CGA AGG        624
Asp Asp Pro Ser Ser Gly Asn Phe Val Tyr Lys Leu Asp Ile Arg Arg
        195                 200                 205

GGA TTG CCT GAG TTT ATT CTT ATA AAT CAA TTT TTG AAT CAA CGT GTT        672
Gly Leu Pro Glu Phe Ile Leu Ile Asn Gln Phe Leu Asn Gln Arg Val
    210                 215                 220

GAA ACG CAA AGG AGC GGT CCT TGG AAT GGA ATG GAG TTT AGT GGC ATA        720
Glu Thr Gln Arg Ser Gly Pro Trp Asn Gly Met Glu Phe Ser Gly Ile
225                 230                 235                 240

CCG GAG GTG CAG GGA TTA AAT TAC ATG GTT TAC AAT TAT ACG GAG AAC        768
Pro Glu Val Gln Gly Leu Asn Tyr Met Val Tyr Asn Tyr Thr Glu Asn
                245                 250                 255

AGT GAG GAG ATC GCT TAC TCG TTC CAT ATG ACC AAC CAA AGC ATC TAC        816
Ser Glu Glu Ile Ala Tyr Ser Phe His Met Thr Asn Gln Ser Ile Tyr
            260                 265                 270

TCC AGA TTG ACA GTC AGT GAG TTG ACA CTC GAT CGA TTG ACG TGG ATC        864
Ser Arg Leu Thr Val Ser Glu Leu Thr Leu Asp Arg Leu Thr Trp Ile
        275                 280                 285

CCG CCA TCA CGG GAT TGG AGC CTC TTC TGG ACT TTA CCA ACG GAC GTG        912
Pro Pro Ser Arg Asp Trp Ser Leu Phe Trp Thr Leu Pro Thr Asp Val
    290                 295                 300

TGC GAT CCG CTT TAC TTA TGT GGA TCT TAT TCT TAC TGT GAC CTA ATT        960
Cys Asp Pro Leu Tyr Leu Cys Gly Ser Tyr Ser Tyr Cys Asp Leu Ile
305                 310                 315                 320

ACG TCA CCT AAC TGT AAC TGT ATT AGA GGG TTC GTT CCC AAG AAC CCG       1008
Thr Ser Pro Asn Cys Asn Cys Ile Arg Gly Phe Val Pro Lys Asn Pro
                325                 330                 335
```

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
CAG CAG TGG GAC TTG AGA GAC GGA ACA CGG GGG TGT GTG AGG ACG ACG        1056
Gln Gln Trp Asp Leu Arg Asp Gly Thr Arg Gly Cys Val Arg Thr Thr
            340             345                 350

CAG ATG AGC TGT AGT GGA GAT GGG TTT TTG CGG CTA AAC AAT ATG AAT        1104
Gln Met Ser Cys Ser Gly Asp Gly Phe Leu Arg Leu Asn Asn Met Asn
        355             360                 365

TTG CCG GAT ACT AAG ACG GCA ACT GTG GAT CGG ACA ATG GAT GTG AAA        1152
Leu Pro Asp Thr Lys Thr Ala Thr Val Asp Arg Thr Met Asp Val Lys
    370             375             380

AAA TGT GAA GAG AGG TGT CTT AGC GAT TGT AAC TGT ACT TCG TTT GCT        1200
Lys Cys Glu Glu Arg Cys Leu Ser Asp Cys Asn Cys Thr Ser Phe Ala
385             390                 395             400

ATT GCG GAT GTT CGG AAT GGA GGA TTG GGT TGT GTG TTT TGG ACC GGA        1248
Ile Ala Asp Val Arg Asn Gly Gly Leu Gly Cys Val Phe Trp Thr Gly
            405             410                 415

GAG CTC GTT GCG ATC AGG AAA TTC GCC GTC GGT GGT CAA GAT CTT TAC        1296
Glu Leu Val Ala Ile Arg Lys Phe Ala Val Gly Gly Gln Asp Leu Tyr
        420             425                 430

GTC AGA TTG AAT GCT GCT GAT CTA GAT ATT TCC TCG GGT GAG AAG AGA        1344
Val Arg Leu Asn Ala Ala Asp Leu Asp Ile Ser Ser Gly Glu Lys Arg
    435             440             445

GAC CGA ACT GGA AAA ATC ATA GGT TGG AGT ATT GGA TCC AGC GTT ATG        1392
Asp Arg Thr Gly Lys Ile Ile Gly Trp Ser Ile Gly Ser Ser Val Met
        450             455                 460

CTT ATT CTG AGT GTT ATC TTG TTC TGC TTT TGG AGG AGG AGA CAA AAG        1440
Leu Ile Leu Ser Val Ile Leu Phe Cys Phe Trp Arg Arg Arg Gln Lys
465             470                 475             480

CAA GCA AAA GCA GAT GCA ACA CCT ATT GTG GGA AAT CAA GTT CTA ATG        1488
Gln Ala Lys Ala Asp Ala Thr Pro Ile Val Gly Asn Gln Val Leu Met
            485             490                 495

AAC GAG GTG GTG TTA CCA AGA AAG AAG AGA AAT TTT TCT GGA GAG GAC        1536
Asn Glu Val Val Leu Pro Arg Lys Lys Arg Asn Phe Ser Gly Glu Asp
        500             505                 510
```

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

Page 16 of 17

It is certified that error appears in the above-indentified patent and that said Letters Patent is hereby corrected as shown below:

```
GAT GTA GAA AAT TTG GAA CTT CCA TTG ATG GAG TTT GAA GCT GTT GTC    1584
Asp Val Glu Asn Leu Glu Leu Pro Leu Met Glu Phe Glu Ala Val Val
        515             520             525

ACA GCC ACC GAA CAT TTC TCT GAT TTT AAC AAG GTC GGA AAA GGT GGT    1632
Thr Ala Thr Glu His Phe Ser Asp Phe Asn Lys Val Gly Lys Gly Gly
        530             535             540

TTT GGT GTT GTT TAC AAG GGA AGG TTA GTT GAC GGG CAA GAA ATT GCA    1680
Phe Gly Val Val Tyr Lys Gly Arg Leu Val Asp Gly Gln Glu Ile Ala
545             550             555             560

GTG AAG AGA CTA TCG GAA ATG TCA GCT CAA GGT ACC GAT GAG TTC ATG    1728
Val Lys Arg Leu Ser Glu Met Ser Ala Gln Gly Thr Asp Glu Phe Met
        565             570             575

AAC GAA GTT AGG CTA ATG CAA AGC TTC AGC CAC AAT AAT CTT GTC CGA    1776
Asn Glu Val Arg Leu Met Gln Ser Phe Ser His Asn Asn Leu Val Arg
        580             585             590

CTT CTT GGC TGT TGT GTT TAT GAG GGC GAG AAG ATC TTA ATT TAC GAG    1824
Leu Leu Gly Cys Cys Val Tyr Glu Gly Glu Lys Ile Leu Ile Tyr Glu
        595             600             605

TAC TTG GAG AAT CTA AGC CTC GAT TCT CAT CTC TTT GAT GAA ACC AGA    1872
Tyr Leu Glu Asn Leu Ser Leu Asp Ser His Leu Phe Asp Glu Thr Arg
        610             615             620

AGC TGT ATG TTA AAT TGG CAA ATG AGA TTT GAT ATT ATC AAT GGT ATT    1920
Ser Cys Met Leu Asn Trp Gln Met Arg Phe Asp Ile Ile Asn Gly Ile
625             630             635             640

GCC CGA GGG CTT CTC TAT CTT CAC CAA GAT TCA CGG TTT AGA ATC ATC    1968
Ala Arg Gly Leu Leu Tyr Leu His Gln Asp Ser Arg Phe Arg Ile Ile
                645             650             655

CAC AGG GAT TTG AAA GCA AGC AAT GTC TTG CTT GAT AAA GAT ATG ACT    2016
His Arg Asp Leu Lys Ala Ser Asn Val Leu Leu Asp Lys Asp Met Thr
            660             665             670

CCA AAA ATT TCA GAC TTT GGA ATG GCT AGG ATC TTT GGA CGG GAT GAG    2064
Pro Lys Ile Ser Asp Phe Gly Met Ala Arg Ile Phe Gly Arg Asp Glu
        675             680             685

ACG GAA GCT GAC ACG AGG AAG GTG GTC GGA ACT TAT GGC TAC ATG TCT    2112
Thr Glu Ala Asp Thr Arg Lys Val Val Gly Thr Tyr Gly Tyr Met Ser
        690             695             700
```

UNITED STATES PATENT AND TRADEMARK OFFICE
CERTIFICATE OF CORRECTION

PATENT NO. : 5,484,905

DATED : January 16, 1996

INVENTOR(S) : June B. NASRALLAH, Mikhail E. NASRALLAH, Joshua STEIN

It is certified that error appears in the above-indentified patent and that said Letters Patent is hereby corrected as shown below:

```
CCA GAA TAT GCG ATG AAC GGG ACA TTC TCA ATG AAG TCA GAT GTG TTC       2160
Pro Glu Tyr Ala Met Asn Gly Thr Phe Ser Met Lys Ser Asp Val Phe
705                     710                 715                 720

AGT TTT GGG GTC TTG CTT CTT GAA ATT ATA AGT GGC AAG AGG AAC AAA       2208
Ser Phe Gly Val Leu Leu Leu Glu Ile Ile Ser Gly Lys Arg Asn Lys
                    725                 730                 735

GGC TTA TGC GAC TCG GAT AGT AGC CTT AAT CTT CTC GGA TGT GTA TGG       2256
Gly Leu Cys Asp Ser Asp Ser Ser Leu Asn Leu Leu Gly Cys Val Trp
                740                 745                 750

AGG AAT TGG AAA GAA GGT CAA GGT CTA GAG ATA GTA GAC AAG GTC ATC       2304
Arg Asn Trp Lys Glu Gly Gln Gly Leu Glu Ile Val Asp Lys Val Ile
            755                 760                 765

ATA GAT TCT TCA TCA CCA ACG TTC AGG CCA CGT GAA ATC TTA AGA TGC       2352
Ile Asp Ser Ser Ser Pro Thr Phe Arg Pro Arg Glu Ile Leu Arg Cys
    770                 775                 780

TTA CAA ATT GGC CTC TTG TGT GTT CAA GAA CGT GTG GAG GAT AGA CCA       2400
Leu Gln Ile Gly Leu Leu Cys Val Gln Glu Arg Val Glu Asp Arg Pro
785                 790                 795                 800

ATG ATG TCG TCA GTA GTT TTG ATG CTC GGA AGT GAA GCT GCA TTG ATT       2448
Met Met Ser Ser Val Val Leu Met Leu Gly Ser Glu Ala Ala Leu Ile
                805                 810                 815

CCT CAA CCT AAA CAG CCA GGA TAT TGC GTC AGC GGA AGT TCT CTT GAA       2496
Pro Gln Pro Lys Gln Pro Gly Tyr Cys Val Ser Gly Ser Ser Leu Glu
            820                 825                 830

ACT TAT TCT AGG CGT GAC GAT GAA AAT TGC ACA GTG AAC CAA ATC ACC       2544
Thr Tyr Ser Arg Arg Asp Asp Glu Asn Cys Thr Val Asn Gln Ile Thr
        835                 840                 845

ATG TCG ATC ATT GAC GCT CGG TAATATGATA GTCTTTGATA ATATTCTCAC          2595
Met Ser Ile Ile Asp Ala Arg
    850             855

TATTAAAGTT TTACTAAATG GAAAAAAAGA GTTTTACAAG TTGAGTGACA AAGCGTGCCA     2655

AACTCTTCAG TCTATCGAAA TTTTCATTCA TCCTCTGTAT ATTCTCTCGA ATTGGTTTCG     2715

TTATTTCGAG TCAATTCACA GTCAACAACT GCAG                                 2749
```

(SEQ ID NO:3)

Signed and Sealed this

Sixteenth Day of June, 1998

Attest:

BRUCE LEHMAN

Attesting Officer     Commissioner of Patents and Trademarks